(12) United States Patent
Flynn et al.

(10) Patent No.: US 11,820,794 B2
(45) Date of Patent: Nov. 21, 2023

(54) METHOD FOR ROBUST CONTROL OF GENE EXPRESSION

(71) Applicant: California Institute of Technology, Pasadena, CA (US)

(72) Inventors: Michael J. Flynn, Pasadena, CA (US); Michael B. Elowitz, Pasadena, CA (US); Acacia Hori, Pasadena, CA (US); Viviana Gradinaru, La Canada Flintridge, CA (US)

(73) Assignee: California Institute of Technology, Pasadena, CA (US)

( * ) Notice: Subject to any disclaimer, the term of this patent is extended or adjusted under 35 U.S.C. 154(b) by 392 days.

(21) Appl. No.: 17/100,857

(22) Filed: Nov. 21, 2020

(65) Prior Publication Data

US 2021/0171582 A1   Jun. 10, 2021

Related U.S. Application Data

(60) Provisional application No. 62/939,079, filed on Nov. 22, 2019.

(51) Int. Cl.
| | |
|---|---|
| *C12N 9/50* | (2006.01) |
| *A61K 38/00* | (2006.01) |
| *C07K 14/005* | (2006.01) |
| *C12N 15/86* | (2006.01) |

(52) U.S. Cl.
CPC .......... *C07K 14/005* (2013.01); *C12N 15/86* (2013.01); *A61K 38/00* (2013.01); *C07K 2319/71* (2013.01); *C07K 2319/95* (2013.01)

(58) Field of Classification Search
None
See application file for complete search history.

(56) References Cited

U.S. PATENT DOCUMENTS

| | | |
|---|---|---|
| 2008/0153737 A1 | 6/2008 | Lieberman et al. |
| 2010/0197006 A1 | 8/2010 | Benenson et al. |
| 2020/0071362 A1 | 3/2020 | Gao et al. |
| 2020/0071723 A1 | 3/2020 | Gao et al. |
| 2020/0165576 A1 | 5/2020 | Gradinaru et al. |
| 2020/0277333 A1 | 9/2020 | Chong et al. |

FOREIGN PATENT DOCUMENTS

| | | |
|---|---|---|
| JP | 2017-513526 A | 6/2017 |
| WO | WO 2017-004022 A2 | 1/2017 |
| WO | WO2019/147478 | 8/2019 |
| WO | WO2020/210655 | 10/2020 |

OTHER PUBLICATIONS

Ng et al. (Computational and Systems Biology, Nov. 13, 2018, p. 1-38).*

Beer et al., "Low-level shRNA Cytotoxicity Can Contribue to MYC-inducted Hepatocellular Carcinoma in Adult Mice," Molecular Therapy 2010, 18(1), 161-170.
Bleris et al., "Synthetic incoherent feedforward circuits show adaptation to the amount of their genetic template," Molecular Systems Biology 2011, 7(519), in 12 pages.
Challis et al., "Systemic AAV vectors for widespread and targeted gene delivery in rodents," Nature Protocols 2019, 14, 379-414.
Chan et al., "Engineered AAVs for efficient noninvasive gene delivery to the central and peripheral nervous systems," Nat Neurosci. 2017, 20(8), 1172-1179.
Chung et al., "A compact synthetic pathway rewires cancer signaling to therapeutic effector release," Science 2019, 364(6439), 1-23.
De Felipe & Ryan, "Targeting of Proteins Derived from Self-Processing Polyproteins Containing Multiple Signal Sequences," Traffic 2004, 5, 616-626.
De Felipe, "Skipping the co-expression problem: the new 2A 'CHYSEL' technology," Genetic Vaccines and Therapy 2004, 2(13), in 6 pages.
Deverman et al., "Cre-dependent selection yields AAV variants for widespread gene transfer to the adult brain," Nat Biotechnol 2016, 34(2), 204-209.
Flytzanis et al., "Broad gene expression throughout the mouse and marmoset brain after intravenous delivery of engineered AAV capsids," bioRxiv 2020, in 21 oages, doi: https://doi.org/10.1101/2020.06.16.152975.
Gadalla et al., "Improved Survival and Reduced Phenotypic Severity Following AAV9/MECP2 Gene Transfer to Neonatal and Juvenile Male Mecp2 Knockout Mice," Molecular Therapy 2013, 21(1), 18-30.
Gadalla et al., "Development of a Novel AAV Gene Therapy Cassette with Improved Safety Features and Efficacy in Mouse Model of Rett Syndrome," Molecular Therapy 2017, 5, 180-190.
Gao et al., "Programmable protein circuits in living cells," Science 2018, 361, 1252-1258.
Grimm et al., "Fatality in mice due to oversaturation of cellular microRNA/short hairpin RNA pathways," Nature 2006, 441, 537-541.
Guy et al., "Reversal of Neurological Defects in a Mouse Model of Rett Syndrome," Science 2007, 315(5815), 1143-1147.
Ma et al., "Designing Ago2-specific siRNA/shRNA to Avoid Competition with Endogenous miRNAs," Molecular Therapy Nucleic Acids 2014, 3(e176), in 8 pages. doi:10.1038/mtna.2014.27.
Ma et al., "Defining Network Topologies that Can Achieve Biochemical Adaptation," Cell 2009, 138, 760-773.

(Continued)

*Primary Examiner* — Agnieszka Boesen
(74) *Attorney, Agent, or Firm* — Sheppard, Mullin, Richter & Hampton LLP

(57) ABSTRACT

Disclosed herein include methods, compositions, and kits suitable for robust and tunable control of payload gene expression. Some embodiments provide rationally designed circuits, including miRNA-level and/or protein-level incoherent feed-forward loop circuits, that maintain the expression of a payload at an efficacious level. The circuit can comprise a promoter operably linked to a polynucleotide encoding a fusion protein comprising a payload protein, a protease, and one or more self-cleaving peptide sequences. The payload protein can comprise a degron and a cut site the protease is capable of cutting to expose the degron. The circuit can comprise a promoter operably linked to a polynucleotide comprising a payload gene, a silencer effector cassette, and one or more silencer effector binding sequences.

18 Claims, 47 Drawing Sheets

Specification includes a Sequence Listing.

(56) References Cited

OTHER PUBLICATIONS

Matagne et al., "A codon-optimized Mecp2 transgene corrects breathing deficits and improves survival in a mouse model of Rett syndrome," Neurobiology of Disease 2017, 99, 1-11.
Milo et al., "Network Motifs: Simple Building Blocks of Complex Networks," Science 2002, 298, 824-827.
Raj and Van Oudenaarden et al., "Nature, Nurture, or Chance: Stochastic Gene Expression and Its Consequences," Cell 2008, 135, 216-226.
Segall-Shapiro et al., "Engineered promoters enable constant gene expression at any copy number in bacteria," Nature Biotechnology 2018, 36(4), 352-358.
Shen-Orr et al., "Network motifs in transcriptional regulation network of Escherichia coli," Nature Genetics 2002, in 5 pages.
Sinnett et al., "Improved MECP2 Gene Therapy Extends the Survival of MeCP2-Null Mice without Apparent Toxicity after Intracisternal Delivery," Molecular Therapy 2017, 5, 106-115.
Skene et al., "Neuronal MeCP2 Is Expressed at Near Histone-Octamer Levels and Globally Alters the Chromatin State," Molecular Cell 2010, 37, 457-468.
Strovas et al., "MicroRNA-Based Single-Gene Circuits Buffer Protein Synthesis Rates against Perturbations," ACS Publications 2014, 3, 324-331.
Tillotson et al., "Radically truncated MeCP2 rescues Rett syndrome-like neurological defects," Nature 2017, 550(7676), 398-401.
Varshavsky, "N-degron and C-degron pathway degradation," PNAS 2019, 116(2), 358-366.
Yen et al., "Global Protein Stability Profiling in Mammalian Cells," Science 2008, 322, 918-923.
International Search Report and Written Opinion dated Jul. 29, 2021 for International Patent Application No. PCT/US2020/061696.
Fernandez-Rodriguez, et al., "Post-translational control of genetic circuits using Potyvirus proteases", Nucleic Acids Research 2016, 44(13), 6493-6502.
Jungbluth et al., "Targeted protein depletion in *Saccharomyces cerevisiae* by activation of a bidirectional degron", BMC Systems Biology 2010, 4(176), 1-12.

* cited by examiner

```
In [ ]:
define parameters
alpha = 1
gamma = 1
gamma_deg = 100
K = 10
k = 16.2 * 10**3 ode description
def dxdt(x, t, D, reg = True):
    T, M, Mdeg = x
    if reg:
        cat = k*T*M/(K + M)
    else:
        cat = 0
    return np.array([
        D - T,
        alpha * D - gamma * M - cat,
        cat - gamma_deg * Mdeg
    ])

simulate through 10 TEVP half lives
t = np.linspace(0, 10, 2000)

plot solution to ode for D=1,10,30 and 100
fig, ax = plt.subplots(1,2, figsize = (12,5))
for D in [1,10,30,100]:

solve
    sol = scipy.integrate.odeint(
            dxdt,
            y0 = np.array([0,0,0]),
            t = t,
            args = (D,),
    )

we want to look at both no-degron and with-degron solutions
    ax[0].plot(t, sol[:,1], label = "D = {0}".format(D))
    ax[1].plot(t, sol[:,2] + sol[:,1], label = "D = {0}".format(D))

asymptote of no-degron solution
M_asym = alpha * K / (k-alpha)

ax[0].set_xlabel("Time (TEVP Half-lives)")
ax[0].set_ylabel("Concentration [WT MECP2 concentrations]")
ax[0].set_title("Uncleaved MECP2 ($M_{{asym}}$ = {0:.3f})".format(M_asym))
ax[0].legend()

ax[1].set_title("Uncleaved + Cleaved MECP2, $M_{{ss}}$ = D/{0}".format(gamma_deg))
ax[1].set_ylabel("Concentration [WT MECP2 concentrations]")
ax[1].set_xlabel("Time (TEVP Half-lives)")
ax[1].legend()

plt.show()
```

*FIG. 14A*

```
In [ ]:
Ds = np.logspace(-2, 2, 1000)
plt.figure(figsize = (5, 5))
for rat, gamma, kok, gamma_1 in [(1, 100, "high", "high"), (1, .5, "high"
, "low"), (0.2, 20, "low", "high"), (0.2, .5, "low", "low"),]:
    K = 10 / np.sqrt(rat/4.51)
    k = 16.2 * 10**3 * np.sqrt(rat/4.51)

sol = scipy.integrate.odeint(
        dxdt,
        y0 = np.array([0,0,0]),
        t = t,
        args = (D,),
    )

outputs = [scipy.integrate.odeint(
        dxdt,
        y0 = np.array([0,0,0]),
        t = t,
        args = (D,),
    )[len(t) -1, 1] for D in Ds]

plt.plot(Ds, outputs, label = "$k_{{cat}}/K_M$ = {0}, $\gamma$ = {1}".
format(kok, gamma_1))
    #plt.plot(Ds, K*alpha/(k-alpha) * Ds / (K*gamma/(k-
alpha) + Ds), linestyle = "--
", label = "$k/k = {0:.3f}$ approx".format(K/k))

ax = plt.gca()
ax.set_yscale('log')
ax.set_xscale('log')

plt.gca().set_xticks([1e-2, 1e0, 1e2])
plt.gca().xaxis.set_tick_params(labelsize = 16)
plt.gca().set_yticks([1e-4, 1e-3, 1e-2])
plt.gca().yaxis.set_tick_params(labelsize = 16)

plt.xlabel("Dosage (AU)", fontsize = 16)
plt.ylabel("Steady State Expression (AU)", fontsize = 20)
plt.title("Simulation Output", fontsize = 20)
plt.legend(fontsize = 10)#bbox_to_anchor=(1, 1)
plt.show()
```

```python
In [ ]:
    Ds = np.logspace(0.0000001, 3, 1000)
    plt.figure(figsize = (8, 5))
    rat, gamma, kok, gamma_1 = (.00005, .000001, "high", "high")
    for reg in [True, False]:
        K = 10 / np.sqrt(rat/4.51)
        k = 16.2 * 10**3 * np.sqrt(rat/4.51)

sol = scipy.integrate.odeint(
            dxdt,
            y0 = np.array((0,0,0)),
            t = t,
            args = (D,reg),
        )

outputs = [scipy.integrate.odeint(
            dxdt,
            y0 = np.array((0,0,0)),
            t = t,
            args = (D,reg),
        )[len(t) -1, 1] for D in Ds]

if reg:
            color = (112.0/255, 173.0/255, 71.0/255)
        else:
            color = (160.0/255, 70.0/255, 114.0/255)

plt.plot(Ds, outputs, color = color, linewidth = 3)
        #plt.plot(Ds, K*alpha/(k-alpha) * Ds / (K*gamma/(k-alpha) + Ds), linestyle = "----
", label = "$k/k = {0:.3f}$ approx".format(K/k))

ax = plt.gca()
    ax.set_yscale('log')
    ax.set_xscale('log')

plt.gca().set_xticks([1e0, 1e1, 1e2, 1e3])
    plt.gca().xaxis.set_tick_params(labelsize = 20)
    plt.gca().set_yticks([1e1, 1e2, 1e3, 1e4])
    plt.gca().yaxis.set_tick_params(labelsize = 20)

plt.xlabel("Viral Dosage (AU)", fontsize = 20)
    plt.ylabel("Output Expression (AU)", fontsize = 20)
    plt.title("IFFL Schematic", fontsize = 20)
    plt.legend(fontsize = 12)#bbox_to_anchor=(1, 1)
    plt.show()
```

*FIG. 17A*

```
In [ ]:
for K in [10,20,40,80,160]:

solve
    sol = scipy.integrate.odeint(
            dxdt,
            y0 = np.array([0,0,0]),
            t = t,
            args = (D,),
        )

plt.plot(t, sol[:,1], label = "K = {0}".format(K))
    plt.axhline(y = K/k, linestyle = "--")

plt.ylim(0, 0.02)
plt.xlabel("Time [TEVP Half lives]")
plt.ylabel("Concentration [WT MECP2 concentration]")
plt.title("Confirming $M_{asym} = K/k$ (blue dotted lines)")
plt.legend()
plt.show()
```

*FIG. 18A*

```
In [ ]:
for k in [10**3,10**3,10**2]:

solve
    sol = scipy.integrate.odeint(
            dxdt,
            y0 = np.array([0,0,0]),
            t = t,
            args = (D,),
        )

plt.plot(t, sol[:,1], label = "k = {0}".format(k))
    plt.axhline(y = K/(k), linestyle = "--")

plt.ylim(0,3)
plt.xlabel("Time [TEVP Half lives]")
plt.ylabel("Concentration [WT MECP2 concentration]")
plt.title("Confirming $M_{asym} = K/k$ (blue dotted lines)")
plt.legend()
plt.show()
```

*FIG. 19A*

```python
In [ ]:
fig, ax = plt.subplots(1,2, figsize = (12, 5))
for k, alpha in [(1, 2), (2,1)]:
    for D in [500, 1000, 1500, 2000, 2500, 3000]:
        ## solve
        sol = scipy.integrate.odeint(
            dxdt,
            y0 = np.array([0,0,0]),
            t = t,
            args = (D,),
        )
        ax[k-1].plot(t, sol[:,1])

ax[1].axvline(x = 1/k + 2*K/D, color ="red", linestyle= "--")

ax[0].set_title("$k - \\alpha < 0$, grows with Dosage")
ax[1].set_title("$k - \\alpha > 0$, reaches asymptote")

ax[0].set_xlabel("Time [TSVP half lives]")
ax[1].set_xlabel("Time [TSVP half lives]")

ax[0].set_ylabel("Concentration")
ax[1].set_ylabel("Concentration")

Out[ ]: Text(0,0.5,'Concentration')
```

FIG. 20A

```
In [ ]:
for k, K in [(150,50)]:

solve
    sol = scipy.integrate.odeint(
        dxdt,
        y0 = np.array([0,0,0]),
        t = t,
        args = (D,),
    )

plt.plot(t, sol[:,1])

#print(sol[len(t)-1,1])
plt.xlabel("Time [TEVP Half lives]")
plt.ylabel("Concentration [WT MECP2 concentration]")
plt.title("Ideal scenario where k/K has been 1000-
fold reduced\n+ TEVP is truly cataltic")
plt.legend()
plt.show()
```

Ds = np.linspace(0.1, 5, 100)

for rat in [4.51, 0.35, 0.027, 0.007]:
    K = 10 / np.sqrt(rat/4.51)
    k = 16.2 * 10**3 * np.sqrt(rat/4.51)

sol = scipy.integrate.odeint(
            dxdt,
            y0 = np.array([0,0,0]),
            t = t,
            args = (D,),
        )

outputs = [scipy.integrate.odeint(
            dxdt,
            y0 = np.array([0,0,0]),
            t = t,
            args = (D,),
        )[len(t) -1, 1] for D in Ds]

plt.semilogy(Ds, outputs, label = "$k_{(cat)}/K_{(M)} = {0:.3f}$".f
ormat(rat))

plt.xlabel("Dosage (WT dosage)")
plt.ylabel("Steady State concentration \n(WT MECP2 concentration)")
#plt.title("Confirming $M_{asym} = K/k$ (blue dotted lines)")
plt.legend(bbox_to_anchor=(1, 0.5))
plt.show()
```

*FIG. 22A*

# METHOD FOR ROBUST CONTROL OF GENE EXPRESSION

RELATED APPLICATIONS

This application claims the benefit under 35 U.S.C. § 119(e) of U.S. Provisional Patent Application Ser. No. 62/939,079, filed Nov. 22, 2019, the content of this related application is incorporated herein by reference in its entirety for all purposes.

STATEMENT REGARDING FEDERALLY SPONSORED R&D

This invention was made with government support under Grant No. HR011-17-2-0008 awarded by DARPA. The government has certain rights in the invention.

REFERENCE TO SEQUENCE LISTING

The present application is being filed along with a Sequence Listing in electronic format. The Sequence Listing is provided as a file entitled Sequence_Listing_30KJ_302423_US, created Nov. 21, 2020, which is 4.0 kilobytes in size. The information in the electronic format of the Sequence Listing is incorporated herein by reference in its entirety.

BACKGROUND

Field

The present disclosure relates generally to the field of polynucleotide delivery and expression.

Description of the Related Art

Although recent advances have been made in gene manipulation methods and more efficient delivery methods have been introduced, therapeutically effective gene therapy requires that the payload (e.g., a replacement gene) be expressed in a controlled manner in the target cell(s). For example, precise control of MeCP2 expression is required for Rett Syndrome gene therapy. Since CRE-induced expression of MeCP2 was shown to reverse the symptoms of Rett syndrome in a mouse model, several attempts have been made at treating the disease in mice with Adeno-associated virus (AAV)-delivered MeCP2. However, the level of ectopic MeCP2 expression is difficult to control due to various factors, for example variation in gene delivery due to tropism or accessibility; stochasticity in transcription, translation, or other aspects of expression; and heterogeneity in the levels of cellular components that affect protein expression. In Rett Syndrome gene therapy, this variability has manifested as toxically high expression of MeCP2 in the liver, while insufficient MeCP2 is expressed in the brain, so that neither an increase or decrease in the viral dosage of a standard gene therapy vector would be therapeutically effective. However, no gene therapy has been put forth that integrates a rationally designed circuit to control the expression of its payload. There is a need for compositions, methods, and systems for robust and tunable control of payload gene expression.

SUMMARY

Disclosed herein include nucleic acids capable of enabling robust and tunable control of gene expression. In some embodiments, the nucleic acid comprises: a promoter operably linked to a polynucleotide encoding a fusion protein comprising a payload protein, a protease, and one or more self-cleaving peptide sequences, wherein the payload protein comprises a degron and a cut site the protease is capable of cutting to expose the degron, and wherein the degron of the payload protein being exposed changes the payload protein to a payload protein destabilized state. In some embodiments, the promoter is capable of inducing the transcription of the polynucleotide to generate a payload transcript.

In some embodiments, the degron comprises an N-degron. In some embodiments, the self-cleaving peptide sequence comprises porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof. In some embodiments, the protease comprises tobacco etch virus (TEV) protease, tobacco vein mottling virus (TVMV) protease, hepatitis C virus protease (HCVP), derivatives thereof, or any combination thereof. In some embodiments, the protease comprises TEVP, and wherein the cut site comprises the amino acid sequence of ETVFFQ (SEQ ID NO: 1), ENAYFQ (SEQ ID NO: 2), ENLFFQ (SEQ ID NO: 3), ENLYFQ (SEQ ID NO: 4), ENLYFQY (SEQ ID NO: 5), ENLYFQF (SEQ ID NO: 6), ENLYFQQ (SEQ ID NO: 7), or ENLFFQY (SEQ ID NO: 8).

Disclosed herein include nucleic acids. In some embodiments, the nucleic acid comprises: a promoter operably linked to a polynucleotide comprising a payload gene and a silencer effector cassette, wherein the payload gene 3'UTR comprises one or more silencer effector binding sequences. In some embodiments, the promoter is capable of inducing the transcription of the polynucleotide to generate a payload transcript. In some embodiments, the payload gene encodes a payload protein. In some embodiments, payload gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the silencer effector cassette comprises a miRNA cassette. The polynucleotide can comprise: a transcript stabilization element (e.g., hepatitis post-translational regulatory element (WPRE), bovine growth hormone polyadenylation (bGH-polyA) signal sequence, human growth hormone polyadenylation (hGH-polyA) signal sequence, or any combination thereof).

In some embodiments, an intron is located in the payload gene 3'UTR, payload gene 5'UTR, or between payload gene exons, and wherein the intron comprises the silencer effector cassette. In some embodiments, the intron comprises: (i) an intronic insert encoding a silencer effector, (ii) a donor splice site, (iii) an acceptor splice site, (iv) a branch point domain; and (v) a polypyrimidine tract. In some embodiments, said silencer effector is capable of being released from said intron by an intron excision mechanism selected from the group comprising cellular RNA splicing and/or processing machinery, nonsense-mediated decay (NMD) processing, or any combination thereof.

In some embodiments, silencer effector comprises a microRNA (miRNA), a precursor microRNA (pre-miRNA), a small interfering RNA (siRNA), a short-hairpin RNA (shRNA), precursors thereof, derivatives thereof, or a combination thereof. In some embodiments, the promoter is capable of inducing the transcription of the polynucleotide to generate a payload transcript. In some embodiments, said silencer effector is capable of binding the one or more silencer effector binding sequences, thereby reducing the stability of the payload transcript and/or reducing the translation of the payload transcript. In some embodiments, the one or more silencer effector binding sequences comprise miRNA binding sites. In some embodiments, the polynucleotide comprises about 1 silencer effector binding sequence to about 10 silencer binding sequences. In some embodiments, the one or more silencer effector binding sequences are about 8 nucleotides to about 22 nucleotides in length. In some embodiments, the silencer effector comprises a region of complementarity that is complementary with at least 5 consecutive nucleotides of the one or more silencer effector binding sequences. In some embodiments, the silencer effector comprises at least about 50% complementarity to the one or more silencer effector binding sequences.

In some embodiments, one or more cells comprise an endogenous version of a gene encoding the payload protein, and wherein the silencer effector comprises at least about 50% complementarity to one or more endogenous silencer effector binding sequences within the 3'UTR of the endogenous version. In some embodiments, one or more cells comprise an endogenous version of a gene encoding the payload protein comprising one or more secondary silencer binding sequences in the 3'UTR, wherein the nucleic acid comprises a secondary silencer effector cassette encoding a secondary silencer effector that is capable of binding the one or more secondary silencer binding sequences.

In some embodiments, the promoter comprises a ubiquitous promoter. In some embodiments, the ubiquitous promoter is selected from the group comprising a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof. In some embodiments, the promoter is an inducible promoter (e.g., a tetracycline responsive promoter, a TRE promoter, a Tre3G promoter, an ecdysone responsive promoter, a cumate responsive promoter, a glucocorticoid responsive promoter, and estrogen responsive promoter, a PPAR-γ promoter, and/or an RU-486 responsive promoter).

In some embodiments, the promoter comprises a tissue-specific promoter and/or a lineage-specific promoter. In some embodiments, the tissue specific promoter is a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MIC) promoter, or a cardiac Troponin T (cTnT) promoter. In some embodiments, the tissue specific promoter is a neuron-specific promoter (e.g., the neuron-specific promoter comprises a synapsin-1 (Syn) promoter, a CaMKIIa promoter, a calcium/calmodulin-dependent protein kinase II a promoter, a tubulin alpha I promoter, a neuron-specific enolase promoter, a platelet-derived growth factor beta chain promoter, TRPV1 promoter, a $Na_v1.7$ promoter, a $Na_v1.8$ promoter, a $Na_v1.9$ promoter, or an Advillin promoter). In some embodiments, the tissue specific promoter is a muscle-specific promoter (e.g., a creatine kinase (MCK) promoter). In some embodiments, the promoter is a methyl CpG binding protein 2 (MeCP2) promoter or a derivative thereof (e.g., a MeCP2 promoter truncated to about 229 bp and/or a MeCP2 promoter truncated to about 406 bp). In some embodiments, the promoter comprises an intronic sequence. In some embodiments, the promoter comprises a bidirectional promoter and/or an enhancer (e.g., a CMV enhancer).

In some embodiments, the polynucleotide further encodes a dosage indicator protein. In some embodiments, the dosage indicator protein, the payload protein, and the protease are expressed as a fusion protein. In some embodiments, the nucleic acid comprises a secondary promoter operably linked to a secondary polynucleotide encoding a dosage indicator protein. In some embodiments, the promoter and the secondary promoter are different. In some embodiments, the dosage indicator protein is detectable. In some embodiments, the dosage indicator protein comprises green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3 rsCherry, rsCherryRev, derivatives thereof, or any combination thereof.

In some embodiments, one or more cells comprise an endogenous version of the payload gene, and wherein the promoter comprises or is derived from the promoter of the endogenous version. In some embodiments, the payload protein comprises a disease-associated protein, wherein aberrant expression of the disease-associated protein correlates with the occurrence and/or progression of the disease.

In some embodiments, the payload protein comprises a protein associated with an expression-sensitive disease or disorder. In some embodiments, the payload protein comprises methyl CpG binding protein 2 (MeCP2), DRK1A, KAT6A, NIPBL, HDAC4, UBE3A, EHMT1, one or more genes encoded on chromosome 9q34.3, NPHP1, LIMK1 one or more genes encoded on chromosome 7q11.23, P53, TPI1, FGFR1 and related genes, RA1, SHANK3, CLN3, NF-1, TP53, PFK, CD40L, CYP19A1, PGRN, CHRNA7, PMP22, CD40LG, derivatives thereof, or any combination thereof.

In some embodiments, the payload protein comprises fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof. In some embodiments, the payload protein comprises nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof.

In some embodiments, the payload protein comprises a CRE recombinase, GCaMP, a cell therapy component, a knock-down gene therapy component, a cell-surface exposed epitope, or any combination thereof. In some embodiments, the payload protein comprises a chimeric antigen receptor. In some embodiments, the payload protein is associated with an agricultural trait of interest selected from the group consisting of increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance, increased biomass production, male sterility, or any combination thereof. In some embodiments, the payload protein is associated with a biological manufacturing process selected from the group comprising fermentation, distillation, biofuel production, production of a compound, production of a polypeptide, or any combination thereof.

In some embodiments, the payload protein comprises a diagnostic agent. In some embodiments, the diagnostic agent comprises green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof. In some embodiments, the payload protein comprises a nuclear localization signal (NLS) or a nuclear export signal (NES).

In some embodiments, the payload protein comprises a programmable nuclease. In some embodiments, the programmable nuclease is selected from the group comprising: SpCas9 or a derivative thereof, VRER, VQR, EQR SpCas9; xCas9-3.7; eSpCas9; Cas9-HF1; HypaCas9; evoCas9; HiFi Cas9; ScCas9; StCas9; NmCas9; SaCas9; CjCas9; CasX; Cas9 H940A nickase; Cas12 and derivatives thereof, dcas9-APOBEC1 fusion, BE3, and dcas9-deaminase fusions; dcas9-Krab, dCas9-VP64, dCas9-Tet1, and dcas9-transcriptional regulator fusions; Dcas9-fluorescent protein fusions; Cas13-fluorescent protein fusions; RCas9-fluorescent protein fusions; Cas13-adenosine deaminase fusions. In some embodiments, the programmable nuclease comprises a zinc finger nuclease (ZFN) and/or transcription activator-like effector nuclease (TALEN). In some embodiments, the programmable nuclease comprises Streptococcus pyogenes Cas9 (SpCas9), Staphylococcus aureus Cas9 (SaCas9), a zinc finger nuclease, TAL effector nuclease, meganuclease, MegaTAL, Tev-m TALEN, MegaTev, homing endonuclease, Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, or any combination thereof. In some embodiments, the nucleic acid further comprises a polynucleotide encoding (i) a targeting molecule and/or (ii) a donor nucleic acid. In some embodiments, the targeting molecule is capable of associating with the programmable nuclease. In some embodiments, the targeting molecule comprises single strand DNA or single strand RNA. In some embodiments, the targeting molecule comprises a single guide RNA (sgRNA).

In some embodiments, the polynucleotide further encodes one or more secondary proteins. In some embodiments, the payload protein and the one or more secondary proteins are expressed as a fusion protein. In some embodiments, the 3'UTR of the transgene(s) encoding the one or more secondary proteins comprises one or more silencer effector binding sequences. In some embodiments, the payload protein and the one or more secondary proteins comprise a synthetic protein circuit.

In some embodiments, the nucleic acid is a vector (e.g., a viral vector, a plasmid, a naked DNA vector, a lipid nanoparticle, or any combination thereof). In some embodiments, the viral vector is an AAV vector, a lentivirus vector, a retrovirus vector, an integration-deficient lentivirus (IDLV) vector.

Disclosed herein include compositions comprising a nucleic acid disclosed herein. In some embodiments, the composition comprises a vector, a ribonucleoprotein (RNP) complex, a liposome, a nanoparticle, an exosome, a microvesicle, or any combination thereof, comprising a nucleic acid disclosed herein.

In some embodiments, the composition comprises (i) a targeting molecule or a nucleic acid encoding the targeting molecule and/or (ii) a donor nucleic acid or a nucleic acid encoding the donor nucleic acid. In some embodiments, the targeting molecule is capable of associating with the programmable nuclease. In some embodiments, the targeting molecule comprises single strand DNA or single strand RNA. In some embodiments, the targeting molecule comprises a single guide RNA (sgRNA).

In some embodiments, the vector is a viral vector, a plasmid, a naked DNA vector, a lipid nanoparticle, or any combination thereof. In some embodiments, the viral vector is an AAV vector, a lentivirus vector, a retrovirus vector, an integration-deficient lentivirus (IDLV) vector. In some embodiments, the AAV vector comprises single-stranded AAV (ssAAV) vector or a self-complementary AAV (scAAV) vector. In some embodiments, the AAV vector comprises AAV1, AAV2, AAV3, AAV4, AAV5, AAV6, AAV7, AAV8, AAV9, derivatives thereof, or any combination thereof. In some embodiments, the AAV vector comprises an AAV9 variant engineered for systemic delivery (e.g., AAV-PHP.B, AAV-PHP.eB, or AAV-PHP.S). In some embodiments, the vector is a neurotropic viral vector (e.g., comprises or is derived from Herpesviridae, varicella zoster virus, pseudorabies virus, cyromegalovirus, Epstein-barr virus, encephalitis virus, polio virus, coxsackie virus, echo virus, mumps virus, measles virus, rabies virus, or any combination thereof).

Disclosed herein include methods of treating a disease or disorder in a subject. In some embodiments, the method comprises: introducing into one or more cells of a subject in need thereof a composition comprising a nucleic acid disclosed herein, a composition disclosed herein, and/or a nucleic acid disclosed herein.

Disclosed herein include methods for tuned dosage-invariant expression of a payload protein in one or more cells. In some embodiments, the method comprises: introducing into one or more cells a composition comprising a nucleic acid disclosed herein, a composition disclosed herein, and/or a nucleic acid disclosed herein.

In some embodiments, the one or more cells comprise one or more cells of a subject. In some embodiments, the subject is suffering from a disease or disorder. In some embodiments, the one or more cells comprise a neuron. In some embodiments, the neuron is associated with a neurological disease or disorder. The method can comprise: introducing an inducer (e.g., doxycycline) of the inducible promoter to the one or more cells. In some embodiments, the introducing step comprises administering an initial dose of the inducer followed one or more lower maintenance doses of the inducer.

In some embodiments, the introducing step comprises administering a composition comprising a nucleic acid disclosed herein, a composition disclosed herein, and/or a nucleic acid disclosed herein, to a subject comprising the one or more cells. In some embodiments, the administering comprises systemic administration (e.g., intravenous, intramuscular, intraperitoneal, or intraarticular). In some embodiments, administering comprises intrathecal administration, intracranial injection, aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof.

In some embodiments, administering comprises an injection into a brain region (e.g., direct administration to the brain parenchyma). In some embodiments, the brain region comprises the Lateral parabrachial nucleus, brainstem, Medulla oblongata, Medullary pyramids, Olivary body, Inferior olivary nucleus, Rostral ventrolateral medulla, Respiratory center, Dorsal respiratory group, Ventral respiratory group, Pre-Botzinger complex, Botzinger complex, Paramedian reticular nucleus, Cuneate nucleus, Gracile nucleus, Intercalated nucleus, Area postrema, Medullary cranial nerve nuclei, Inferior salivatory nucleus, Nucleus ambiguus, Dorsal nucleus of vagus nerve, Hypoglossal nucleus, Solitary nucleus, Pons, Pontine nuclei, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, Tectum, Corpora quadrigemina, inferior colliculi, superior colliculi, Pretectum, Tegmentum, Periaqueductal gray, Parabrachial area, Medial parabrachial nucleus, Subparabrachial nucleus (Kolliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), Pineal body, Habenular nucleim Stria medullares, Taenia thalami, Subcommissural organ, Thalamus, Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, Hypothalamus, limbic system, HPA axis, preoptic area, Medial preoptic nucleus, Suprachiasmatic nucleus, Paraventricular nucleus, Supraoptic nucleusm Anterior hypothalamic nucleus, Lateral preoptic nucleus, median preoptic nucleus, periventricular preoptic nucleus, Tuberal, Dorsomedial hypothalamic nucleus, Ventromedial nucleus, Arcuate nucleus, Lateral area, Tuberal part of Lateral nucleus, Lateral tuberal nuclei, Mammillary nuclei, Posterior nucleus, Lateral area, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, Subthalamus, Subthalamic nucleus, Zona incerta, Pituitary gland, neurohypophysis, Pars intermedia, adenohypophysis, cerebral hemispheres, Corona radiata, Internal capsule, External capsule, Extreme capsule, Arcuate fasciculus, Uncinate fasciculus, Perforant Path, Hippocampus, Dentate gyrus, Cornu ammonis, Cornu ammonis area 1, Cornu ammonis area 2, Cornu ammonis area 3, Cornu ammonis area 4, Amygdala, Central nucleus, Medial nucleus (accessory olfactory system), Cortical and basomedial nuclei, Lateral and basolateral nuclei, extended amygdala, Stria terminalis, Bed nucleus of the stria terminalis, Claustrum, Basal ganglia, Striatum, Dorsal striatum (aka neostriatum), Putamen, Caudate nucleus, Ventral striatum, Striatum, Nucleus accumbens, Olfactory tubercle, Globus pallidus, Subthalamic nucleus, Basal forebrain, Anterior perforated substance, Substantia innominata, Nucleus basalis, Diagonal band of Broca, Septal nuclei, Medial septal nuclei, Lamina terminalis, Vascular organ of lamina terminalis, Olfactory bulb, Piriform cortex, Anterior olfactory nucleus, Olfactory tract, Anterior commissure, Uncus, Cerebral cortex, Frontal lobe, Frontal cortex, Primary motor cortex, Supplementary motor cortex, Premotor cortex, Prefrontal cortex, frontopolar cortex, Orbitofrontal cortex, Dorsolateral prefrontal cortex, dorsomedial prefrontal cortex, ventrolateral prefrontal cortex, Superior frontal gyrus, Middle frontal gyrus, Inferior frontal gyrus, Brodmann areas (4, 6, 8, 9, 10, 11, 12, 24, 25, 32, 33, 44, 45, 46, and/or 47), Parietal lobe, Parietal cortex, Primary somatosensory cortex (S1), Secondary somatosensory cortex (S2), Posterior parietal cortex, postcentral gyrus, precuneus, Brodmann areas (1, 2, 3 (Primary somesthetic area), 5, 7, 23, 26, 29, 31, 39, and/or 40), Occipital lobe, Primary visual cortex (V1), V2, V3, V4, V5/MT, Lateral occipital gyrus, Cuneus, Brodmann areas (17 (V1, primary visual cortex), 18, and/or 19), temporal lobe, Primary auditory cortex (A1), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas (9, 20, 21, 22, 27, 34, 35, 36, 37, 38, 41, and/or 42), Medial superior temporal area (MST), insular cortex, cingulate cortex, Anterior cingulate, Posterior cingulate, dorsal cingulate, Retrosplenial cortex, Indusium griseum, Subgenual area 25, Brodmann areas (23, 24; 26, 29, 30 (retrosplenial areas), 31, and/or 32), cranial nerves (Olfactory (I), Optic (II), Oculomotor (III), Trochlear (IV), Trigeminal (V), Abducens (VI), Facial (VII), Vestibulocochlear (VIII), Glossopharyngeal (IX), Vagus (X), Accessory (XI), Hypoglossal (XII)), or any combination thereof.

In some embodiments, the brain region comprises neural pathways Superior longitudinal fasciculus, Arcuate fasciculus, Thalamocortical radiations, Cerebral peduncle, Corpus callosum, Posterior commissure, Pyramidal or corticospinal tract, Medial longitudinal fasciculus, dopamine system, Mesocortical pathway, Mesolimbic pathway, Nigrostriatal pathway, Tuberoinfundibular pathway, serotonin system, Norepinephrine Pathways, Posterior column-medial lemniscus pathway, Spinothalamic tract, Lateral spinothalamic tract, Anterior spinothalamic tract, or any combination thereof.

The method can comprise: isolating the one or more cells from the subject prior to the introducing step and/or comprising administering the one or more cells into a subject after the introducing step. In some embodiments, the introducing step is performed in vivo, in vitro, and/or ex vivo. In some embodiments, the introducing step comprises calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof.

In some embodiments, the one or more cells comprise a eukaryotic cell. In some embodiments, the eukaryotic cell comprises an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, telo-glial cell, a zymogenic cell, or any combination thereof. In some embodiments, the stem cell comprises an embryonic stem cell, an induced pluripotent stem cell (iPSC), a hematopoietic stem/progenitor cell (HSPC), or any combination thereof. In some embodiments, the one or more cells comprise two or more cells. In some embodiments, the two or more cells comprise a first cell type and a second cell type.

In some embodiments, the polynucleotide is transcribed at a rate at least 1.1-fold higher in the first cell type as compared to the second cell type. In some embodiments, the steady state levels of the payload transcript are at least 1.1-fold higher in the first cell type as compared to the second cell type. In some embodiments, the rate of transcription of the polynucleotide and/or the rate of translation of the payload transcript varies between a first time point and a second time point in a single cell and/or varies between the first cell type and the second cell type at the same time point. In some embodiments, in the absence of the protease and/or the silencer effector, the payload protein reaches untuned steady state payload protein levels in the one or more cells. In some embodiments, untuned steady state payload protein levels range between a lower untuned threshold and an upper untuned threshold of an untuned expression range. In some embodiments, steady state dosage indicator protein levels reflect untuned steady state payload protein levels. In some embodiments, in the presence the protease and/or the silencer effector, the payload protein reaches tuned steady state payload protein levels in the one or more cells. In some embodiments, tuned steady state payload protein levels range between a lower tuned threshold and an upper tuned threshold of a tuned expression range. In some embodiments, at the first time point and the second time point in a single cell, the steady state levels of the payload protein remain within the tuned expression range. In some embodiments, in the first cell type and the second cell type at the same time point, the steady state levels of the payload protein remain within the tuned expression range.

In some embodiments, the lower tuned threshold and/or the upper tuned threshold of a tuned expression range can be reduced by increasing the number of silencer effector binding sequences in the 3' UTR and/or increasing the degree of complementarity between the silencer effector and the one or more silencer effector binding sequences. In some embodiments, the lower tuned threshold and/or the upper tuned threshold of the tuned expression range can be increased by reducing the number of silencer effector binding sequences in the 3' UTR and/or reducing the degree of complementarity between the silencer effector and the one or more silencer effector binding sequences. In some embodiments, the lower tuned threshold and/or the upper tuned threshold of a tuned expression range can be increased by introducing one or more non-canonical amino acid substitutions into the cut site. In some embodiments, the lower tuned threshold and/or the upper tuned threshold of a tuned expression range can be reduced by introducing one or more canonical amino acid substitutions into the cut site.

In some embodiments, the difference between the lower untuned threshold and the upper untuned threshold of the untuned expression range is greater than about two orders of magnitude. In some embodiments, the difference between the lower tuned threshold and the upper tuned threshold of the tuned expression range is less than about one order of magnitude. In some embodiments, the payload protein is efficacious at steady state payload protein levels within the tuned expression range. In some embodiments, the payload protein is inefficacious and/or toxic at steady state payload protein levels above and/or below the tuned expression range. In some embodiments, the payload protein is capable of inducing an immunogenic response and/or a cytokine storm at steady state payload protein levels outside the tuned expression range. In some embodiments, tuned steady state payload protein levels comprise a therapeutic level of the payload protein. In some embodiments, the steady state payload protein levels remain within the tuned expression range across multiple cell types, titers of viral vector, and/or viral vector capsid types. In some embodiments, the tuned steady state payload protein levels are robust to tissue tropism and stochastic expression.

In some embodiments, the disease or disorder comprises a MECP2-related disorder selected from the group comprising Classic Rett Syndrome, MECP2-related Severe Neonatal Encephalopathy, PPM-X Syndrome, or any combination thereof. In some embodiments, the disease or disorder is a blood disease, an immune disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof. In some embodiments, the disease or disorder comprises a neurological disease or disorder. In some embodiments, the neurological disease or disorder comprises Alzheimer's disease, Creutzfeld-Jakob's syndrome/disease, bovine spongiform encephalopathy (BSE), prion related infections, diseases involving mitochondrial dysfunction, diseases involving β-amyloid and/or tauopathy, Down's syndrome, hepatic encephalopathy, Huntington's disease, motor neuron diseases, amyotrophic lateral sclerosis (ALS), olivoponto-cerebellar atrophy, post-operative cognitive deficit (POCD), systemic lupus erythematosus, systemic clerosis, Sjogren's syndrome, Neuronal Ceroid Lipofuscinosis, neurodegenerative cerebellar ataxias, Parkinson's disease, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, convulsions, epileptic convulsions, epilepsy, temporal lobe epilepsy, myoclonic epilepsy, tinnitus, dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, addiction, anxiety disorders, panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimer's disease, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, memory loss, stress, bipolar manic-depressive disorder, drug tolerance, drug tolerance to opioids, movement disorders, fragile-X syndrome, irritable bowel syndrome (IBS), migraine, multiple sclerosis (MS), muscle spasms, pain, chronic pain, acute pain, inflammatory pain, neuropathic pain, posttraumatic stress disorder (PTSD), schizophrenia, spasticity, Tourette's syndrome, eating disorders, food addiction, binge eating disorders, agoraphobia, generalized anxiety disorder, obsessive-compulsive disorder, panic disorder, social phobia, phobic disorders, substance-induced anxiety disorder, delusional disorder, schizoaffective disorder, schizophreniform disorder, substance-induced psychotic disorder, hypertension, or any combination thereof.

In some embodiments, the disease or disorder is an expression-sensitive disease or disorder. In some embodiments, the expression-sensitive disease or disorder is selected from the group comprising Rett Syndrome; Smith-Magenis Syndrome; Phelan-McDermid Syndrome; Cornelia de Lange Syndrome and other NIPBL related disorders; DRK1A, KAT6A and related disorders of severe intellectual disability; Chromosome 2Q37 Deletion Syndrome and other HDAC4 Related Disorders; Angelman Syndrome; Kleefstra Syndrome; Joubert Syndrome and other NPHP1 Related Disorders; Williams Syndrome; Neurofibromatosis Type 1; Li-Fraumeni syndrome and similar p53-related cancer syndromes; Phosphofructokinase Deficiency; X-linked Hyper IgM Syndrome and similar primary immunodeficiency disorders; Triosephosphate isomerase deficiency; Kallman Syndrome; Aromatase Deficiency; Batten Disease, Frontotemporal Dementia and other neurodegenerative disorders related to loss of progranulin; Cholinergic Receptor Nicotinic Alpha 7 Subunit Related Disorders; and Hereditary Neuropathy with liability to Pressure Palsies.

In some embodiments, an expression-sensitive disease or disorder is characterized by decreased expression of one or more proteins, wherein ectopic overexpression of said one or more proteins at a steady state level beyond the upper tuned threshold causes cellular toxicity and/or disease. In some embodiments, said expression-sensitive disorder is a neurodevelopmental syndromic disorder. In some embodiments, the neurodevelopmental syndromic disorder is selected from the group comprising Rett Syndrome, Smith-Magenis Syndrome (RA1), Phelan-McDermid Syndrome (SHANK3), Cornelia de Lange Syndrome (NIPBL) and other NIPBL related disorders, DRK1A, KAT6A and related disorders of severe intellectual disability, Chromosome 2Q37 Deletion Syndrome and other HDAC4 Related Disorders, Angelman Syndrome, Kleefstra Syndrome, Joubert Syndrome and other NPHP1 Related Disorders, and Williams Syndrome. In some embodiments, said expression-sensitive disorder is a proliferative disorder and/or cancer. In some embodiments, the proliferative disorder and/or cancer is selected from the group comprising Neurofibromatosis Type 1 and Li-Fraumeni syndrome and similar p53-related cancer syndromes. In some embodiments, said expression-sensitive disorder is a glycogen storage disorder. In some embodiments, the glycogen storage disorder is phosphofructokinase deficiency. In some embodiments, said expression-sensitive disorder is a hematologic disorder and/or immune disorder. In some embodiments, the hematologic disorder and/or immune disorder is selected from the group comprising X-linked Hyper IgM Syndrome and related primary immunodeficiency disorders, and triosephosphate isomerase deficiency. In some embodiments, said expression-sensitive disorder is an endocrine disorder. In some embodiments, the endocrine disorder is selected from the group comprising Kallman Syndrome and Aromatase Deficiency. In some embodiments, said expression-sensitive disorder is a neuropsychiatric disorder. In some embodiments, the neuropsychiatric disorder is selected from the group comprising Batten Disease, Frontotemporal Dementia and other neurodegenerative disorders related to loss of progranulin, Cholinergic Receptor Nicotinic Alpha 7 Subunit Related Disorders, and Hereditary Neuropathy with liability to Pressure Palsies.

In some embodiments, the payload protein comprises RA1 and the disease or disorder comprises Smith-Magenis Syndrome. In some embodiments, the payload protein comprises SHANK3 and the disease or disorder comprises Phelan-McDermid Syndrome. In some embodiments, the payload protein comprises CLN3 and the disease or disorder comprises Batten Disease. In some embodiments, the payload protein comprises NF-1 and the disease or disorder comprises Neurofibromitosis Type I. In some embodiments, the payload protein comprises TP53 and the disease or disorder comprises Li-Fraumeni Syndrome. In some embodiments, the payload protein comprises PFK and the disease or disorder comprises phosphofructokinase deficiency. In some embodiments, the payload protein comprises CD40LG and the disease or disorder comprises X-linked Hyper IGM disorders.

BRIEF DESCRIPTION OF THE DRAWINGS

FIG. 1A illustrates a non-limiting exemplary single transcript protein-level IFFL provided herein. FIG. 1B depicts fluorescence microscopy images showing de-correlated input and output as a result of the IFFL. FIG. 1C depicts exemplary data showing that tunability is established using different amino acid sequences. FIG. 1D depicts a non-limiting exemplary numerical simulation of the steady state gene expression. FIG. 1E depicts flow cytometry data confirming the numerical and analytic models of TEVP performance.

FIG. 2A illustrates non-limiting exemplary single transcript protein-level IFFLs provided herein. FIG. 2B depicts flow cytometry data. Error bars indicate ±1 standard deviation in log space.

FIG. 3B depicts flow cytometry data. Dots represent medians of bins. Error bars indicate ±1 standard deviation in log space.

FIG. 4A illustrates non-limiting exemplary miRNA-level IFFLs provided herein. FIG. 4B depicts flow cytometry data. Dots represent medians of bins. Error bars indicate ±1 standard deviation in log space.

FIG. 5A illustrates non-limiting exemplary miRNA-level IFFLs provided herein. FIG. 5B depicts flow cytometry data showing 4 levels of MeCP2-EGFP expression. Dots represent medians of bins. Error bars indicate ±1 standard deviation in log space.

FIGS. 14A-14C depict non-limiting exemplary code and simulations.

FIGS. 15A-15B depict non-limiting exemplary code and simulations.

FIGS. 16A-16B depict non-limiting exemplary code and simulations.

FIGS. 17A-17B depict non-limiting exemplary code and simulations.

FIGS. 18A-18B depict non-limiting exemplary code and simulations.

FIGS. 19A-19B depict non-limiting exemplary code and simulations.

FIGS. 20A-20C depict non-limiting exemplary code and simulations.

FIGS. 21A-21B depict non-limiting exemplary code and simulations.

FIGS. 22A-22B depict non-limiting exemplary code and simulations.

DETAILED DESCRIPTION

Figure 1A:
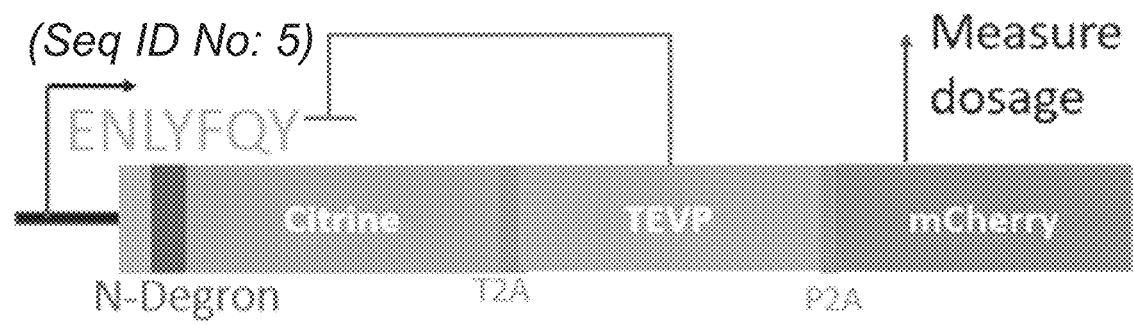
FIGS. 1A-1E depict non-limiting exemplary embodiments and data related to a single robust protein control circuit using TEVP as protease.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include nucleic acids. In some embodiments, the nucleic acid comprises: a promoter operably linked to a polynucleotide encoding a fusion protein comprising a payload protein, a protease, and one or more self-cleaving peptide sequences, wherein the payload protein comprises a degron and a cut site the protease is capable of cutting to expose the degron, and wherein the degron of the payload protein being exposed changes the payload protein to a payload protein destabilized state. In some embodiments, the promoter is capable of inducing the transcription of the polynucleotide to generate a payload transcript.

Disclosed herein include nucleic acids. In some embodiments, the nucleic acid comprises: a promoter operably linked to a polynucleotide comprising a payload gene and a silencer effector cassette, wherein the payload gene 3'UTR comprises one or more silencer effector binding sequences. In some embodiments, the promoter is capable of inducing the transcription of the polynucleotide to generate a payload transcript. In some embodiments, the payload gene encodes a payload protein. In some embodiments, payload gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. In some embodiments, the silencer effector cassette comprises a miRNA cassette. The polynucleotide can comprise: a transcript stabilization element (e.g., hepatitis post-translational regulatory element (WPRE), bovine growth hormone polyadenylation (bGH-polyA) signal sequence, human growth hormone polyadenylation (hGH-polyA) signal sequence, or any combination thereof).

Disclosed herein include compositions comprising a nucleic acid disclosed herein. In some embodiments, the composition comprises a vector, a ribonucleoprotein (RNP) complex, a liposome, a nanoparticle, an exosome, a microvesicle, or any combination thereof, comprising a nucleic acid disclosed herein.

Disclosed herein include methods of treating a disease or disorder in a subject. In some embodiments, the method comprises: introducing into one or more cells of a subject in need thereof a composition comprising a nucleic acid disclosed herein, a composition disclosed herein, and/or a nucleic acid disclosed herein.

Disclosed herein include methods for tuned dosage-invariant expression of a payload protein in one or more cells. In some embodiments, the method comprises: introducing into one or more cells a composition comprising a nucleic acid disclosed herein, a composition disclosed herein, and/or a nucleic acid disclosed herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

As used herein, the term "vector" refers to a polynucleotide construct, typically a plasmid or a virus, used to transmit genetic material to a host cell (e.g., a target cell). Vectors can be, for example, viruses, plasmids, cosmids, or phage. A vector can be a viral vector. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "expression vector" refers to a vector that directs expression of an RNA or polypeptide (e.g., a synthetic protein circuit component) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, 2A sequences or elements refer to small peptides introduced as a linker between two proteins, allowing autonomous intraribosomal self-processing of polyproteins (See e.g., de Felipe. Genetic Vaccines and Ther. 2: 13 (2004); deFelipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine tescho virus-1 (P2A).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may reduce the level of RAS signaling in the subject, thereby to reduce, alleviate, or eradicate the symptom(s) of the disease(s). As used herein, the term "prevention" refers to any activity that reduces the burden of the individual later expressing those symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween, polyethylene glycol (PEG), and Pluronics. Auxiliary, stabilizer, emulsifier, lubricant, binder, pH adjuster controller, isotonic agent and other conventional additives may also be added to the carriers.

Robust and Tunable Control of Gene Expression

There are provided, in some embodiments, methods, compositions, and systems for robust and tunable control of expression of a payload (e.g., payload protein, payload gene). There are provided, in some embodiments, rationally designed circuits enabling the precise control of payload expression (e.g., MeCP2 expression) required for gene therapy (e.g., Rett Syndrome gene therapy). The compositions and methods provided herein enable a tunable and robust control of payload gene expression that solves the problems of standard gene therapy vectors and methods, including but, not limited to, variation in gene delivery due to tropism or accessibility; stochasticity in transcription, translation, or other aspects of expression; and heterogeneity in the levels of cellular components that affect protein expression. For example, embodiments provided wherein the payload protein comprises MeCP2 display both nontoxic expression of MeCP2 in the liver and therapeutically sufficient MeCP2 expression in the brain. There are provided, in some embodiments, rationally designed circuits that control the expression of its payload, including miRNA-level and protein-level incoherent feed-forward loop circuits. In some embodiments, said circuits provide tunable control of gene expression in order to set the expression of an ectopic gene (e.g., transgene, payload protein, payload gene) to a therapeutic level, robust to tissue tropism and stochastic expression. The compositions (e.g., circuits) and methods provided herein solve the problem of MeCP2 expression control in Rett Syndrome gene therapy and can be broadly applied to gene and cell therapies, biological manufacturing processes, and/or any application wherein protein expression stabilization is useful or necessary.

Incoherent feedforward loops have been shown to provide adaptive expression levels, but have not been implemented synthetically with tunable control, at the protein level, or demonstrated as safe and effective in a gene therapy. The incoherent feed-forward loop (IFFL) was first identified as a highly conserved biological circuit motif in E. coli. The motif was later shown to be one of the only biological circuit architectures that maintains a robust steady state over wide ranges of input. Synthetic incoherent feedforward loops have been implemented to stabilize expression of molecular sensors, to adapt gene expression to changes in gene dosage received during transient transfection (Bleris, Leonidas, et al. "Synthetic incoherent feedforward circuits show adaptation to the amount of their genetic template." Molecular systems biology 7.1 (2011): 519) and to buffer gene expression against noise at the single copy level. Currently available compositions and methods employing IFFLs fail to address the existing problems in the art, as it has not been shown that these circuits are tunable, that they can adapt expression over 3 orders of dosage magnitude, that they can be implemented at the protein-level, or that they are safe and effective in an in-vivo gene therapy.

The compositions and methods provided herein can be applied to gene therapies, cell therapies, or cell line development for biological manufacturing. In some embodiments, the circuits provided herein can be employed to express MeCP2 at a controlled level for Rett Syndrome gene therapy. However, the applications of these circuits extend to any gene therapy, in particular gene therapies wherein expression must be controlled, and many other applications in cell therapy or biological manufacturing. For example, in CAR T-cell therapy, the activation of designed T-cells depends on the level of chimeric antigen receptor (CAR) expressed. Noise in CAR expression, for example due to the lentiviral integration site, is propagated through to noise in T-cell activation and increases off target activation. The IFFLs provided herein can stabilize CAR expression and reduce off-target activation. Moreover, this application is not be limited to CARs; for example, the IFFLs provided herein can stabilize expression of sensors used in cell therapy. In some embodiments, the methods and compositions provided herein mitigate Cas9 genotoxicity: Cas9 off-target effects are known to occur and would decrease if Cas9 is expressed at a lower level. Finally, many biological manufacturing processes must deal with varying conditions, such as pH, that result in changes of enzymatic pathway component expression and can thereby result in low yields. IFFLs provided herein can stabilize the expression of these pathway components to reduce yield variability. The catalytic IFFL modules disclosed herein can improve gene therapies, cell based therapies, and biological manufacturing processes. Because the provided methods and compositions can solve a general problem—achieving precisely tunable gene expression levels—the constructs provided herein can a standard enabling component for a wide range of existing and emerging biomedical applications. Provided herein is the first instance of IFFL-based compositions and methods being used in a gene therapy, first instance of being shown to be tunable, and first instance of being shown to have multiple order of magnitude regulation.

Disclosed herein include nucleic acids. In some embodiments, the nucleic acid comprises: a promoter operably linked to a polynucleotide encoding a fusion protein comprising a payload protein, a protease, and one or more self-cleaving peptide sequences. The payload protein can comprise a degron and a cut site the protease is capable of cutting to expose the degron. The degron of the payload protein being exposed can change the payload protein to a payload protein destabilized state. The promoter can be capable of inducing the transcription of the polynucleotide to generate a payload transcript. The payload transcript can encode the fusion protein. A payload gene can encode the payload transcript (e.g., the fusion protein). The nucleic acid can be a vector (e.g., a viral vector, a plasmid, a naked DNA vector, a lipid nanoparticle, or any combination thereof). The nucleic acid can be an expression vector. The viral vector can be an AAV vector, a lentivirus vector, a retrovirus vector, an integration-deficient lentivirus (IDLV) vector.

As described herein, a "cut site" is a peptide sequence specific for one or more proteases that when recognized or bound by the one or more proteases are cleaved by the one or more proteases. The peptide sequence of the cut site may be specific for one protease or a type of proteases, or may be general to multiple proteases or types of proteases.

As used herein, "destabilize" may refer to the ability of a peptide or molecule to prevent or stop the same or another molecule or peptide from maintaining a particular state.

"Destabilize" may also refer to the ability of a peptide or molecule to allow or increase the amount of degradation that the same or another molecule or peptide faces, such as by increasing the affinity of the same or other molecule or peptide to a digestive protein.

The degron can comprise an N-degron. Some degrons are ubiquitin-dependent or ubiquitin-independent. The self-cleaving peptide sequence can comprise porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof. The protease can comprise tobacco etch virus (TEV) protease, tobacco vein mottling virus (TVMV) protease, hepatitis C virus protease (HCVP), derivatives thereof, or any combination thereof. The protease can comprise TEVP. The cut site can comprise an amino acid sequence at least about 25% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, or a number or a range between any two of these values) homologous to the canonical cut of site of a protease. The cut site can comprise an amino acid sequence at least about 25% homologous to the amino acid sequence of ETVFFQ (SEQ ID NO: 1), ENAYFQ (SEQ ID NO: 2), ENLFFQ (SEQ ID NO: 3), ENLYFQ (SEQ ID NO: 4), ENLYFQY (SEQ ID NO: 5), ENLYFQF (SEQ ID NO: 6), ENLYFQQ (SEQ ID NO: 7), or ENLFFQY (SEQ ID NO: 8).

There are provided, in some embodiments, degrons. A degron can comprise DI-FR degron, an N-degron, a phospho degron, a heat inducible degron, a photosensitive degron, an oxygen dependent degron, ornithine decarboxylase degron, estrogen receptor domain degrons, a ecDHFR degron, an FKBP degron, a UnaG degron, or any combination thereof. As a non-limiting example, the degron may be an ornithine decarboxylase degron. The degron can comprise a ecDHFR degron. In some embodiments, the degron and/or cut site is located at the 5' end of the payload protein. In some embodiments, the degron and/or cut site is located at the 3' end of the payload protein. In some embodiments, the degron and/or cut site situated within the payload protein. In some embodiments, the degron and/or cut site situated within the payload protein to for a split protein. In some embodiments, the sequence of the degron (e.g., N-end degron) is varied to tune the expression of the payload protein.

Disclosed herein include nucleic acids. In some embodiments, the nucleic acid comprises: a promoter operably linked to a polynucleotide comprising a payload gene and a silencer effector cassette. The payload gene can comprises one or more silencer effector binding sequences. The one or more silencer effector binding sequences can be located anywhere in the payload gene, such as the 3'UTR, 5'UTR, intron, or any combination thereof. The promoter can be capable of inducing the transcription of the polynucleotide to generate a payload transcript. In some embodiments, the payload gene encodes a payload protein. In some embodiments, the payload gene encodes a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof, which can target the expression of any endogenous gene of interest. The polynucleotide can comprise: a transcript stabilization element (e.g., hepatitis post-translational regulatory element (WPRE), bovine growth hormone polyadenylation (bGH-polyA) signal sequence, human growth hormone polyadenylation (hGH-polyA) signal sequence, or any combination thereof).

The nucleic acid can be a vector (e.g., a viral vector, a plasmid, a naked DNA vector, a lipid nanoparticle, or any combination thereof). The viral vector can be an AAV vector, a lentivirus vector, a retrovirus vector, an integration-deficient lentivirus (IDLV) vector.

The silencer effector cassette can comprise a miRNA cassette. An intron can be located in the payload gene 3'UTR, payload gene 5'UTR, or between payload gene exons. The intron can comprise the silencer effector cassette. The intron can comprise: (i) an intronic insert encoding a silencer effector, (ii) a donor splice site, (iii) an acceptor splice site, (iv) a branch point domain; and/or (v) a polypyrimidine tract. The silencer effector can be capable of being released from said intron by an intron excision mechanism selected from the group comprising cellular RNA splicing and/or processing machinery, nonsense-mediated decay (NMD) processing, or any combination thereof. The silencer effector can comprise a microRNA (miRNA), a precursor microRNA (pre-miRNA), a small interfering RNA (siRNA), a short-hairpin RNA (shRNA), precursors thereof, derivatives thereof, or a combination thereof.

The silencer effector can be capable of binding the one or more silencer effector binding sequences, thereby reducing the stability of the payload transcript and/or reducing the translation of the payload transcript. The one or more silencer effector binding sequences can comprise miRNA binding sites. The polynucleotide can comprise about 1 to about 20 (e.g., 1, 2, 3, 4, 5, 6, 7, 8, 9, 10, 20, or a number or a range between any two of these values) silencer binding sequences. The one or more silencer effector binding sequences can be about 1 to about 50 (e.g., 1, 2, 3, 4, 5, 6, 7, 8, 9, 10, 11, 12, 13, 14, 15, 16, 17, 18, 19, 20, 25, 30, 35, 40, 45, 50, or a number or a range between any two of these values) nucleotides in length. The silencer effector can comprise a region of complementarity that is complementary with at least 5 consecutive nucleotides of the one or more silencer effector binding sequences. The silencer effector can comprise at least about 25% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values) complementarity to the one or more silencer effector binding sequences. In some embodiments, one or more cells comprise an endogenous version (e.g., variant) of a gene encoding the payload protein, and wherein the silencer effector can comprise at least about 25% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values) complementarity to one or more endogenous silencer effector binding sequences within the 3'UTR of the endogenous version. In some embodiments, one or more cells comprise an endogenous version (e.g., variant) of a gene encoding the payload protein comprising one or more secondary silencer binding sequences in the 3'UTR, wherein the nucleic acid can comprise a secondary silencer effector cassette encoding a secondary silencer effector that is capable of binding the one or more secondary silencer binding sequences. In some embodiments, the payload protein is expressed and the endogenous version (e.g., variant) of the payload protein is not expressed.

Disclosed herein include compositions comprising a nucleic acid disclosed herein. In some embodiments, the composition comprises a vector, a ribonucleoprotein (RNP) complex, a liposome, a nanoparticle, an exosome, a microvesicle, or any combination thereof, comprising a nucleic acid disclosed herein. The vector can be a viral vector, a plasmid, a naked DNA vector, a lipid nanoparticle, or any combination thereof. The viral vector can be an AAV vector, a lentivirus vector, a retrovirus vector, an integration-deficient lentivirus (IDLV) vector. The AAV vector can comprise single-stranded AAV (ssAAV) vector or a self-complementary AAV (scAAV) vector. The AAV vector can comprise AAV1, AAV2, AAV3, AAV4, AAV5, AAV6, AAV7, AAV8, AAV9, derivatives thereof, or any combination thereof. The AAV vector can comprise an AAV9 variant engineered for systemic delivery (e.g., AAV-PHP.B, AAV-PHP.eB, or AAV-PHP.S). The vector can be a neurotropic viral vector (e.g., comprises or derived from Herpesviridae, varicella zoster virus, pseudorabies virus, cyromegalovirus, Epstein-barr virus, encephalitis virus, polio virus, coxsackie virus, echo virus, mumps virus, measles virus, rabies virus, or any combination thereof).

Disclosed herein include methods of treating a disease or disorder in a subject. Disclosed herein include methods of preventing a disease or disorder in a subject. Disclosed herein include methods of diagnosing a disease or disorder in a subject. Disclosed herein include methods of performing cell therapy. Disclosed herein include methods of performing biological manufacturing. In some embodiments, the method comprises: introducing into one or more cells of a subject in need thereof a composition comprising a nucleic acid disclosed herein, a composition disclosed herein, and/or a nucleic acid disclosed herein. In some embodiments, the payload protein is a wild-type version of an endogenous protein. In some embodiments, the payload protein is a variant of an endogenous protein.

Disclosed herein include methods for tuned dosage-invariant expression of a payload protein in one or more cells. In some embodiments, the method comprises: introducing into one or more cells a composition comprising a nucleic acid disclosed herein, a composition disclosed herein, and/or a nucleic acid disclosed herein. The one or more cells can comprise one or more cells of a subject. The subject can be suffering from a disease or disorder. The one or more cells can comprise a neuron, such as, for example, a neuron associated with a neurological disease or disorder.

In some embodiments, the introducing step comprises administering a composition comprising a nucleic acid disclosed herein, a composition disclosed herein, and/or a nucleic acid disclosed herein, to a subject comprising the one or more cells. The method can comprise: introducing an inducer (e.g., doxycycline) of the inducible promoter to the one or more cells. The introducing step can comprise administering an initial dose of the inducer followed one or more lower maintenance doses of the inducer.

The method can comprise: isolating the one or more cells from the subject prior to the introducing step and/or comprising administering the one or more cells into a subject after the introducing step. The introducing step can be performed in vivo, in vitro, and/or ex vivo. The introducing step can comprise calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof.

The one or more cells can comprise a eukaryotic cell. The eukaryotic cell can comprise an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. The stem cell can comprise an embryonic stem cell, an induced pluripotent stem cell (iPSC), a hematopoietic stem/progenitor cell (HSPC), or any combination thereof.

The one or more cells can comprise two or more cells (e.g., two or more cells of a subject). The subject can comprise a plurality of cells. Administering the nucleic acids, compositions, and/or vectors provided herein to a subject can cause expression of the payload in two or more cells of the subject. The two or more cells can comprise 2 or more (e.g., 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or a number or a range between any two of these values) different cell types. Same cell types and/or different cell types can be located in different areas of a subject. The basal transcriptional and/or translational machinery of the different cell types can vary amongst themselves and each other. The transcription of the payload transcript and/or translation of the payload transcript can vary among different cells. The two or more cells can comprise a first cell type and a second cell type. The first cell type and second cell type can be the same or different. The polynucleotide can be transcribed at a rate at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) higher in the first cell type as compared to the second cell type. The steady state levels of the payload transcript can be at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) higher in the first cell type as compared to the second cell type.

In some embodiments, the polynucleotide further encodes a dosage indicator protein. The dosage indicator protein, the payload protein, and the protease can be expressed as a fusion protein. The nucleic acid can comprise a secondary promoter operably linked to a secondary polynucleotide encoding a dosage indicator protein. The promoter and the secondary promoter can be different. The dosage indicator protein can be detectable. The dosage indicator protein can comprise green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof. In some embodiments, steady state dosage indicator protein levels reflect untuned steady state payload protein levels.

In some embodiments, the rate of transcription of the polynucleotide and/or the rate of translation of the payload transcript varies between a first time point and a second time point in a single cell and/or varies between the first cell type and the second cell type at the same time point. In some embodiments, in the absence of the protease and/or the silencer effector, the payload protein reaches untuned steady state payload protein levels in the one or more cells. In some embodiments, untuned steady state payload protein levels range between a lower untuned threshold and an upper untuned threshold of an untuned expression range. In some embodiments, in the presence the protease and/or the silencer effector, the payload protein reaches tuned steady state payload protein levels in the one or more cells. In some embodiments, tuned steady state payload protein levels range between a lower tuned threshold and an upper tuned threshold of a tuned expression range. In some embodiments, at the first time point and the second time point in a single cell, the steady state levels of the payload protein remain within the tuned expression range. In some embodiments, in the first cell type and the second cell type at the same time point, the steady state levels of the payload protein remain within the tuned expression range.

In some embodiments, the lower tuned threshold and/or the upper tuned threshold of a tuned expression range can be reduced at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) by increasing the number of silencer effector binding sequences in the 3' UTR and/or increasing the degree of complementarity between the silencer effector and the one or more silencer effector binding sequences. In some embodiments, the lower tuned threshold and/or the upper tuned threshold of the tuned expression range can be increased at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) by reducing the number of silencer effector binding sequences in the 3' UTR and/or reducing the degree of complementarity between the silencer effector and the one or more silencer effector binding sequences.

Adjusting the sequence of the cut site to more or less closely approximate the canonical cut site of the protease can alter the lower tuned threshold and/or the upper tuned threshold of a tuned expression range. In some embodiments, the lower tuned threshold and/or the upper tuned threshold of a tuned expression range can be increased at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) by introducing one or more non-canonical amino acid substitutions into the cut site. In some embodiments, the lower tuned threshold and/or the upper tuned threshold of a tuned expression range can be reduced at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) by introducing one or more canonical amino acid substitutions into the cut site.

In some embodiments, the difference between the lower untuned threshold and the upper untuned threshold of the untuned expression range is greater than about two orders of magnitude. The difference between the lower tuned threshold and the upper tuned threshold of the tuned expression range can be less than about one order of magnitude. The difference between the lower tuned threshold and the upper tuned threshold of the tuned expression range can be less than about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) than the difference between the lower untuned threshold and the upper untuned threshold of the untuned expression range. In some embodiments, less than about 0.1%, less than about 1%, less than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or a number or a range between any two of these values, of the cells of a subject comprising have steady-state levels of the payload protein outside of the tuned expression range. The period of time between the introducing and/or administering steps and the cell reaching steady-state levels of the payload protein can be about 100000 hours, 10000 hours, 1000 hours, 100 hours, 50 hours, 24 hours, 8 hours, about 7 hours, about 6 hours, about 5 hours, about 4 hours, about 3 hours, about 2 hours, about 1 hour, about 30 minutes, about 15 minutes, about 10 minutes, about 5 minutes, about 1 minute, or a number or a range between any two of these values.

The payload protein can be efficacious at steady state payload protein levels within the tuned expression range. The payload protein can be inefficacious and/or toxic at steady state payload protein levels above and/or below the tuned expression range. The payload protein can be capable of inducing an immunogenic response and/or a cytokine storm at steady state payload protein levels outside the tuned expression range. Tuned steady state payload protein levels can comprise a therapeutic level of the payload protein. In some embodiments, the steady state payload protein levels remain within the tuned expression range across multiple cell types, titers of viral vector, and/or viral vector capsid types. The tuned steady state payload protein levels can be robust to tissue tropism and stochastic expression. In some embodiments of the compositions and methods, the circuits provided herein are not precisely dosage invariant but are useful to providing reduced dosage dependence and/or limiting the levels of protein expression. For example, in some embodiments, the upper tuned threshold can be at least about 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) lower than the upper untuned threshold.

There are provided, in some embodiments, methods and compositions for self-regulated gene therapy that can provide regulated expression independent of gene dosage. In some embodiments, a self-regulated gene therapy payload can provide regulated expression of a payload (e.g., MeCP2) independent of gene dosage. In some embodiments, the methods and compositions provide dosage invariance of a payload. Dosage invariance, as used herein, shall be given its ordinary meaning, and shall also refer to a lower fold change in protein output compared to gene dosage. The methods and compositions provided herein can yield and at least 1.1-fold (e.g., 1.1-fold, 1.3-fold, 1.5-fold, 1.7-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or a number or a range between any of these values) lower fold change in protein output as compared to gene dosage. In some embodiments, the methods and compositions provided here enable payload dosage invariance in vivo (e.g., in a mouse, in a human).

Some embodiments of the methods and compositions provided herein comprise a protein-level implementation. In some embodiments, the protein-level implementation comprises the following construct structure: [degron]-[Gene (e.g., payload)]-[T2A]-[protease]-[P2a]-[dosage indicator protein (e.g., mCherry)]. In some embodiments, the methods and compositions provided here enable tuning of the expression level of a payload by varying protease cleavage site sequence. The disclosed methods and compositions can function across a broad range of useful promoters, such as, but not limited to, CMV, Ef1a, and Ef1a (no intron) promoters. In some embodiments, the methods and composition operates identically in different species of cells, using different capsid variants, and/or at different viral titers.

Some embodiments of the methods and compositions provided herein comprise a miRNA-level implementation. In some embodiments, the miRNA-level implementation comprises the following construct structure: [Gene (e.g., payload)]-[miRNAtarget]-[miRNAcasette]. In some embodiments, the methods and compositions provided here enable tuning of the expression level of a payload by varying the number of miRNA target sites included in the construct. The construct can function across diverse promoters. (e.g., the same behavior across 3 promoter variants). Some embodiments of the methods and compositions enable dosage invariant gene product replacement, by including additional miRNA, on the same construct, directed specifically against the endogenous but not the ectopic gene copy. Some embodiments provided herein related to the combination of the miRNA-level and protein-level circuits provided herein (e.g., a fusion protein encoded by a transcript that also comprises miRNA binding sites and a miRNA cassette).

Some embodiments of the method and compositions provided herein comprise dosage-invariant MeCP2 gene therapy for Rett Syndrome. In some embodiments, the methods and compositions comprise a viral vector (e.g. AAV vectors, including but not limited to, AAV9 and AAV9 engineered variants for systemic delivery (e.g., AAV.PHP.eB)). The payload can comprise any gene for dosage-invariant delivery of dosage-sensitive gene products for gene therapy applications, including, but not limited to, RA1 for Smith-Magenis Syndrome; SHANK3 for Phelan-McDermid Syndrome; CLN3 for Batten Disease; NF-1 for Neurofibromitosis Type I; TP53 for Li-Fraumeni Syndrome; PFK for phosphofructokinase deficiency; and/or CD40LG for X-linked Hyper IGM disorders. Some embodiments of the method and compositions provided herein comprise a payload for treating a neurologic disease or disorder, glycogen storage disorders, hematologic disease or disorder, and any other diseases or disorders that are subject to a so-called "goldilocks" problem, wherein the delivered gene (e.g., transgene, payload) must be carefully regulated within a certain range. In some embodiments, the compositions are delivered via cerebrospinal fluid and/or CSF routes.

Some embodiments of the method and compositions provided herein comprise gene therapy applications wherein the immunogenicity of a payload needs to be reduced by avoiding unnecessary overexpression. Some embodiments comprise cell therapies (e.g., CAR-T cell therapies), wherein the methods and compositions herein enable uniform regulation of chimeric antigen receptor (CAR) expression as well as other cell therapy components in order to improve specificity and/or reduce toxicity (e.g., cytokine storm). Some embodiments of the disclosed method and compositions reduce, prevent and/or avoid overexpression toxicity in gene therapies based on protein expression. Some embodiments of the disclosed method and compositions reduce, prevent and/or avoid potential toxicity from overexpression of components in knock-down gene therapies. The provided method and compositions can comprise regulating CRE recombinase to reduce CRE-related toxicity, regulating GCaMP to reduce GCaMP-related toxicity, and/or regulating dCas9 to reduce dcas9 related genotoxicity. In some embodiments, the disclosed systems provide the same output for both ssAAV and scAAV vectors, even though the overall expression of the circuit may change. Embodiments of the methods and compositions provided herein can comprise single-stranded (ss) and self-complementary (sc) genomes. In some embodiments, the cargo can be comprise ss and/or sc cargo. The disclosed systems can be inserted into lentiviral constructs, or other viral vectors. The promoter can comprise one or more of the following: PGK, 3-phosphoglycerate kinase promoter, SV40 virus promoter; RSV virus promoter; CBA/HBA, chicken/human beta actin promoters; CMV virus promoter; UBC, ubiquitin C promoter; CAG; CBH; TRE/Tre3G; Gadph; Ef1a, elongation factor 1 alpha promoter; MeP229, MeCP2 promoter, truncated to 229 bp; MeP406, MeCP2 promoter, truncated to 406 bp; SYN, synapsin (human/otherwise) promoter; CamKIIa promoter; and MCK. The promoter can comprise one or more gene therapy promoters known in the art. In some embodiments, the functional form of the expression remains the same with single stranded AAV (ss) and self complementary AAV (sc) vectors. In some embodiments, the use of AAV (sc) vectors result in higher overall expression.

In some embodiments, the payload comprises a gene that has shown or is suspected of presenting immunogenicity issues when ectopically expressed. In some embodiments, the payload regulated by the systems provided herein is an immunogenic gene product, and can include, for example, genes provided in Table 1 (e.g., Batten's Disease/FTD). Some examples of the disclosed methods and compositions include regulating expression in antigen presenting cells and regulating expression of cell-surface exposed epitopes. In some embodiments, the methods comprise systemic delivery for the nervous system (e.g., for treatment of Rett syndrome) wherein the system can used differentially to reduce expression in pb organs such as the liver (liver toxicity) or the heart (cardiac arrest). In some embodiments of the methods and compositions disclosed herein, side-effects of systemic gene therapy (e.g., payload overexpression in heart causing cardiac arrest and/or payload overexpression in liver causing liver toxicity) are prevented by the tunable and dosage-invariant compositions and methods provided herein.

The disease or disorder can comprise a MECP2-related disorder selected from the group comprising Classic Rett Syndrome, MECP2-related Severe Neonatal Encephalopathy, PPM-X Syndrome, or any combination thereof. The disease or disorder can be a blood disease, an immune disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof.

The disease or disorder can comprise a neurological disease or disorder. The neurological disease or disorder can comprise Alzheimer's disease, Creutzfeld-Jakob's syndrome/disease, bovine spongiform encephalopathy (BSE), prion related infections, diseases involving mitochondrial dysfunction, diseases involving β-amyloid and/or tauopathy, Down's syndrome, hepatic encephalopathy, Huntington's disease, motor neuron diseases, amyotrophic lateral sclerosis (ALS), olivoponto-cerebellar atrophy, post-operative cognitive deficit (POCD), systemic lupus erythematosus, systemic clerosis, Sjogren's syndrome, Neuronal Ceroid Lipofuscinosis, neurodegenerative cerebellar ataxias, Parkinson's disease, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, convulsions, epileptic convulsions, epilepsy, temporal lobe epilepsy, myoclonic epilepsy, tinnitus, dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, addiction, anxiety disorders, panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimer's disease, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, memory loss, stress, bipolar manic-depressive disorder, drug tolerance, drug tolerance to opioids, movement disorders, fragile-X syndrome, irritable bowel syndrome (IBS), migraine, multiple sclerosis (MS), muscle spasms, pain, chronic pain, acute pain, inflammatory pain, neuropathic pain, posttraumatic stress disorder (PTSD), schizophrenia, spasticity, Tourette's syndrome, eating disorders, food addiction, binge eating disorders, agoraphobia, generalized anxiety disorder, obsessive-compulsive disorder, panic disorder, social phobia, phobic disorders, substance-induced anxiety disorder, delusional disorder, schizoaffective disorder, schizophreniform disorder, substance-induced psychotic disorder, hypertension, or any combination thereof.

The disease or disorder can be an expression-sensitive disease or disorder. An expression-sensitive disease or disorder can be characterized by decreased expression of one or more proteins, wherein ectopic overexpression of said one or more proteins at a steady state level beyond the upper tuned threshold causes cellular toxicity and/or disease. The disease or disorder can be a disease or disorder provided in Table 1. Table 1 provides an exemplary list of so-called "Goldilocks" diseases and disorders wherein disease phenotypes are attributable to decreased expression of genes but also exhibit cellular toxicity or outright disease when over-expressed. The methods and compositions provided herein are surprisingly capable of treating or preventing said diseases and disorders via the tunable and robust expression means provided herein. In some embodiments, the payload gene comprises any of the genes provided in Table 1.

TABLE 1

EXPRESSION-SENSITIVE DISEASES AND DISORDERS

| Disorder Class | Disorder | Gene Implicated in Disease |
|---|---|---|
| Neurodevelopmental Syndromic Disorders | Rett Syndrome | MeCP2 |
| | Smith-Magenis Syndrome | RAI1 |
| | Phelan-McDermid Syndrome | SHANK3 |
| | Cornelia de Lange Syndrome and other NIPBL related disorders | NIPBL |
| | DRK1A, KAT6A and related disorders of severe intellectual disability | DRK1A, KAT6A |

TABLE 1-continued

EXPRESSION-SENSITIVE DISEASES AND DISORDERS

| Disorder Class | Disorder | Gene Implicated in Disease |
|---|---|---|
| | Chromosome 2Q37 Deletion Syndrome and other HDAC4 Related Disorders | HDAC4 |
| | Angelman Syndrome | UBE3A |
| | Kleefstra Syndrome | EHMT1 and other genes encoded on chromosome 9q34.3 |
| | Joubert Syndrome and other NPHP1 Related Disorders | NPHP1 |
| | Williams Syndrome | LIMK1 and other genes encoded on chromosome 7q11.23 |
| Proliferative/Cancer Disorders | Neurofibromatosis Type 1 | NF1 |
| | Li-Fraumeni syndrome and similar p53-related cancer syndromes | P53 |
| Glycogen Storage Disorders | Phosphofructokinase Deficiency | PFK |
| Hematologic/Immune Disorders | X-linked Hyper IgM Syndrome and similar primary immunodeficiency disorders | CD40L |
| | Triosephosphate isomerase deficiency | TPI1 |
| Endocrine Disorders | Kallman Syndrome | FGFR1 and related genes |
| | Aromatase Deficiency | CYP19A1 |
| Other Neuropsychiatric Disorders | Batten Disease, Frontotemporal Dementia and other neurodegenerative disorders related to loss of progranulin | PGRN |
| | Cholinergic Receptor Nicotinic Alpha 7 Subunit Related Disorders | CHRNA7 |
| | Hereditary Neuropathy with liability to Pressure Palsies | PMP22 |

Promoters

The promoters of the nucleic acids provided herein can vary depending on the embodiment. The promoter can comprise a ubiquitous promoter. The ubiquitous promoter can be selected from the group comprising a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof.

In some embodiments, one or more cells of a subject (e.g., a human) comprise an endogenous version of the payload gene, and the promoter can comprise or can be derived from the promoter of the endogenous version. The promoter can comprise at least about 25% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, or a number or a range between any two of these values) homology to the promoter of the endogenous version of the payload gene. The promoter can be a methyl CpG binding protein 2 (MeCP2) promoter or a derivative thereof (e.g., a MeCP2 promoter truncated to about 229 bp and/or a MeCP2 promoter truncated to about 406 bp). The promoter can comprise an intronic sequence. The promoter can comprise a bidirectional promoter and/or an enhancer (e.g., a CMV enhancer).

The promoter can be an inducible promoter (e.g., a tetracycline responsive promoter, a TRE promoter, a Tre3G promoter, an ecdysone responsive promoter, a cumate responsive promoter, a glucocorticoid responsive promoter, and estrogen responsive promoter, a PPAR-γ promoter, and/or an RU-486 responsive promoter). The promoter can comprise a tissue-specific promoter and/or a lineage-specific promoter. The tissue specific promoter can be a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. The tissue specific promoter can be a neuron-specific promoter (e.g., a synapsin-1 (Syn) promoter, a CaMKIIa promoter, a calcium/calmodulin-dependent protein kinase II a promoter, a tubulin alpha I promoter, a neuron-specific enolase promoter, a platelet-derived growth factor beta chain promoter, TRPV1 promoter, a $Na_v1.7$ promoter, a $Na_v1.8$ promoter, a $Na_v1.9$ promoter, or an Advillin promoter). The tissue specific promoter can be a muscle-specific promoter (e.g., a creatine kinase (MCK) promoter).

In some embodiments, payload expression can be gated by a drug/small molecule. In some embodiments, the method can comprise an inducible promoter or a repressible promoter. The method can comprise administering one or more doses (e.g., a higher starting dose and a lower maintenance dose) of an agent that exerts an effect on the promoter (e.g., an inducer of said inducible promoter). In some such embodiments, only induce payload expression at a certain time point or expression profile, such as, for example, cases where a starting higher does versus a longer term maintenance dose is needed. Some embodiments of the compositions, methods, and systems provided herein can comprise one or more components of an transactivator rtTA (reverse tetracycline-controlled transactivator) system. By using an rrTA system, expression of the gene of interest (e.g. payload) can be further regulated by an inducible system whereby only when a small molecule doxycycline is added, the IFFL regulated construct is expressed.

The compositions provided herein can comprise a tetracycline-on (Tet-On) system. As an example, tetracycline-on (Tet-On) systems can use a reverse tetracycline transactivator (rtTA) to induce gene expression. Reverse tetracycline transactivators (rtTAs) comprise a mutant tetracycline repressor DNA binding protein (TetR) and a transactivation domain. These transactivators can be activated in the presence of a tetracycline (e.g., doxycycline) and subsequently bind to promoters comprising a tetracycline-responsive element (TRE) to induce gene expression. A TRE comprises at least one Tet operator (Tet-O) sequence (e.g., multiple repeats of Tel-0 sequences) and may be located upstream of a minimal promoter (e.g., minimal promoter sequence derived from the human cytomegalovirus (hCMV) immediate-early promoter). A "Tet-On" system, as used herein, is a type of inducible system that is capable of inducing expression of a particular payload gene in the presence of tetracycline (e.g., doxycycline (DOX)). In certain embodiments, a Tet-On system comprises a tetracycline-responsive promoter operably linked to a payload gene (e.g., a therapeutic sequence, a gene-targeting nucleic acid, and/or a nucleic acid encoding a protein) and a reverse tetracycline-controlled transactivator (rtTA). The expression cassette encoding a tetracycline-responsive promoter (e.g., a promoter comprising a TRE, including TRE3G, P tight, and TRE2) and a reverse tetracycline-controlled transactivator may be encoded on the same vector or be encoded on separate vectors. In some embodiments, the promoter comprises Tet Response Element (TRE). Tetracycline-dependent promoters can be constructed by placing a TRE upstream of a minimal promoter.

A "reverse tetracycline transactivator" ("rtTA"), as used herein, shall be given its ordinary meaning, and shall also refer an inducing agent that binds to a TRE promoter (e.g., a TRE3G, P tight, or TRE2 promoter) in the presence of tetracycline (e.g., doxycycline) and is capable of driving expression of a payload gene that is operably linked to the TRE promoter. rtTAs generally comprise a mutant tetracycline repressor DNA binding protein (TetR) and a transactivation domain. Any suitable transactivation domain may be used. Non-limiting examples include VP64, P65, RTA, and MPH MS2-P65-HSF1. In some embodiments, a rtTA of the present disclosure comprises at least 1, 2, 3, 4, 5, 6, 7, 8, 9, 10, 11, 12, 13, 14, 15, 16, 17, 18, 19, 20, 30, 40, 50, 60, 70, 80, 90, or 100 transactivation domains. The mutant TetR domain is capable of binding to a TRE promoter when bound to tetracycline.

The methods and compositions provided herein can comprise a tetracycline repressor. The term "tetracycline repressor" or "TetR" shall be given its ordinary meaning, and shall also refer to a protein that is capable of binding to a Tet-0 sequence (e.g., a Tet-0 sequence in a TRE) in the presence of tetracycline (e.g., doxycycline) and prevents binding of rtTA (e.g., rtTA3, rtTA4, or variants thereof) in the absence of tetracycline (e.g., doxycycline). TetRs prevent gene expression from promoters comprising a TRE in the absence of tetracycline (e.g., doxycycline). In the presence of tetracycline, TetRs cannot bind promoters comprising a TRE, and TetR cannot prevent transcription.

The term "promoter" shall be given its ordinary meaning, and shall also refer to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific, or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation of that sequence, expression of that sequence, or a combination thereof.

A promoter may promote ubiquitous expression or tissue-specific expression of an operably linked nucleic acid sequence from any species, including humans. In some embodiments, the promoter is a eukaryotic promoter. Non-limiting examples of eukaryotic promoters include TDH3, PGK1, PKC1, TDH2, PYK1, TPI1, AT1, CMV, EF1a, SV40, PGK1 (human or mouse), Ubc, human beta actin, CAG, TRE, UAS, Ac5, Polyhedrin, CaMKIIa, GAL1, GAL 10, TEF, GDS, ADH1, CaMV35S, Ubi, Hl, and U6, as would be known to one of ordinary skill in the art.

Non-limiting examples of ubiquitous promoters include tetracycline-responsive promoters (under the relevant conditions), CMV, EF1 alpha, a SV40 promoter, PGK1, Ubc, CAG, human beta actin gene promoter, and a promoter comprising an upstream activating sequence (UAS). In certain embodiments, the promoter is a mammalian promoter. Non-limiting examples of tissue-specific promoters include brain-specific, liver-specific, muscle-specific, nerve cell-specific, lung-specific, heart-specific, bone-specific, intestine-specific, skin-specific promoters, brain-specific promoters, and eye-specific promoters.

Non-limiting examples of constitutive promoters include CP1, CMV, EF1 alpha, SV40, PGK1, Ubc, human beta actin, beta tubulin, CAG, Ac5, polyhedrin, TEF1, GDS, CaM3 5S, Ubi, Hl, and U6.

An "inducible promoter" shall be given its ordinary meaning, and shall also refer one that is characterized by initiating or enhancing transcriptional activity when in the presence of, influenced by, or contacted by an inducing agent. An inducing agent may be endogenous or a normally exogenous condition, compound, agent, or protein that contacts an engineered nucleic acid in such a way as to be active in inducing transcriptional activity from the inducible promoter. In certain embodiments, an inducing agent is a tetracycline-sensitive protein (e.g., rtTA).

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (tetRTetR), a tetracycline operator sequence (tetO), and a tetracycline transactivator fusion protein (tTA), and a tetracycline operator sequence (tetO) and a reverse tetracycline transactivator fusion protein (rtTA)), steroid-regulated promoters (e.g., promoters based on the rat glucocorticoid receptor, human estrogen receptor, moth ecdysone receptors, and promoters from the steroid/retinoid/thyroid 25 receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters.

Payloads

In some embodiments, the payload protein comprises a disease-associated protein, wherein aberrant expression of the disease-associated protein correlates with the occurrence and/or progression of the disease. The payload protein can comprise a protein associated with an expression-sensitive disease or disorder as provided in Table 1. The payload protein can comprise methyl CpG binding protein 2 (MeCP2), DRK1A, KAT6A, NIPBL, HDAC4, UBE3A, EHMT1, one or more genes encoded on chromosome 9q34.3, NPHP1, LIMK1 one or more genes encoded on chromosome 7q11.23, P53, TPI1, FGFR1 and related genes, RA1, SHANK3, CLN3, NF-1, TP53, PFK, CD40L, CYP19A1, PGRN, CHRNA7, PMP22, CD40LG, derivatives thereof, or any combination thereof.

The payload protein can comprise fluorescence activity, polymerase activity, protease activity, phosphatase activity, kinase activity, SUMOylating activity, deSUMOylating activity, ribosylation activity, deribosylation activity, myristoylation activity demyristoylation activity, or any combination thereof.

The payload protein can comprise nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, adenylation activity, deadenylation activity, or any combination thereof.

The payload protein can comprise a programmable nuclease. The programmable nuclease can be selected from the group comprising: SpCas9 or a derivative thereof, VRER, VQR, EQR SpCas9; xCas9-3.7; eSpCas9; Cas9-HF1; HypaCas9; evoCas9; HiFi Cas9; ScCas9; StCas9; NmCas9; SaCas9; CjCas9; CasX; Cas9 H940A nickase; Cas12 and derivatives thereof, dcas9-APOBEC1 fusion, BE3, and dcas9-deaminase fusions; dcas9-Krab, dCas9-VP64, dCas9-Tet1, and dcas9-transcriptional regulator fusions; Dcas9-fluorescent protein fusions; Cas13-fluorescent protein fusions; RCas9-fluorescent protein fusions; Cas13-adenosine deaminase fusions. The programmable nuclease can comprise a zinc finger nuclease (ZFN) and/or transcription activator-like effector nuclease (TALEN). The programmable nuclease can comprise Streptococcus pyogenes Cas9 (SpCas9), Staphylococcus aureus Cas9 (SaCas9), a zinc finger nuclease, TAL effector nuclease, meganuclease, MegaTAL, Tev-m TALEN, MegaTev, homing endonuclease, Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c3, Cas12a, Cas12b, Cas12c, Cas12d, Cas12e, Cas13a, Cas13b, Cas13c, derivatives thereof, or any combination thereof. In some embodiments, the nucleic acid further comprises a polynucleotide encoding (i) a targeting molecule and/or (ii) a donor nucleic acid. The composition can comprise (i) a targeting molecule or a nucleic acid encoding the targeting molecule and/or (ii) a donor nucleic acid or a nucleic acid encoding the donor nucleic acid. The targeting molecule can be capable of associating with the programmable nuclease. The targeting molecule can comprise single strand DNA or single strand RNA. The targeting molecule can comprise a single guide RNA (sgRNA). The programmable nuclease can comprise a zinc finger nuclease, TAL effector nuclease, meganuclease, MegaTAL, Tev-m TALEN, MegaTev, homing endonuclease, derivatives thereof, or any combination thereof. The targeting molecule can be capable of associating with the programmable nuclease. The targeting molecule can comprise single strand DNA or single strand RNA. The targeting molecule can comprise a single guide RNA (sgRNA). The targeting molecule can comprise a synthetic nucleic acid.

In some embodiments, the payload comprises one or more programmable nucleases disclosed in Table 2. In some embodiments, the payload comprises one or more prime editors. There are provided, in some embodiments, methods of gene editing that fulfill the gene purpose and/or regulation purpose set forth in Table 2.

TABLE 2

| PROGRAMMABLE NUCLEASES | | |
|---|---|---|
| Gene | Gene Purpose | Regulation Purpose |
| SpCas9 | Genome Engineering, gene editing | Reduce off-target nuclease activity or immunogenicity |
| mutations thereof: | | |
| VRER, VQR, and EQR SpCas9 xCas9-3.7 eSpCas9 Cas9-HF1 HypaCas9 evoCas9 HiFi Cas9 | Genome Engineering, gene editing | Reduce off-target nuclease activity or immunogenicity |
| Other Cas9 species: | | |
| ScCas9 StCas9 NmCas9 SaCas9 CjCas9 CasX | Genome Engineering, gene editing | Reduce off-target nuclease activity or immunogenicity |

TABLE 2-continued

PROGRAMMABLE NUCLEASES

| Gene | Gene Purpose | Regulation Purpose |
|---|---|---|
| Cas9 H940A nickase | Prime editing | Reduce off-target editing and immunogenicity. |
| Cas12 and mutations | Multiplex gene editing | Reduce off-target nuclease activity or immunogenicity |
| dcas9-APOBEC1 fusion, BE3, other dcas9-deaminase fusions | CRISPR base editing | Reduce off-target base editing (which is a significant unsolved problem) or immunogenicity |
| dcas9-Krab, dCas9-VP64, dCas9-Tet1, and other dcas9-transcriptional regulator fusion | activate/repress transcription, modify epigenetic state | Reduce off-target, decrease immunogenicity. |
| Dcas9-fluorescent protein fusions | Imaging and tracking genomic loci and chromatin dynamics | Increase signal to noise ratio |
| Cas13-fluorescent protein fusions | RNA imaging and tracking | Increase signal to noise ratio |
| RCas9-fluorescent protein fusions | RNA imaging | Increase signal to noise ratio |
| Cas13-adenosine deaminase fusions | RNA editing | reduce off-target and immunogenicity |

The payload protein can comprise a chimeric antigen receptor. The methods and compositions provided herein find use in cell therapies (e.g., adoptive therapies). Aspects of the invention accordingly involve the adoptive transfer of immune system cells, such as T cells, specific for selected antigens, such as tumor associated antigens. Various strategies may, for example, be employed to genetically modify T cells by altering the specificity of the T cell receptor (TCR) for example by introducing payloads comprising new TCR a and b chains with selected peptide specificity. As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described. In some embodiments, the invention described herein relates to a method for adoptive immunotherapy, comprising (1) knock-in an exogenous gene encoding a chimeric antigen receptor (CAR) or a T-cell receptor (TCR), (2) knock-out or knock-down expression of an immune checkpoint receptor, (3) knock-out or knock-down expression of an endogenous TCR, (4) knock-out or knock-down expression of a human leukocyte antigen class I (HLA-I) proteins, and/or (5) knock-out or knock-down expression of an endogenous gene encoding an antigen targeted by an exogenous CAR or TCR.

The payload protein can be associated with an agricultural trait of interest selected from the group consisting of increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance, increased biomass production, male sterility, or any combination thereof.

The payload protein can be associated with a biological manufacturing process selected from the group comprising fermentation, distillation, biofuel production, production of a compound, production of a polypeptide, or any combination thereof.

In some embodiments, the polynucleotide further encodes one or more secondary proteins (e.g., secondary payload proteins). The secondary payload proteins can comprise any of the payloads described herein. The payload protein and the one or more secondary proteins can be expressed as a fusion protein (and can be separated by one or more self-cleaving peptides). The 3'UTR of the transgene(s) encoding the one or more secondary proteins can comprise one or more silencer effector binding sequences. The payload protein and the one or more secondary proteins can be expressed on separate payload transcripts.

Protein-level circuits that can be expressed on a single transcript are a growing trend in bioengineering. The behavior of protein-level circuits will depend on the expression levels of their individual components. IFFLs can help guarantee correct functioning of these circuits by maintaining the stoichiometric ratios of circuit components in variable environments, including by regulating the circuit as a whole if it is on a single transcript.

The payload protein and the one or more secondary proteins can be encoded on a single transcript, and wherein translations of the payload protein and the one or more secondary proteins can be each driven by a separate internal ribosome entry site. The sequences of the internal ribosome entry sites can be identical or different.

The payload protein and the one or more secondary proteins can comprise a synthetic protein circuit. Synthetic biology allows for rational design of circuits that confer new functions in living cells. Many natural cellular functions are implemented by protein-level circuits, in which proteins specifically modify each other's activity, localization, or stability. Synthetic protein circuits have been described in, Gao, Xiaojing J., et al. "Programmable protein circuits in living cells." *Science* 361.6408 (2018): 1252-1258; and PCT Application Publication No. WO 2019/147478; the content of each of these, including any supporting or supplemental information or material, is incorporated herein by reference in its entirety. The methods and compositions provided herein can express, for example, synthetic protein circuits that respond to inputs only above or below a certain tunable threshold concentration, such as those provided in U.S. patent application Ser. No. 16/738,664, published as US Patent Publication No. 2020/0277333, the content of which is incorporated herein by reference in its entirety. The methods and compositions provided herein can express, for example, synthetic protein circuits comprising one or more synthetic protein circuit design components and/or concepts of U.S. application Ser. No. 16/556,063, filed on Aug. 29, 2019, the content of which is incorporated herein by reference in its entirety.

Disclosed herein are nucleic acids comprising a polynucleotide encoding one or more payload genes. As disclosed herein, the payload gene is operatively linked with appropriate regulatory elements in some embodiments. The one or more payload genes of the nucleic acid can comprise a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. The one or more payload genes of the nucleic acid can comprise one or more synthetic protein circuit components. The one or more payload genes of the nucleic acid can comprise can entire synthetic protein circuit comprising one or more synthetic protein circuit components. The one or more payload genes of the nucleic acid can comprise two or more synthetic protein circuits.

The payload protein can be any protein, including naturally-occurring and non-naturally occurring proteins. Examples of payload protein include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof, erythropoietin (EPO) and variants thereof, insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof, clotting factors and variants thereof, cystic fibrosis transmembrane conductance regulator (CFTR) and variants thereof; and interferons and variants thereof.

In some embodiments, the payload protein is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as β-glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of payload protein include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the payload protein is an active fragment of a protein, such as any of the aforementioned proteins. In some embodiments, the payload protein is a fusion protein comprising some or all of two or more proteins. In some embodiments a fusion protein can comprise all or a portion of any of the aforementioned proteins.

In some embodiments, the payload protein is a multi-subunit protein. For examples, the payload protein can comprise two or more subunits, or two or more independent polypeptide chains. In some embodiments, the payload protein can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody.

In some embodiments, the payload gene encodes a pro-survival protein (e.g., Bcl-2, Bcl-XL, Mcl-1 and A1). In some embodiments, the payload gene encodes a apoptotic factor or apoptosis-related protein such as, for example, AIF, Apaf (e.g., Apaf-1, Apaf-2, and Apaf-3), oder APO-2 (L), APO-3 (L), Apopain, Bad, Bak, Bax, Bcl-2, Bcl-xL, Bcl-xs, bik, CAD, Calpain, Caspase (e.g., Caspase-1, Caspase-2, Caspase-3, Caspase-4, Caspase-5, Caspase-6, Caspase-7, Caspase-8, Caspase-9, Caspase-10, and Caspase-11), ced-3, ced-9, c-Jun, c-Myc, crm A, cytochrom C, CdR1, DcR1, DD, DED, DISC, DNA-PKcs, DR3, DR4, DR5, FADD/ MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, INK, Lamin A/B, MAP, MCL- 1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the payload gene encodes a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1 L, TBX3b, SV40 large T, hTERT, miR-291, miR-294, miR-295, or any combinations thereof. In some embodiments, the payload gene encodes a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the payload gene encodes a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, TypIII repeat extra domain A of fibronectin; the receptors, including IL-1 RI, TLR1, TLR2, TLR3, TLR4, TLR5, TLR6, TLR7, TLR8, TLR9, TLR10, TLR11; the signal transducers including components of the Small-GTPases signaling (RhoA, Ras, Rac1, Cdc42 etc.), components of the PIP signaling (PI3K, Src-Kinases, etc.), components of the MyD88-dependent signaling (MyD88, IRAK1, IRAK2, etc.), components of the MyD88-independent signaling (TICAM1, TICAM2 etc.); activated transcription factors including e.g. NF-κB, c-Fos, c-Jun, c-Myc; and induced target genes including e.g. IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

In some embodiments, the payload gene encodes immunogenic material capable of stimulating an immune response (e.g., an adaptive immune response) such as, for example, antigenic peptides or proteins from a pathogen. The expression of the antigen may stimulate the body's adaptive immune system to provide an adaptive immune response. Thus, it is contemplated that some embodiments the nucleic acids provided herein can be employed as vaccines for the prophylaxis or treatment of infectious diseases (e.g., as vaccines).

As described herein, the nucleotide sequence encoding the payload protein can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host (e.g., a mammal).

The degree of payload gene expression in the target cell can vary. For example, in some embodiments, the payload gene encodes a payload protein. The amount of the payload protein expressed in the subject (e.g., the serum of the subject) can vary. For example, in some embodiments the protein can be expressed in the serum of the subject in the amount of at least about 9 μg/ml, at least about 10 μg/ml, at least about 50 μg/ml, at least about 100 μg/ml, at least about 200 g/ml, at least about 300 μg/ml, at least about 400 μg/ml, at least about 500 μg/ml, at least about 600 μg/ml, at least about 700 μg/ml, at least about 800 μg/ml, at least about 900 μg/ml, or at least about 1000 μg/ml. In some embodiments, the payload protein is expressed in the serum of the subject in the amount of about 9 g/ml, about 10 μg/ml, about 50 μg/ml, about 100 μg/ml, about 200 μg/ml, about 300 μg/ml, about 400 μg/ml, about 500 μg/ml, about 600 μg/ml, about 700 μg/ml, about 800 μg/ml, about 900 μg/ml, about 1000 μg/ml, about 1500 μg/ml, about 2000 μg/ml, about 2500 μg/ml, or a range between any two of these values. A skilled artisan will understand that the expression level in which a payload protein is needed for the method to be effective can vary depending on non-limiting factors such as the particular payload protein and the subject receiving the treatment, and an effective amount of the protein can be readily determined by a skilled artisan using conventional methods known in the art without undue experimentation.

A payload protein encoded by a payload gene can be of various lengths. For example, the payload protein can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the payload protein is at least about 480 amino acids in length. In some embodiments, the payload protein is at least about 500 amino acids in length. In some embodiments, the payload protein is about 750 amino acids in length.

The payload genes can have different lengths in different implementations. The number of payload genes can be different in different embodiments. In some embodiments, the number of payload genes in a nucleic acid can be, or can be about, 1, 2, 3, 4, 5, 6, 7, 8, 9, 10, 11, 12, 13, 14, 15, 16, 17, 18, 19, 20, 21, 22, 23, 24, 25, or a number or a range between any two of these values. In some embodiments, the number of payload genes in a nucleic acid can be at least, or can be at most, 1, 2, 3, 4, 5, 6, 7, 8, 9, 10, 11, 12, 13, 14, 15, 16, 17, 18, 19, 20, 21, 22, 23, 24, 25. In some embodiments, a payload genes is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, 10000, or a number or a range between any two of these values, nucleotides in length. In some embodiments, a payload gene is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3250, 3500, 3750, 4000, 4250, 4500, 4750, 5000, 5500, 6000, 6500, 7000, 7500, 8000, 8500, 9000, 9500, or 10000 nucleotides in length.

The payload can be an inducer of cell death. The payload can be induce cell death by a non-endogenous cell death pathway (e.g., a bacterial pore-forming toxin). In some embodiments, the payload can be a pro-survival protein. In some embodiments, the payload is a modulator of the immune system. The payload can activate an adaptive immune response, and innate immune response, or both. In some embodiments, the payload gene encodes immunogenic material capable of stimulating an immune response (e.g., an adaptive immune response) such as, for example, antigenic peptides or proteins from a pathogen. The expression of the antigen may stimulate the body's adaptive immune system to provide an adaptive immune response. Thus, it is contemplated that some embodiments the compositions provided herein can be employed as vaccines for the prophylaxis or treatment of infectious diseases (e.g., as vaccines). The payload protein can comprise a CRE recombinase, GCaMP, a cell therapy component, a knock-down gene therapy component, a cell-surface exposed epitope, or any combination thereof.

Examples of payload genes include a sequence associated with a signaling biochemical pathway, e.g., a signaling biochemical pathway-associated gene or polynucleotide (e.g., a signal transducer). In some embodiments, the methods and compositions disclosed herein comprise knockdown of an endogenous signal transducer accompanied by tuned expression of a payload protein comprising an appropriate version of signal transducer. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. Signal transducers can be can be associated with one or more diseases or disorders. In some embodiments, a disease or disorder is characterized by an aberrant signaling of one or more signal transducers disclosed herein. In some embodiments, the activation level of the signal transducer correlates with the occurrence and/or progression of a disease or disorder. The activation level of the signal transducer can be directly responsible or indirectly responsible for the etiology of the disease or disorder. Non-limiting examples of signal transducers, signal transduction pathways, and diseases and disorders characterized by aberrant signaling of said signal transducers are listed in Tables 3-5. In some embodiments, the methods and compositions disclosed herein prevent or treat one or more of the diseases and disorders listed in Tables 3-5. In some embodiments, the payload comprises a replacement version of the signal transducer. In some embodiments, the methods and compositions further comprise knockdown of the corresponding endogenous signal transducer. The payload can comprise the product of a gene listed in listed in Tables 3-5. In some embodiments, the payload ameliorates a disease or disorder characterized by an aberrant signaling of one or more signaling transducers. In some embodiments, the payload diminishes the activation level of one or more signal transducers (e.g., signal transducers with aberrant overactive signaling, signal transducers listed in Tables 3-5). In some embodiments, the payload increases the activation level of one or more signal transducers (e.g., signal transducers with aberrant underactive signaling). In some such embodiments, the payload can modulate the abundance, location, stability, and/or activity of activators or repressors of said signal transducers.

TABLE 3

DISEASES AND DISORDERS OF INTEREST

| Diseases/Disorders | Genes |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado- Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |

TABLE 3-continued

DISEASES AND DISORDERS OF INTEREST

| Diseases/Disorders | Genes |
| --- | --- |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL- 17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 4

SIGNAL TRANSDUCERS

| | |
| --- | --- |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5); Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), 11-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5); Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |

TABLE 4-continued

| SIGNAL TRANSDUCERS | |
|---|---|
| Muscular/ Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Ocular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 5

| SIGNAL TRANSDUCTION PATHWAYS | |
|---|---|
| Pathway | Genes |
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |

TABLE 5-continued

SIGNAL TRANSDUCTION PATHWAYS

| Pathway | Genes |
|---|---|
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |

TABLE 5-continued

SIGNAL TRANSDUCTION PATHWAYS

| Pathway | Genes |
|---|---|
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BA$\chi$; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAKI; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |

TABLE 5-continued

SIGNAL TRANSDUCTION PATHWAYS

| Pathway | Genes |
|---|---|
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; MAP2K1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAχ; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAFI; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |

TABLE 5-continued

SIGNAL TRANSDUCTION PATHWAYS

| Pathway | Genes |
| --- | --- |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |

TABLE 5-continued

SIGNAL TRANSDUCTION PATHWAYS

| Pathway | Genes |
|---|---|
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |

TABLE 5-continued

SIGNAL TRANSDUCTION PATHWAYS

| Pathway | Genes |
| --- | --- |
| Lysine Degradation | ALDH1A1 |
| Pain/Taste | TRPM5; TRPA1 |
| Pain | TRPM7; TRPC5; TRPC6; TRPC1; Cnr1; cm2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Bm3a); Numb; Reln |

Viral Vectors

There are provided, in some embodiments, viral vectors. The viral vector can be an RNA viral vector. The polynucleotide can be derived from a positive sense RNA virus, a negative sense RNA virus, an ambisense RNA virus, or any combination thereof. The polynucleotide can be derived from a single-stranded RNA virus. The polynucleotide can be derived from a negative-strand RNA virus. The polynucleotide can be derived from one or more negative-strand RNA viruses of the order Mononegavirales. The nucleoprotein (N), phosphoprotein (P), matrix protein (M), and/or RNA-dependent RNA polymerase (L) can be derived from one or more negative-strand RNA viruses of the order Mononegavirales (e.g., a bornaviridae virus, a filoviridae virus, a nyamiviridae virus, a paramyxodiridae virus, a rhabdoviridae virus, or any combination thereof). The Mononegavirales virus can comprise rabies virus, sendai virus, vesicular stomatitis virus, or any combination thereof. A Mononegavirales-based viral vector can comprise one or more attenuating mutations. In some embodiments, the one or more negative-strand RNA viruses of the order Monon-egavirales can comprise an attenuated rabies virus strain (e.g., CVS-N2c, CVS-B2c, DRV-4, RRV-27, SRV-16, ERA, CVS-11, SAD B19, SPBN, SN-10, SN10-333, PM, LEP, SAD, or any combination thereof).

Viral vectors and methods of using are provided in PCT Application Publication No. WO2020/210655A1 and U.S. Patent Publication No. 2020/0165576, the content of each of which is incorporated herein by reference in its entirety. The viral vector can be modified so that the viral vector is targeted to a particular target environment of interest such as central nervous system, and to enhance tropism to the target environment of interest (e.g, CNS tropism). In some embodiments, the viral vector is AAV-CAP.B22. Broad gene expression throughout the mouse and marmoset brain after intravenous delivery of engineered AAV capsids has been described in Flytzanis et al. ("Broad gene expression throughout the mouse and marmoset brain after intravenous delivery of engineered AAV capsids" biorxiv, 2020), the content of which is incorporated herein by reference in its entirety.

Exemplary viral vectors that can be used in the methods, compositions, systems and kits described herein include those provided in US 20200071723A1, the content of which is incorporated herein by reference in its entirety. In some embodiments, the vector can comprise an adenovirus vector, an adeno-associated virus vector (AAV), an Epstein-Barr virus vector, a Herpes virus vector, an attenuated HIV vector, a retroviral vector, a vaccinia virus vector, or any combination thereof. In some embodiments, the vector can comprise an RNA viral vector. In some embodiments, the vector can be derived from one or more negative-strand RNA viruses of the order Mononegavirales. In some embodiments, the vector can be a rabies viral vector. Many such vectors useful for transferring exogenous genes into target mammalian cells are available. The vectors may be episomal, e.g. plasmids, virus-derived vectors such as cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Retroviral vectors can be "defective", i.e. unable to produce viral proteins required for productive infection. Replication of the vector can require growth in the packaging cell line. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

In some embodiment, the vectors can include a regulatory sequence that allows, for example, the translation of multiple proteins from a single mRNA. Non-limiting examples of such regulatory sequences include internal ribosome entry site (IRES) and 2A self-processing sequence. In some embodiments, the 2A sequence is a 2A peptide site from foot-and-mouth disease virus (F2A sequence). In some embodiments, the F2A sequence has a standard furin cleavage site. In some embodiments, the vector can also comprise regulatory control elements known to one of skill in the art to influence the expression of the RNA and/or protein products encoded by the polynucleotide within desired cells of the subject. In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an ration and the splice donor and splice acceptor sequences that regulate the splicing of said intron. Another example of a regulatory element is a transcription termination signal and/or a polyadenylation sequence.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to, the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1 alpha; or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide m response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present: the greater the amount of signal or stimuli, the greater the increase or decrease in expression.

Methods of Detecting and Monitoring

In some embodiments, the methods and compositions provided herein are useful in detecting a disease or disorder and/or monitoring the progression of a disease or disorder. As used herein, the term "diagnostic" refers identifying the presence or absence of or nature of a disease or disorder. Such detection methods can be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo. The payload protein can comprise a diagnostic agent. The payload protein can comprise a diagnostic contrast agent. The diagnostic agent can comprise green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, mruby3, rsCherry, rsCherryRev, derivatives thereof, or any combination thereof.

In some embodiments, the payload protein encodes a diagnostic agent. In some embodiments, the diagnostic agent aids in the identification of a unique cell type and/or a unique cell state. The diagnostic agent can be a molecule capable of detection, including, but not limited to, fluorescers, chemiluminescers, bioluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. For example, the diagnostic agent may comprise, in some embodiments, a fluorescent protein, such as, but not limited to, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, or any combination thereof. In some embodiments, the expression, stability, and/or activity (e.g., fluorescence) of the diagnostic agent is configured to be responsive to a disease state or a disorder state.

In some embodiments, the diagnostic agent aids in the identification of a unique cell type and/or a unique cell state. The unique cell type and/or a unique cell state can comprise lesions (e.g. tumors, infected cells). Detection and/or imaging of the diagnostic agent can enable a clinician to intraoperatively, laparoscopically, intravascularly or endoscopically detect said lesions. In some such embodiments, discrimination between lesions (e.g. tumors) and non-lesions (e.g. non-tumor tissue) is enhanced by the detection and/or imaging of the diagnostic agent. In some embodiments, detection and/or imaging of the diagnostic agent can enable a clinician to accurately locate lesions in a patient and thereby aid resection, irradiation, biopsy and/or lesion removal. In some embodiments, detection and/or imaging of the diagnostic agent aids the detection of non-malignant pathological lesions, such as, an infarct, including myocardial, atherosclerotic plaque, clot, including thrombosis, pulmonary embolism, infectious or inflammatory lesion, non-tumorous or noninfectious inflammation, or hyperplasia. The detection and/or imaging of the diagnostic agent may also be used to detect various stages of progression or severity of disease (e.g., benign, premalignant, and malignant breast lesions, tumor growth, or metastasis). The detection and/or imaging of the diagnostic agent may also be used to detect the response of the disease to prophylactic or therapeutic treatments or other interventions. The detection and/or imaging of the diagnostic agent can furthermore be used to help the medical practitioner in determining prognosis (e.g., worsening, status-quo, partial recovery, or complete recovery) of the patient, and the appropriate course of action.

Detection and/or imaging of the diagnostic agent can be performed, for example, using an ultrasound scanner, a magnetic resonance imaging instrument (MRI scanner), an X-ray source with film or a detector (e.g., conventional or digital radiography system), an X-ray computed tomography (CT) or computed axial tomography (CAT) scanner, a gamma camera, or a positron emission tomography (PET) scanner. Various medical imaging systems have been developed for open surgery as well as for laparoscopic, thoracoscopic, and robot-assisted surgery and can be used in the practice of the invention. Conventional laparoscopes and endoscopes can be equipped with a photodetector (e.g., camera or CCD detector) to provide guidance during medical procedures. Fiber-optic imaging systems can also be used, which include portable handheld microscopes, flexible endoscopes, and microendoscopes. For example, an illumination source can be added to such devices to allow fluorescence imaging. A miniaturized ultrasound transducer can be added to the tip of a laparoscope or catheter for intravascular ultrasound (IVUS) imaging. Miniaturized imaging systems can be used that allow imaging inside small cavities and constricted spaces. In addition, miniaturized imaging devices (e.g., microendoscopes) may be implanted within a subject for long-term imaging studies. In addition, a camera may be used to take both photographic images of a subject and to detect signals from the diagnostic agent, so that photographic images of the subject and images of the signals from the diagnostic agent can be superimposed to allow regions containing the diagnostic agent to be mapped to the subject's anatomy.

Pharmaceutical Compositions and Methods of Administration

Also disclosed herein are pharmaceutical compositions comprising one or more of the nucleic acids, vectors, and/or compositions provided herein and one or more pharmaceutically acceptable carriers. The compositions can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids: antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, di saccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of vectors to be administered will vary depending, for example, on the particular viral vector, the mode of administration, the treatment goal, the individual, and the cell type(s) being targeted, and can be determined by methods standard in the art.

As will be readily apparent to one skilled in the art, the useful in vivo dosage of the nucleic acids, vectors, and/or compositions to be administered and the particular mode of administration will vary depending upon the age, weight, the severity of the affliction, and animal species treated, the particular IFFL that is used, and the specific use for which the IFFL is employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. Dosages of nucleic acids, vectors, and/or compositions provided can depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1\times10^9$ to $1\times10^{16}$ genomes virus viral. A preferred human dosage can be about $1\times10^{13}$ to $1\times10^{16}$ viral vector genomes. The dosage will be adjusted to balance the therapeutic benefit against any side effects and such dosages may vary depending upon the therapeutic application for which the recombinant vector is employed. The levels of expression of the payload can be monitored to determine the amount and/or frequency of dosage resulting from the viral vector in some embodiments.

Nucleic acids, vectors, and/or compositions disclosed herein can be administered to a subject (e.g., a human) in need thereof. The route of the administration is not particularly limited. For example, a therapeutically effective amount of nucleic acids, vectors, and/or compositions can be administered to the subject by via routes standard in the art. Route(s) of administration can be readily determined by one skilled in the art taking into account the infection and/or disease state being treated and the target cells/tissue(s) that are to express the payload protein.

The administering can comprise systemic administration (e.g., intravenous, intramuscular, intraperitoneal, or intraarticular). Administering can comprise intrathecal administration, intracranial injection, aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof.

Administering can comprise an injection into a brain region (e.g., direct administration to the brain parenchyma). The brain region can comprise the Lateral parabrachial nucleus, brainstem, Medulla oblongata, Medullary pyramids, Olivary body, Inferior olivary nucleus, Rostral ventrolateral medulla, Respiratory center, Dorsal respiratory group, Ventral respiratory group, Pre-Botzinger complex, Botzinger complex, Paramedian reticular nucleus, Cuneate nucleus, Gracile nucleus, Intercalated nucleus, Area postrema, Medullary cranial nerve nuclei, Inferior salivatory nucleus, Nucleus ambiguus, Dorsal nucleus of vagus nerve, Hypoglossal nucleus, Solitary nucleus, Pons, Pontine nuclei, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, Tectum, Corpora quadrigemina, inferior colliculi, superior colliculi, Pretectum, Tegmentum, Periaqueductal gray, Parabrachial area, Medial parabrachial nucleus, Subparabrachial nucleus (Kolliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), Pineal body, Habenular nucleim Stria medullares, Taenia thalami, Subcommissural organ, Thalamus, Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, Hypothalamus, limbic system, HPA axis, preoptic area, Medial preoptic nucleus, Suprachiasmatic nucleus, Paraventricular nucleus, Supraoptic nucleusm Anterior hypothalamic nucleus, Lateral preoptic nucleus, median preoptic nucleus, periventricular preoptic nucleus, Tuberal, Dorsomedial hypothalamic nucleus, Ventromedial nucleus, Arcuate nucleus, Lateral area, Tuberal part of Lateral nucleus, Lateral tuberal nuclei, Mammillary nuclei, Posterior nucleus, Lateral area, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, Subthalamus, Subthalamic nucleus, Zona incerta, Pituitary gland, neurohypophysis, Pars intermedia, adenohypophysis, cerebral hemispheres, Corona radiata, Internal capsule, External capsule, Extreme capsule, Arcuate fasciculus, Uncinate fasciculus, Perforant Path, Hippocampus, Dentate gyrus, Cornu ammonis, Cornu ammonis area 1, Cornu ammonis area 2, Cornu ammonis area 3, Cornu ammonis area 4, Amygdala, Central nucleus, Medial nucleus (accessory olfactory system), Cortical and basomedial nuclei, Lateral and basolateral nuclei, extended amygdala, Stria terminalis, Bed nucleus of the stria terminalis, Claustrum, Basal ganglia, Striatum, Dorsal striatum (aka neostriatum), Putamen, Caudate nucleus, Ventral striatum, Striatum, Nucleus accumbens, Olfactory tubercle, Globus pallidus, Subthalamic nucleus, Basal forebrain, Anterior perforated substance, Substantia innominata, Nucleus basalis, Diagonal band of Broca, Septal nuclei, Medial septal nuclei, Lamina terminalis, Vascular organ of lamina terminalis, Olfactory bulb, Piriform cortex, Anterior olfactory nucleus, Olfactory tract, Anterior commissure, Uncus, Cerebral cortex, Frontal lobe, Frontal cortex, Primary motor cortex, Supplementary motor cortex, Premotor cortex, Prefrontal cortex, frontopolar cortex, Orbitofrontal cortex, Dorsolateral prefrontal cortex, dorsomedial prefrontal cortex, ventrolateral prefrontal cortex, Superior frontal gyrus, Middle frontal gyrus, Inferior frontal gyrus, Brodmann areas (4, 6, 8, 9, 10, 11, 12, 24, 25, 32, 33, 44, 45, 46, and/or 47), Parietal lobe, Parietal cortex, Primary somatosensory cortex (S), Secondary somatosensory cortex (S2), Posterior parietal cortex, postcentral gyrus, precuneus, Brodmann areas (1, 2, 3 (Primary somesthetic area), 5, 7, 23, 26, 29, 31, 39, and/or 40), Occipital lobe, Primary visual cortex (V1), V2, V3, V4, V5/MT, Lateral occipital gyrus, Cuneus, Brodmann areas (17 (V1, primary visual cortex), 18, and/or 19), temporal lobe, Primary auditory cortex (A1), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas (9, 20, 21, 22, 27, 34, 35, 36, 37, 38, 41, and/or 42), Medial superior temporal area (MST), insular cortex, cingulate cortex, Anterior cingulate, Posterior cingulate, dorsal cingulate, Retrosplenial cortex, Indusium griseum, Subgenual area 25, Brodmann areas (23, 24; 26, 29, 30 (retrosplenial areas), 31, and/or 32), cranial nerves (Olfactory (I), Optic (II), Oculomotor (III), Trochlear (IV), Trigeminal (V), Abducens (VI), Facial (VII), Vestibulocochlear (VIII), Glossopharyngeal (IX), Vagus (X), Accessory (XI), Hypoglossal (XII)), or any combination thereof. The brain region can comprise neural pathways Superior longitudinal fasciculus, Arcuate fasciculus, Thalamocortical radiations, Cerebral peduncle, Corpus callosum, Posterior commissure, Pyramidal or corticospinal tract, Medial longitudinal fasciculus, dopamine system, Mesocortical pathway, Mesolimbic pathway, Nigrostriatal pathway, Tuberoinfundibular pathway, serotonin system, Norepinephrine Pathways, Posterior column-medial lemniscus pathway, Spinothalamic tract, Lateral spinothalamic tract, Anterior spinothalamic tract, or any combination thereof.

Nucleic acids, vectors, and/or compositions to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of nucleic acids, vectors, and/or compositions expressing the therapeutic protein is administered to a host in need of such treatment. The use of the nucleic acids, vectors, and/or compositions provided herein in the manufacture of a medicament for inducing immunity in, or providing gene therapy to, a host is within the scope of the present application.

A therapeutically effective amount of the nucleic acids, vectors, and/or compositions provided herein can be administered to a subject at various points of time. For example, the nucleic acids, vectors, and/or compositions provided herein can be administered to the subject prior to, during, or after the subject has developed a disease, disorder, and/or infection. The nucleic acids, vectors, and/or compositions provided herein can also be administered to the subject prior to, during, or after the occurrence of a disease, disorder, and/or infection. In some embodiments, the nucleic acids, vectors, and/or compositions provided herein are administered to the subject during remission of the disease or disorder. In some embodiments, the nucleic acids, vectors, and/or compositions provided herein are administered prior to the onset of the disease or disorder in the subject. In some embodiments, nucleic acids, vectors, and/or compositions provided herein are administered to a subject at a risk of developing the disease or disorder.

The dosing frequency of the nucleic acids, vectors, and/or compositions provided herein can vary. For example, nucleic acids, vectors, and/or compositions provided herein can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the nucleic acids, vectors, and/or compositions provided herein are administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

EXAMPLES

Some aspects of the embodiments discussed above are disclosed in further detail in the following examples, which are not in any way intended to limit the scope of the present disclosure.

Example 1

Proof-of-Principle for Protein-Level Incoherent Feed-Forward Loop Circuits

This example provides experimental demonstration of protein-level catalytic incoherent feed forward loops which show dosage compensating expression.

Figure 1B:
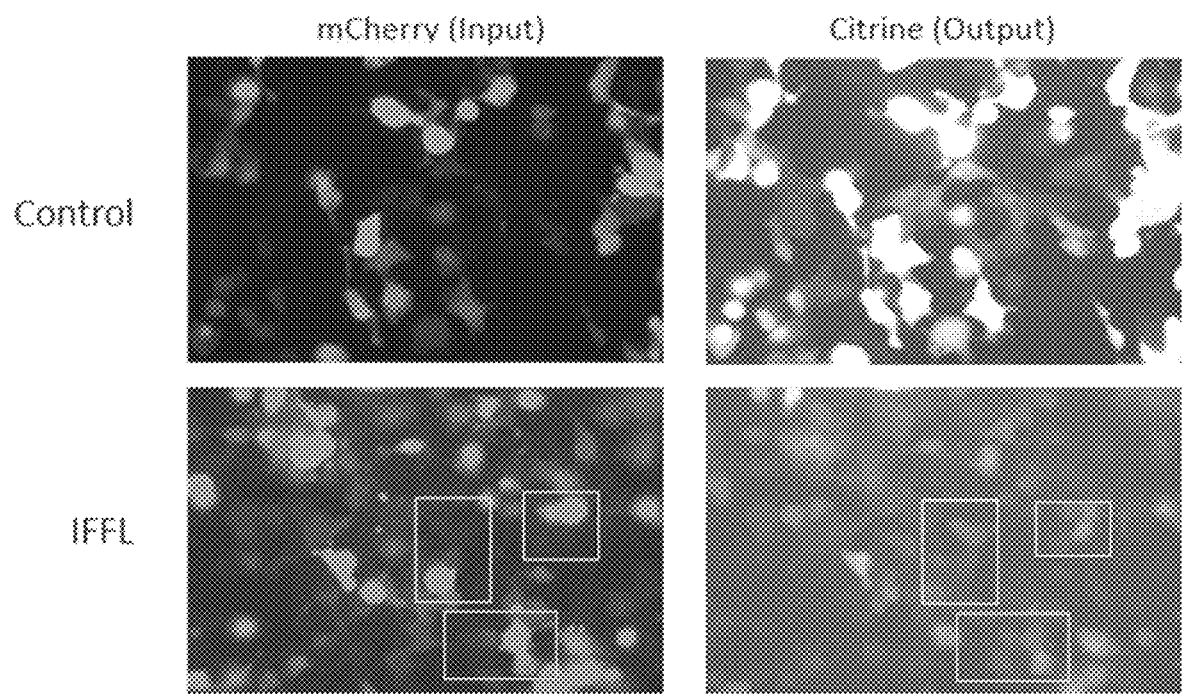
Figure 1C:
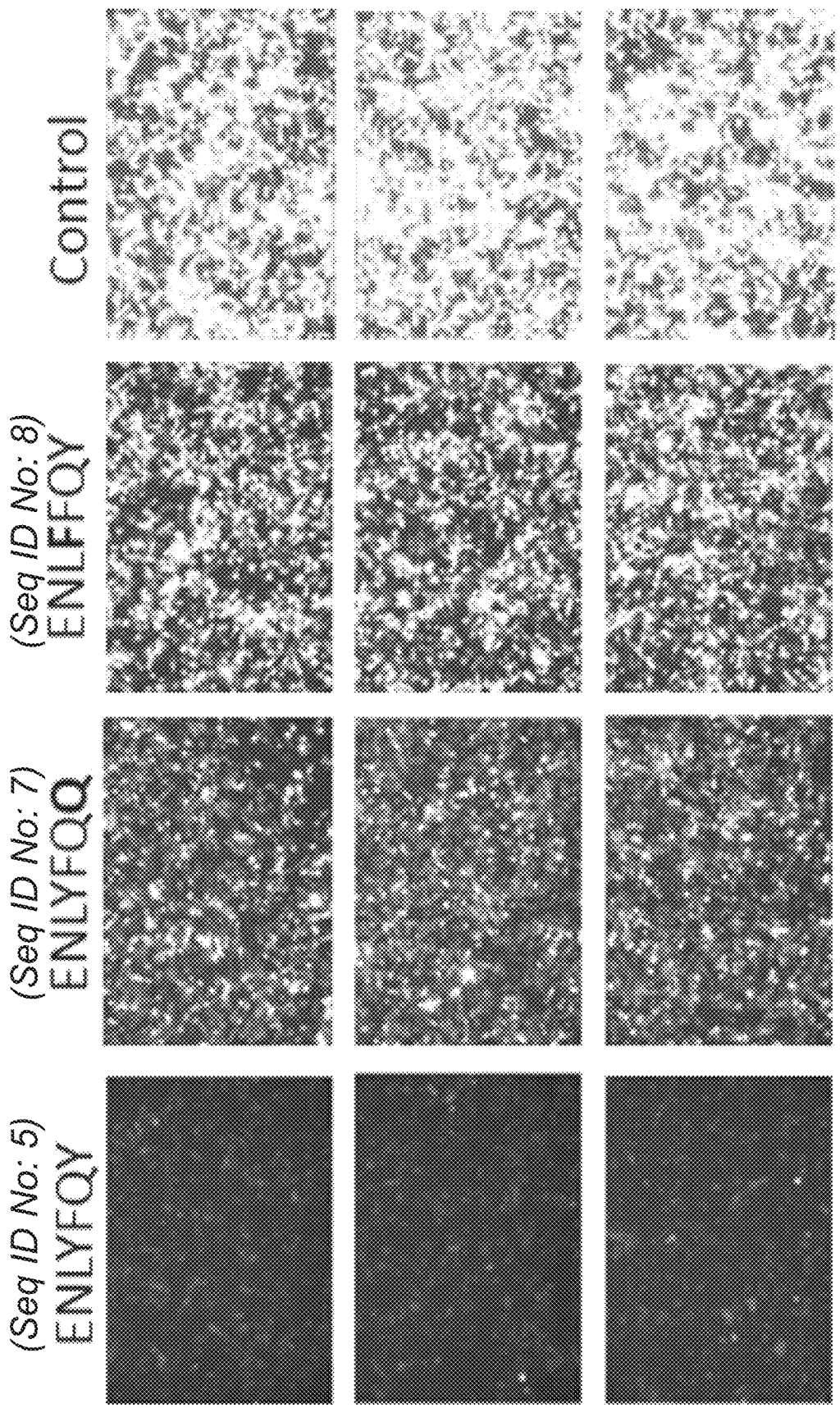
Figure 1D:
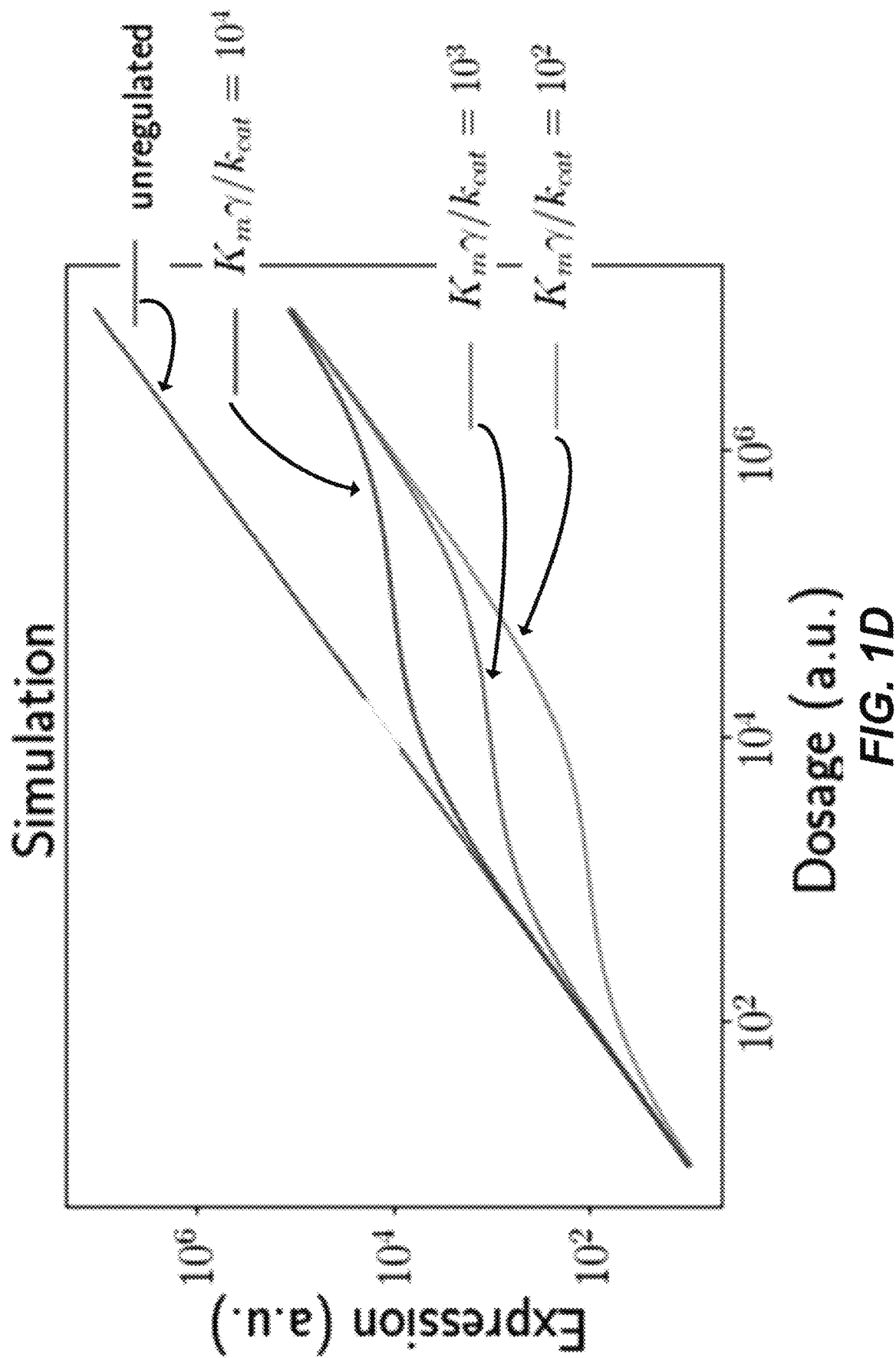
Figure 1E:
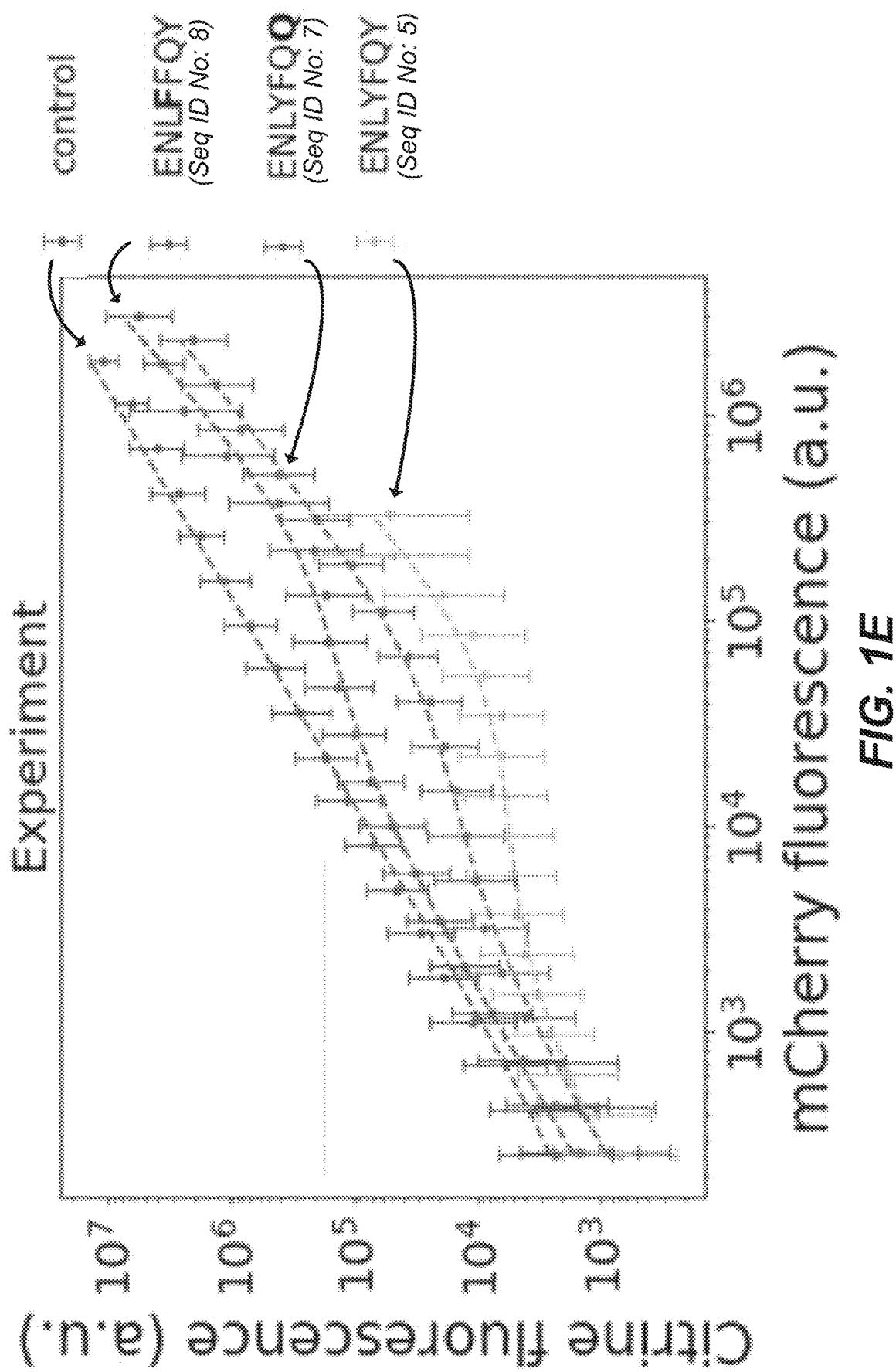

Single transcript protein-level IFFLs consisting of a protein with a fused N-degron tag, a protease which cleaves the N-degron tag, and an unregulated mCherry to read out the total gene dosage, all co-produced via 2A peptide sequences (shown in FIG. 1A) were cloned and tested. An Ef1a promoter drives the expression of (1) the protein of interest (payload protein) ("Citrine"), which is fused to an N-end degron ("N-degron") concealed by a TEVP cleavage site ("ENLYFQY"; SEQ ID NO: 5), (2) the co-translated protease ("TEVP") triggers the degradation of the regulated protein (payload protein) ("Citrine") by cleaving its substrate ("ENLYFQY"; SEQ ID NO: 5), and (3) an unregulated fluorescent protein ("mCherry") is included to provide a measurement of the transcriptional dosage. The components were separated by T2A and P2A self-cleaving peptide sequences. Transcription was terminated with an hGH polyadenylation sequence. FIG. 1B depicts fluorescence microscopy images showing de-correlated input and output as a result of the IFFL. Boxes emphasize adjacent cells where input (mCherry) is very different but output (Citrine) is very similar, compared to controls where both input and output vary significantly. FIG. 1C depicts exemplary data showing that tunability is established using different amino acid sequences for the TEVP cleavage site. The steady state expression of the gene is determined by the $k_{cat}/K_m$ of the protease, which can be varied by changing the sequence of the protease cleavage site. In this example, 3 peptide sequences are chosen with different $k_{cat}/K_m$ for TEVP. A numerical simulation of the steady state gene expression at each of these levels is shown in FIG. 1D. FIG. 1E depicts experimental confirmation of numerical and analytic models of TEVP performance using flow cytometry. HEK293 cells were transiently transfected with plasmid DNA containing the IFFL circuits and after a period of 2 days were analyzed using a flow cytometer. Data is divided into 20 bins per condition, dots indicate the median of this bin, error bars are ±1 standard deviation (in log space) of the bin, the dotted lines are curve fits to the analytical model in Equation (1) shown in Example 5. Flow cytometry measurements on HEK293 cells transiently transfected with these circuits show expression that agrees strikingly with the anticipated results, and leads to steady state expression that can be tuned by adjusting the peptide sequence of the protease cleavage site (FIGS. 1B-1E). The tunability is based on sequence and independent of viral titer, so it should be robust to many of the challenges of Rett syndrome gene therapy and designable to express MeCP2 at the correct level.

Figure 2A:
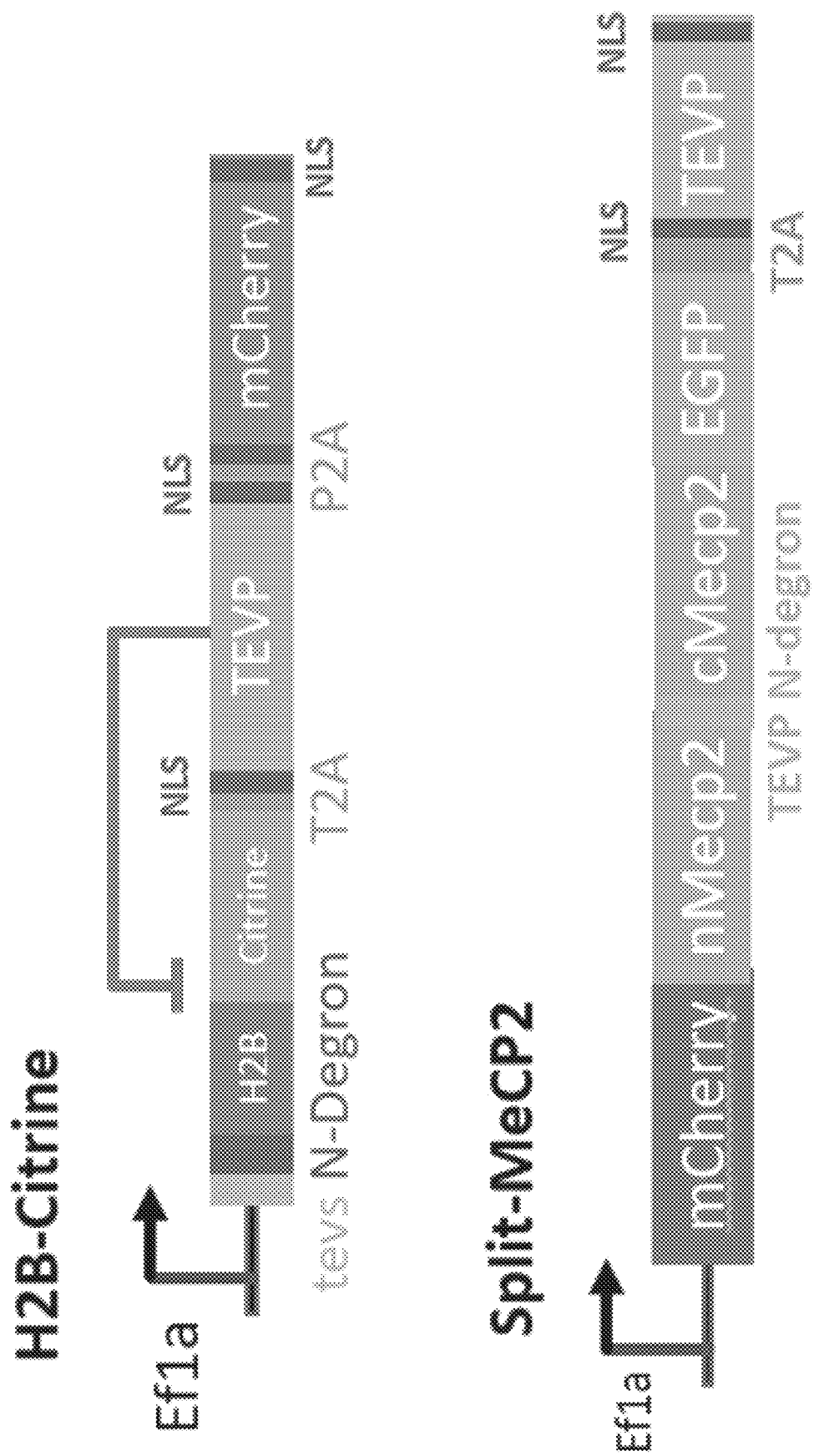
FIGS. 2A-2B depict non-limiting exemplary embodiments and data related to IFFL constructs provided herein.
Figure 2B:
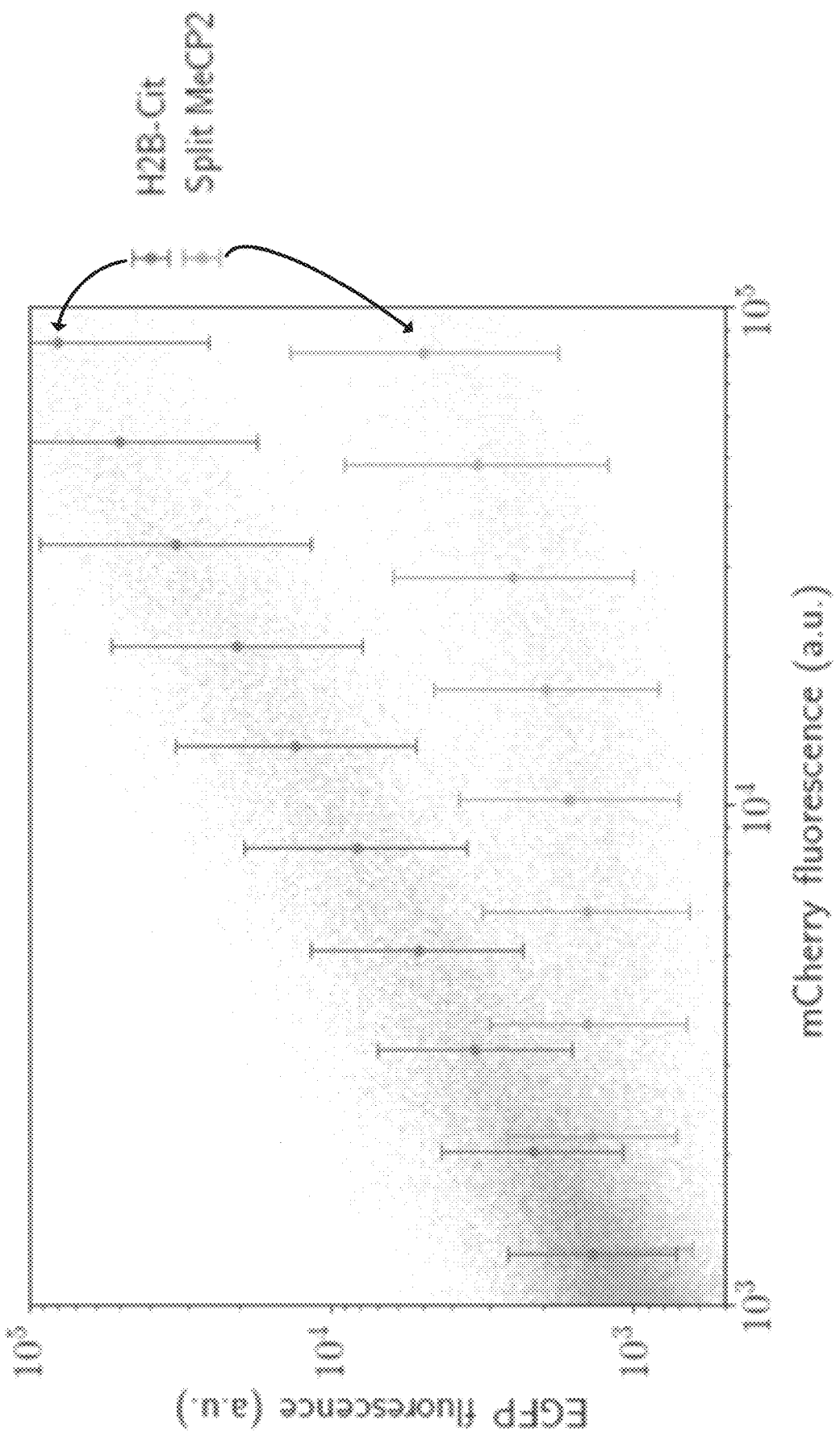

It was found that MeCP2 could not be regulated by the N-terminal tag: an IFFL construct with MeCP2-EGFP being regulated produced proportional MeCP2-EGFP and mCherry expression (data not shown). It was hypothesized that this could be due to inaccessibility of the N-terminus of MeCP2 due to its chromatin incorporation. To test this, the output of a nuclear localized IFFL regulating H2B-Citrine, which is incorporated into chromatin, was compared against a nuclear localized IFFL regulating a Citrine with NLS tags on each terminus ("NLS-Citrine"), which is not incorporated into chromatin. It was found that H2B-Citrine was not regulated by the IFFL while NLS-Citrine construct functioned as in FIG. 1 (not shown), supporting the chromatin incorporation hypothesis. To avoid the chromatin protection, an MeCP2 construct was then designed with a cut site in the center of the protein, between N-terminus—which binds to DNA and chromatin—and a C-terminal co-repressor domain, and it was found that this construct displayed adaptive expression (FIGS. 2A-2B). A H2B-Citrine IFFL ("H2B-Citrine" or "H2B-Cit") construct was generated comprising of an Ef1a promoter driving the expression of an H2B-Citrine fusion with an N-degron tag on the N-terminus, co-produced with a TEVP protease with NLS sequences on each terminus as well as an unregulated mCherry, also with NLS sequences on each terminus (FIG. 2A). A Split-MeCP2 IFFL ("Split-MeCP2") construct was generated comprising an Ef1a promoter driving the expression of an mCherry fused to the N-terminus of an MeCP2 gene with a TEVP cleavage site and N-degron inserted into a glycine/serine rich central region between the N-terminal DNA binding domain and the C-terminal NCoR/SMRT co-repressor domain with an EGFP fused past the C-terminus. A TEVP with NLS sequences on each terminus is co-produced via a self-cleaving T2A peptide sequence. These constructs were transiently transfected into HEK293 cells and were analyzed via flow cytometry after a period of 2 days. The H2B-Cit construct was protected from regulation by the N-degron due to chromatin incorporation, and produced proportional Citrine fluorescence and mCherry fluorescence. The split MeCP2 construct showed adaptive expression of MeCP2-EGFP. Both these methods function in the cytoplasm and nucleus and can, in principle, regulate any proteins localized there.

Figure 3A:
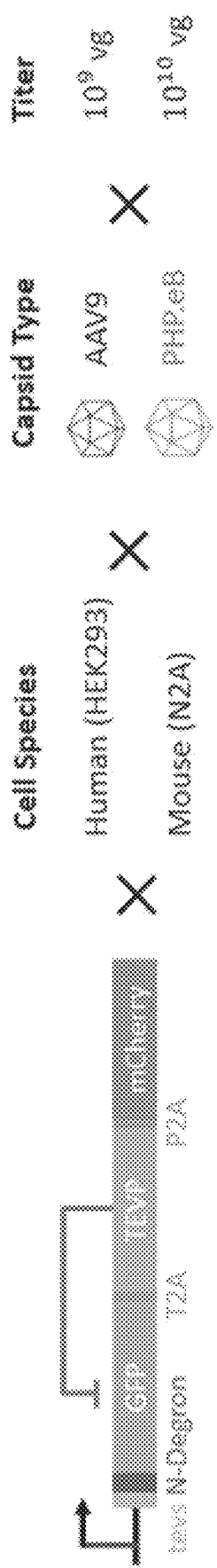
FIGS. 3A-3B depict non-limiting exemplary embodiments and data related to packing of an IFFL construct into AAV vectors.
Figure 3B:
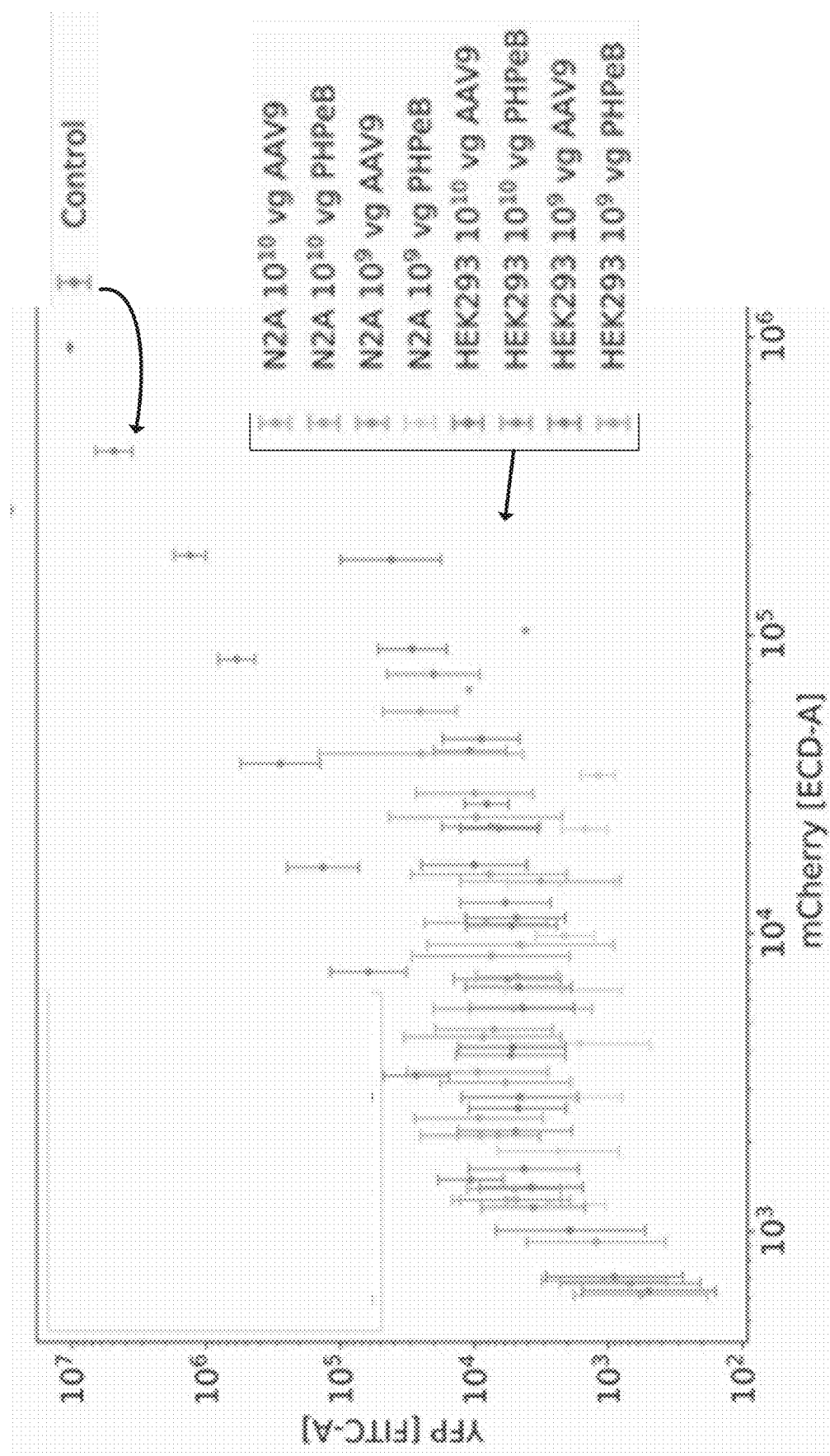

As further proof-of-principle the citrine-regulating circuit was packaged in two different AAV vectors: AAV9 and PHP.eB, and used them to transduce both HEK293s and a mouse glioblastoma cell line (N2A) at two different titers. The protein-level IFFL from FIG. 1 was packaged into AAV9 or PHP.eB vectors and transduced into different cell lines—N2A (mouse glioblastoma cells) and HEK293 (human embryonic kidney cells) at different titers (FIG. 3A). Briefly, AAV viruses were produced in HEK293 cells, purified, and titered using a protocol developed for producing AAV vectors for use in rodents. These purified vectors were added to HEK293 or N2A cells in 24 well plates at titers of $10^9$ or $10^{10}$ viral genomes per well. After 2 days of incubation, the cells were analyzed using flow cytometry. Despite the many differences in conditions, the protein-level IFFL yields the same input-output (mCherry-YFP) curve in expression of the gene of interest (here, YFP). Despite the variety of capsid type, species of cell, and titer of vector, it was found that the gene expression followed the same input-output curve in each case (FIG. 3B). Thus, the protein-level IFFL provided herein can function as a general module for tunable protein-expression that is robust and reliable across widely different conditions.

Example 2

Proof-of-Principle for miRNA-Level Incoherent Feed-Forward Loop Circuits

This example provides experimental demonstration of miRNA-level catalytic incoherent feedforward loops which show dosage compensated expression.

Figure 4A:
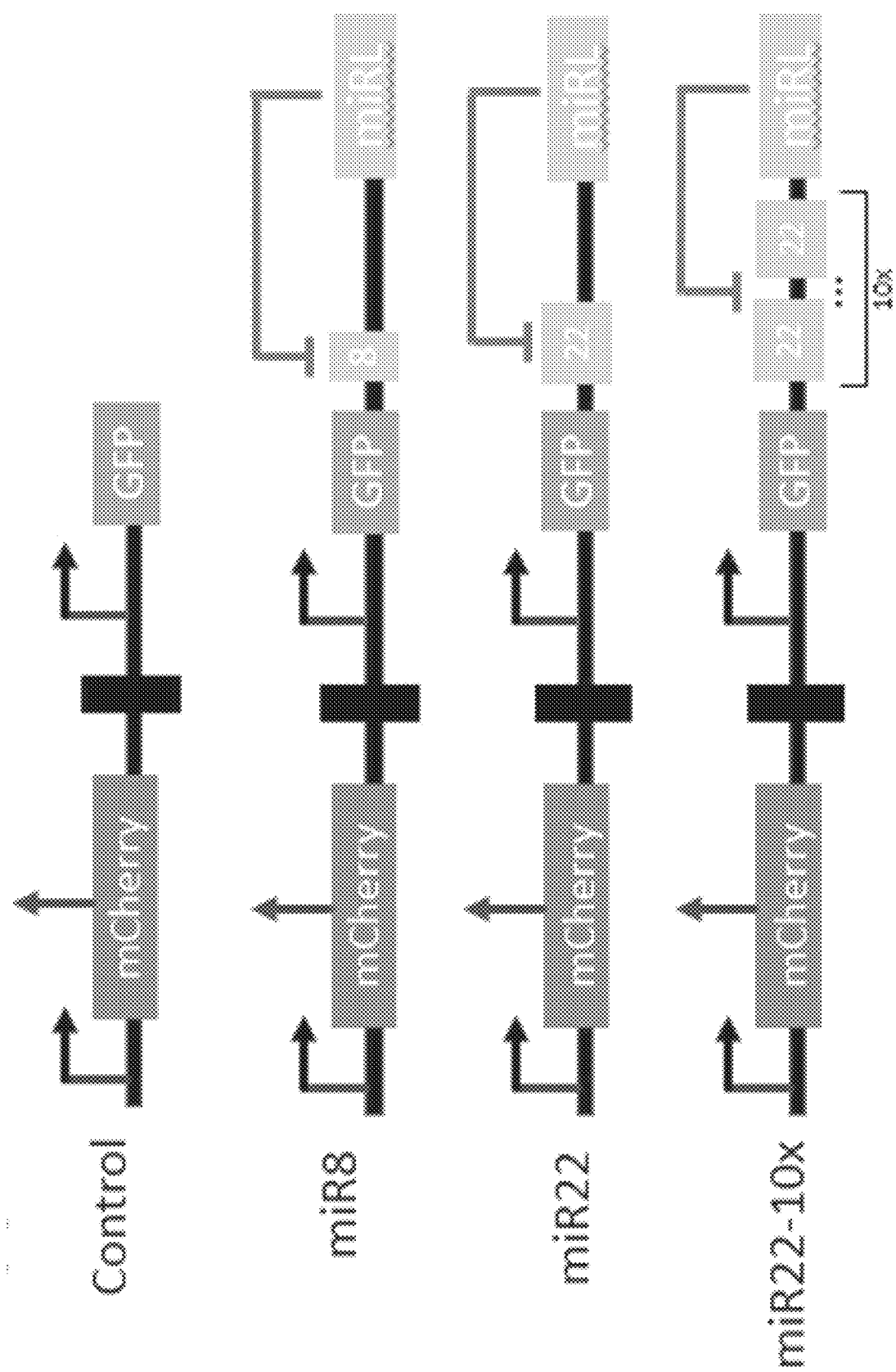
FIGS. 4A-4B depict non-limiting exemplary embodiments and data related to synthetic miRNA IFFL circuits.
Figure 4B:
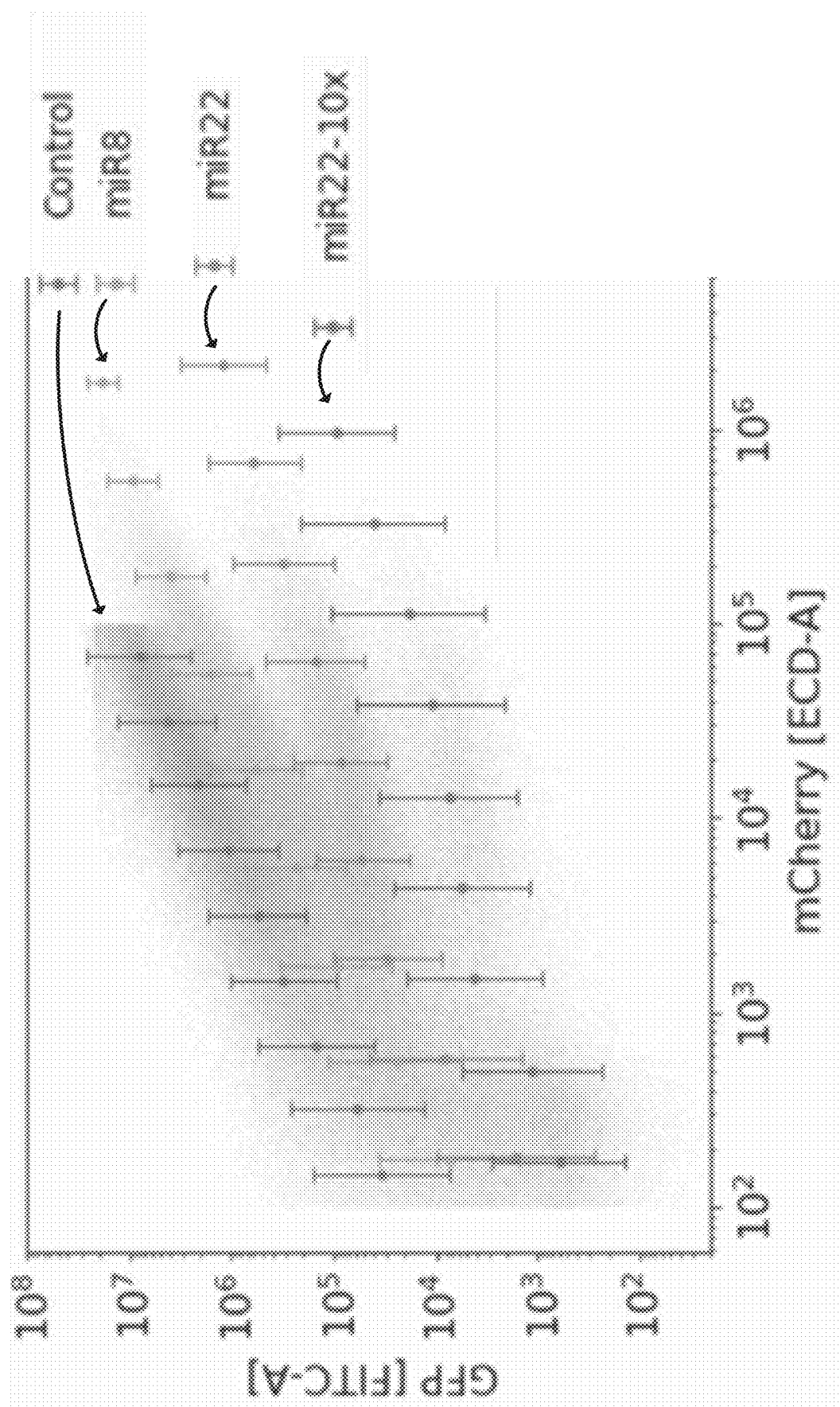
Figure 5A:
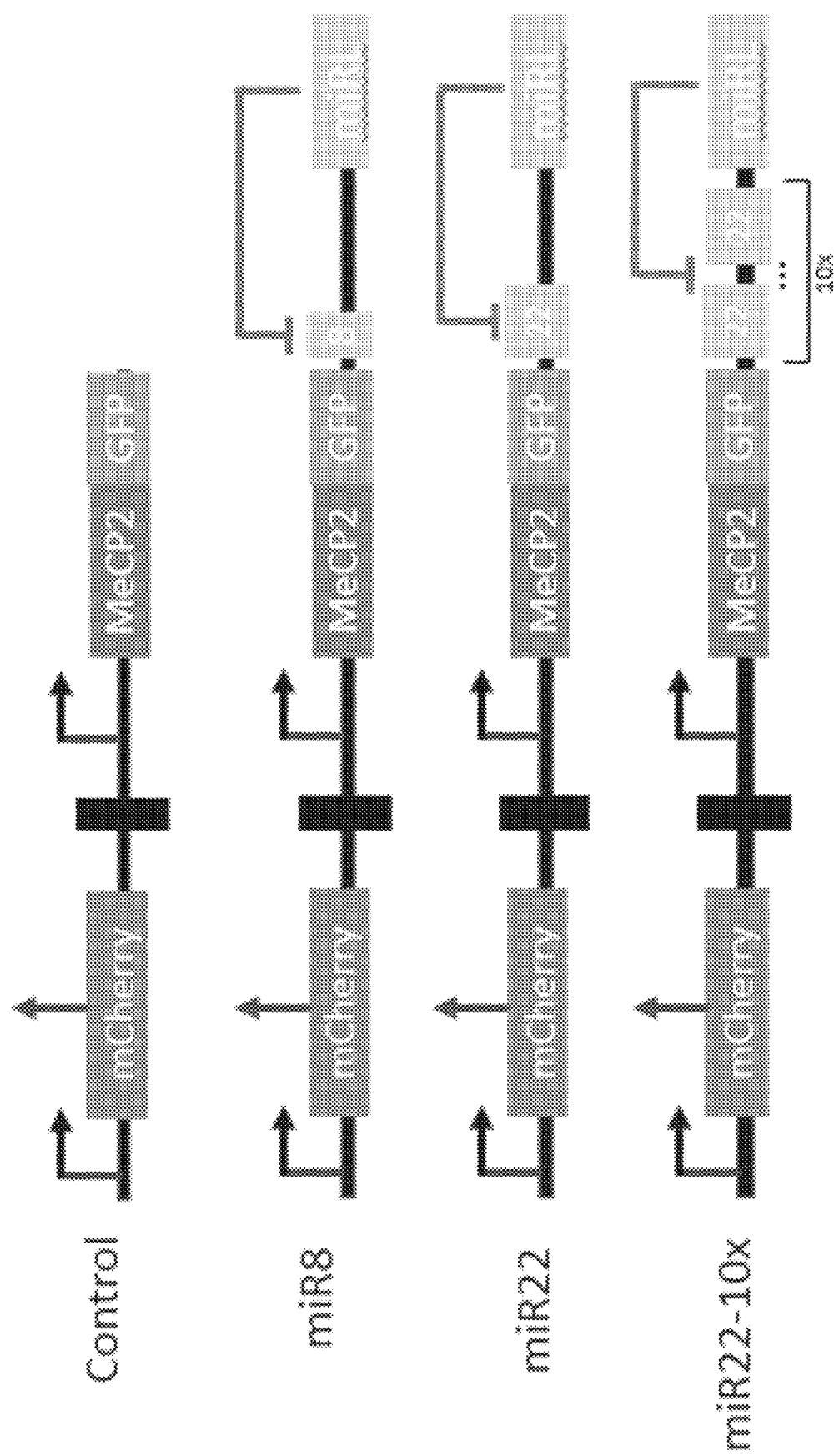
FIGS. 5A-5B depict non-limiting exemplary embodiments and data related to synthetic miRNA IFFL circuits.
Figure 5B:
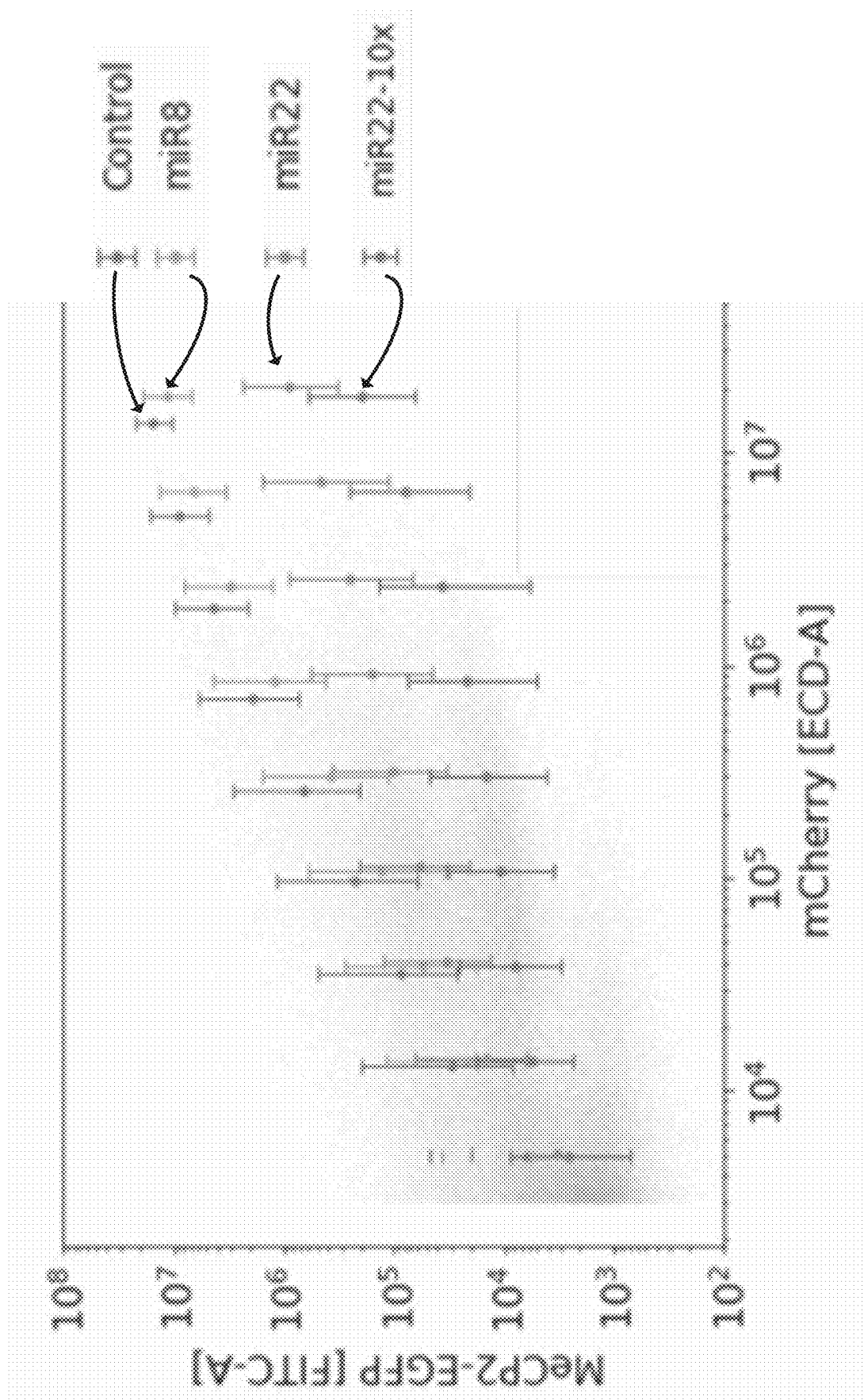

For gene therapy purposes, it can be advantageous to use regulatory methods that do not involve the production of any foreign proteins, which could be immunogenic. This Example describes the testing miRNA IFFLs that achieve dosage compensation without the production of proteins besides the gene of interest by incorporating miRNA target sites as well as a synthetic intron containing an miRNA hairpin sequence into the 3' UTR. The steady state expression of these circuits was tuned by varying the complementarity and copy number of miRNA target sites in the 3' UTR. These miRNA IFFL cassettes were used to create circuits with 3 levels of regulated expression of both GFP (FIG. 4A) and an MeCP2-EGFP fusion (FIGS. 5A-5B). FIG. 4A shows different constructs were designed to provide 4 different GFP expression behavior. All expression constructs are based on an original construct ("Control") which comprises an Ef1a promoter driving mCherry, terminated by a bGH polyadenylation sequence, followed by an insulator, followed by a CMV promoter driving the expression of GFP, terminated by an hGH polyadenylation sequence. First from top of FIG. 4A: Control circuit ("Control") where GFP expression is proportional to mCherry. Second from top of FIG. 4A ("miR8"): an miRNA expression cassette (miRL) is inserted into the 3' UTR as well as a weak target with 8 bp of complementarity. Third from top of FIG. 4A ("miR22"): the 8 bp target is switched out for a 22 bp target, which results in significantly stronger regulation. Fourth from top of FIG. 4A ("miR22-10×"): the 22 bp target is repeated 10 times to yield the strongest regulation and the lowest GFP expression. Thus, tunability is established by varying the complementarity and copy number of the miRNA target sites. FIG. 4B depicts flow cytometry data showing the 4 different levels of expression. HEK293 cells were transiently transfected with these constructs and analyzed on a flow cytometer after a period of 2 days. FIGS. 5A-5B show tunable control of MeCP2 Expression using a synthetic miRNA IFFL. FIG. 5A shows the same constructs from FIG. 4A with an MeCP2-EGFP fusion swapped in for the GFP. FIG. 5B depicts data related to HEK293 cells transiently transfected with these constructs and analyzed on a flow cytometer after a period of 2 days. Flow cytometry data shows 4 levels of MeCP2-EGFP expression. These miRNA IFFLs can thus be used to express arbitrary gene cassettes at defined levels, including MeCP2 as well as large multi-protein circuits, in gene and cell therapies.

Example 3

Figure 6A:
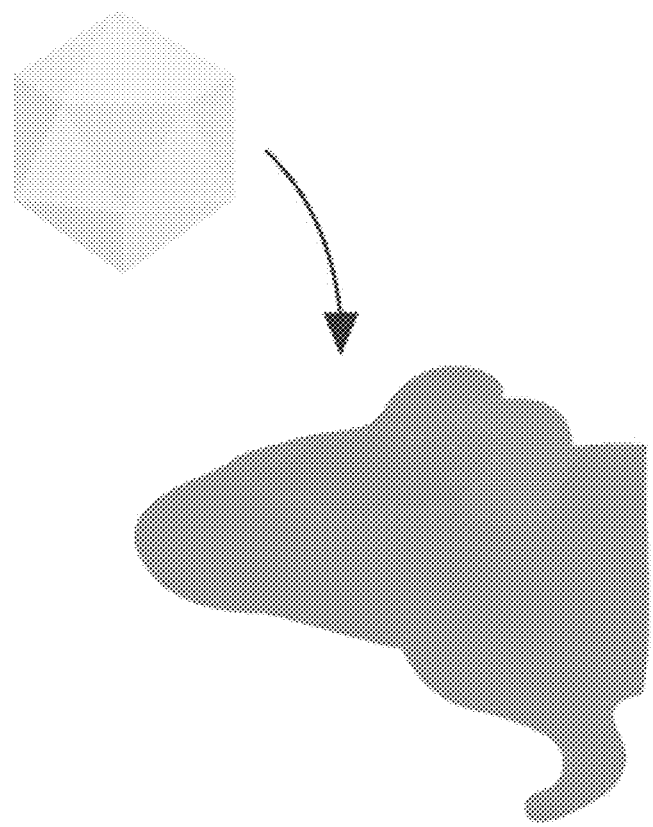
FIGS. 6A-6B depict non-limiting exemplary embodiments and data related to an IFFL circuit motif modulating the expression of virally delivered cargo in mammals.
Figure 6B:
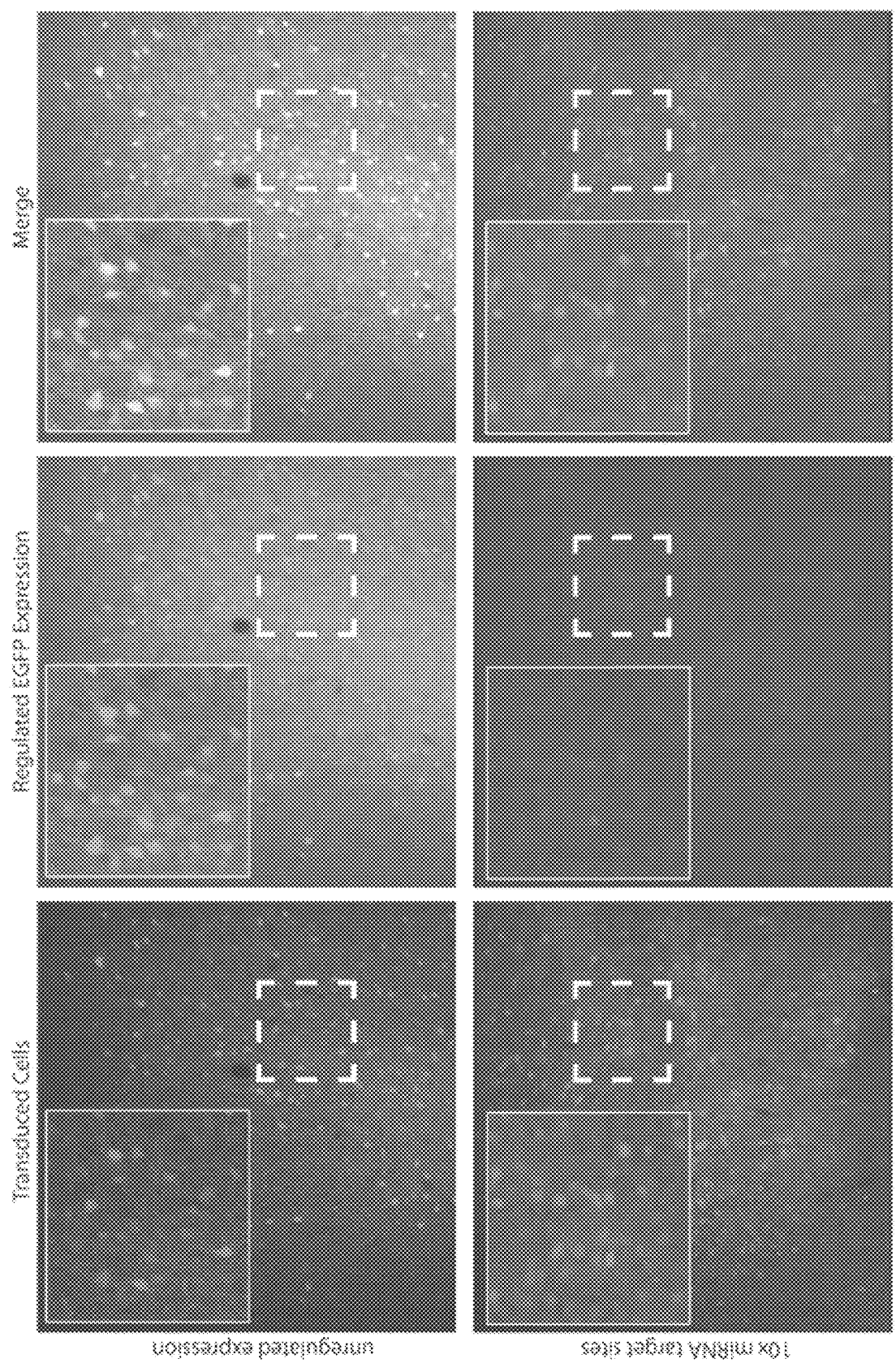

IFFL Circuit Motif Modulates Expression of Virally Delivered Cargo in Mammals This example provides in vivo proof-of-principle experimental demonstration of miRNA-level catalytic incoherent feedforward loops which show dosage compensated expression. FIGS. 6A-6B depict non-limiting exemplary embodiments and data related to an IFFL circuit motif modulating the expression of virally delivered cargo in mammals. AAV genomes containing GFP under IFFL control with either 0 or 10 miRNA target sites were packaged into AAV-CAP.B22 (Flytzanis et al 2020). AAV-IFFL was then delivered via direct injection (1 uL of 5e12 vg/mL) into the cortices of 8 week old male C57Bl6J mice (FIG. 6A). After 14 days of expression, animals were perfused with 4% PFA and brain tissue was collected in 50 uM slices for imaging. Virally transduced cells are indicated by mRuby expression (FIG. 6B; column 1). At similar levels of RFP, the genomes containing 10 miRNA target sites (FIG. 6B; row 2) exhibit marked repression of EGFP, consistent with observations of circuit behavior in vitro. This experiment shows that shows the 10×IFFL circuit successfully regulates the expression of Citrine in a living mouse brain. These mice were behaviorally normal, indicating that the IFFL cassette did not have an adverse effect on mice health.

Example 4 miRNA-Level and Protein-Level Incoherent Feed-Forward Loop Circuits

This example provides in vivo proof-of-principle experimental demonstration of additional miRNA-level and protein-level incoherent feedforward loops described herein which show dosage compensated expression.

Figure 7A:
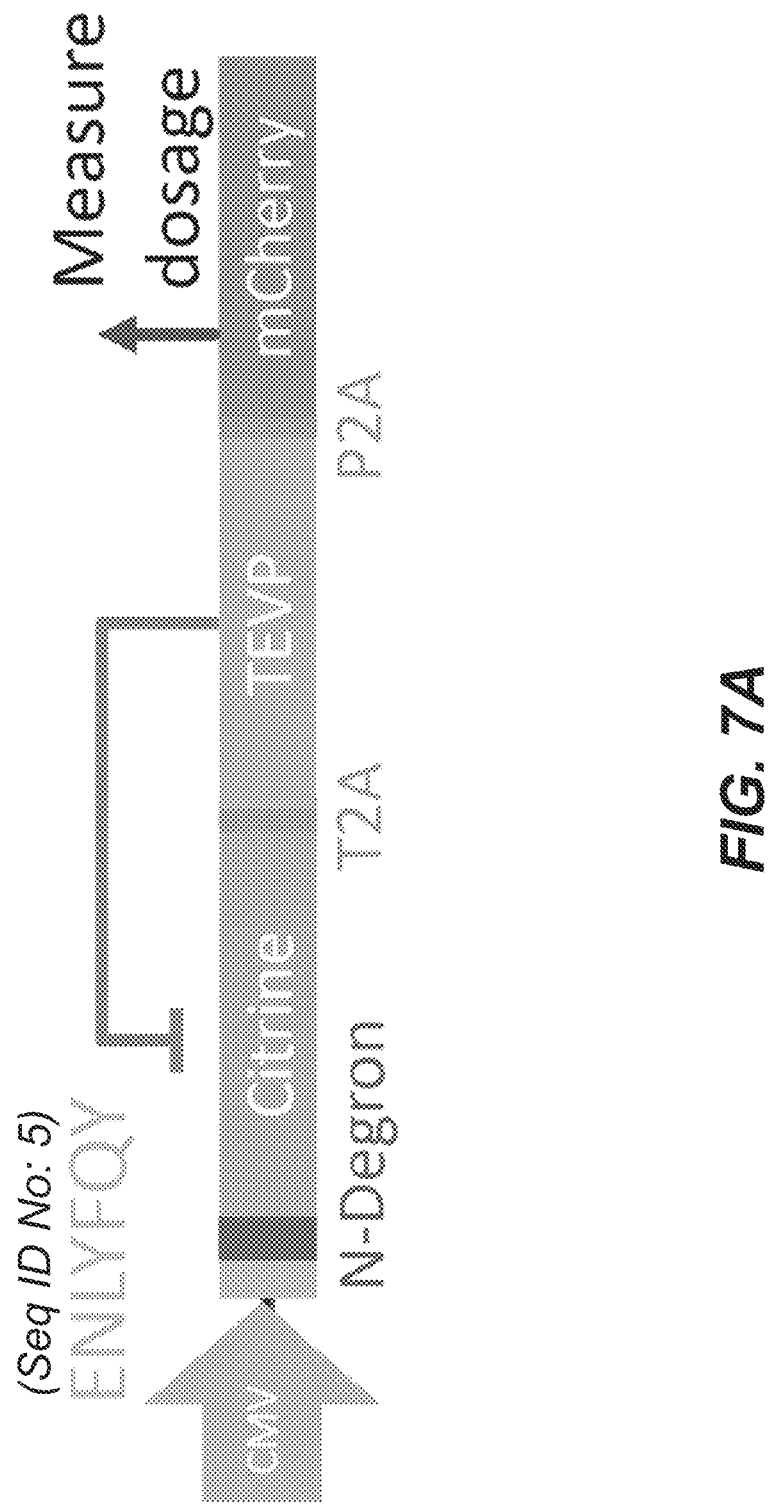
FIGS. 7A-7B depict non-limiting exemplary embodiments and data related to a protein-level IFFL driven by the CMV promoter.
Figure 7B:
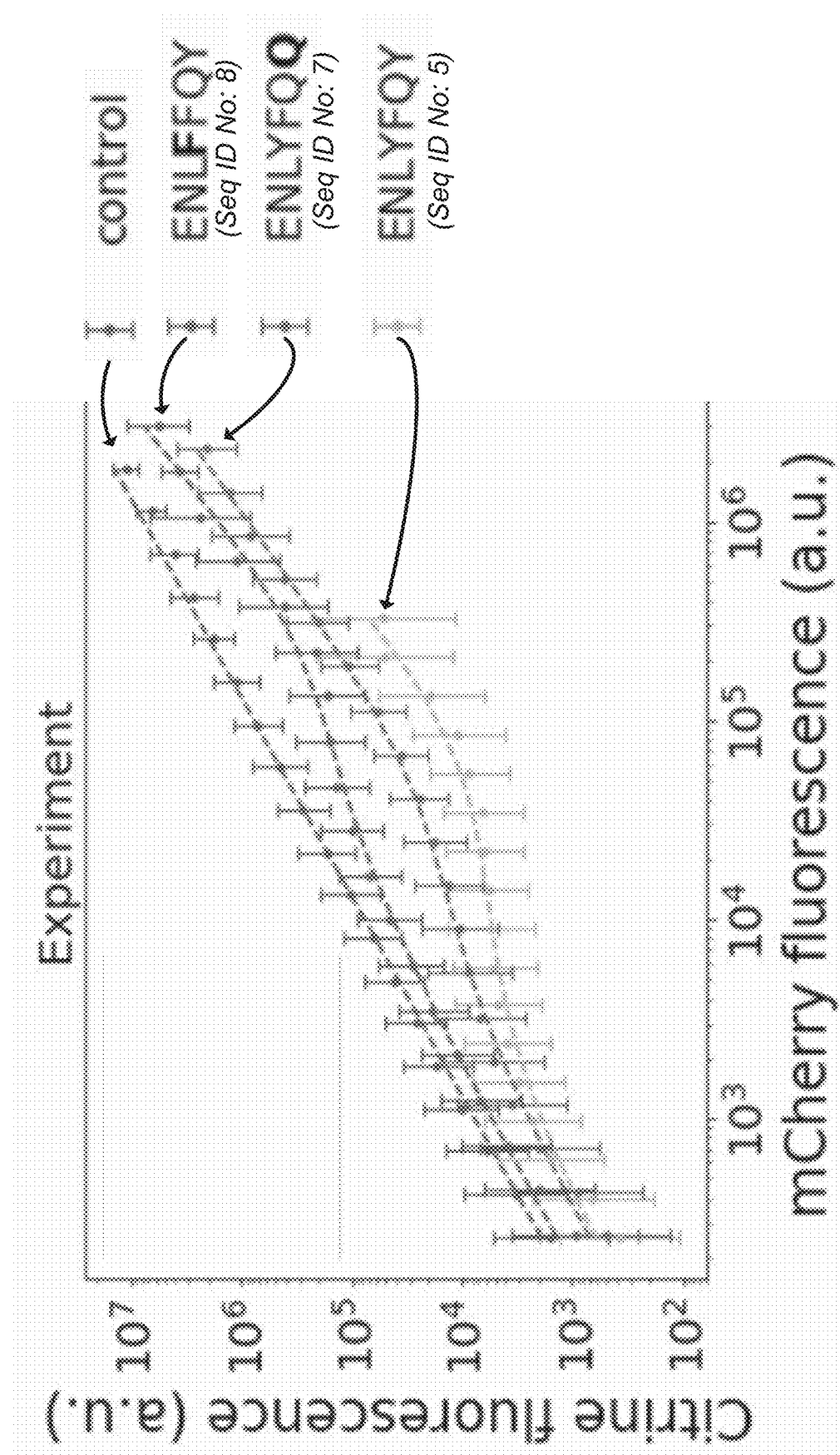
Figure 8A:
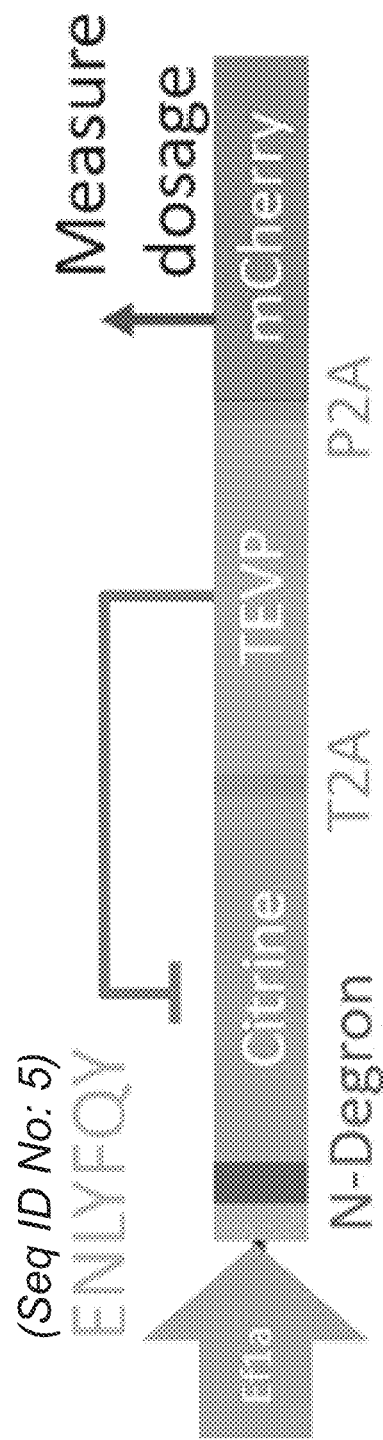
FIGS. 8A-8B depict non-limiting exemplary embodiments and data related to a protein-level IFFL driven by the full Ef1a promoter (with intron).
Figure 8B:
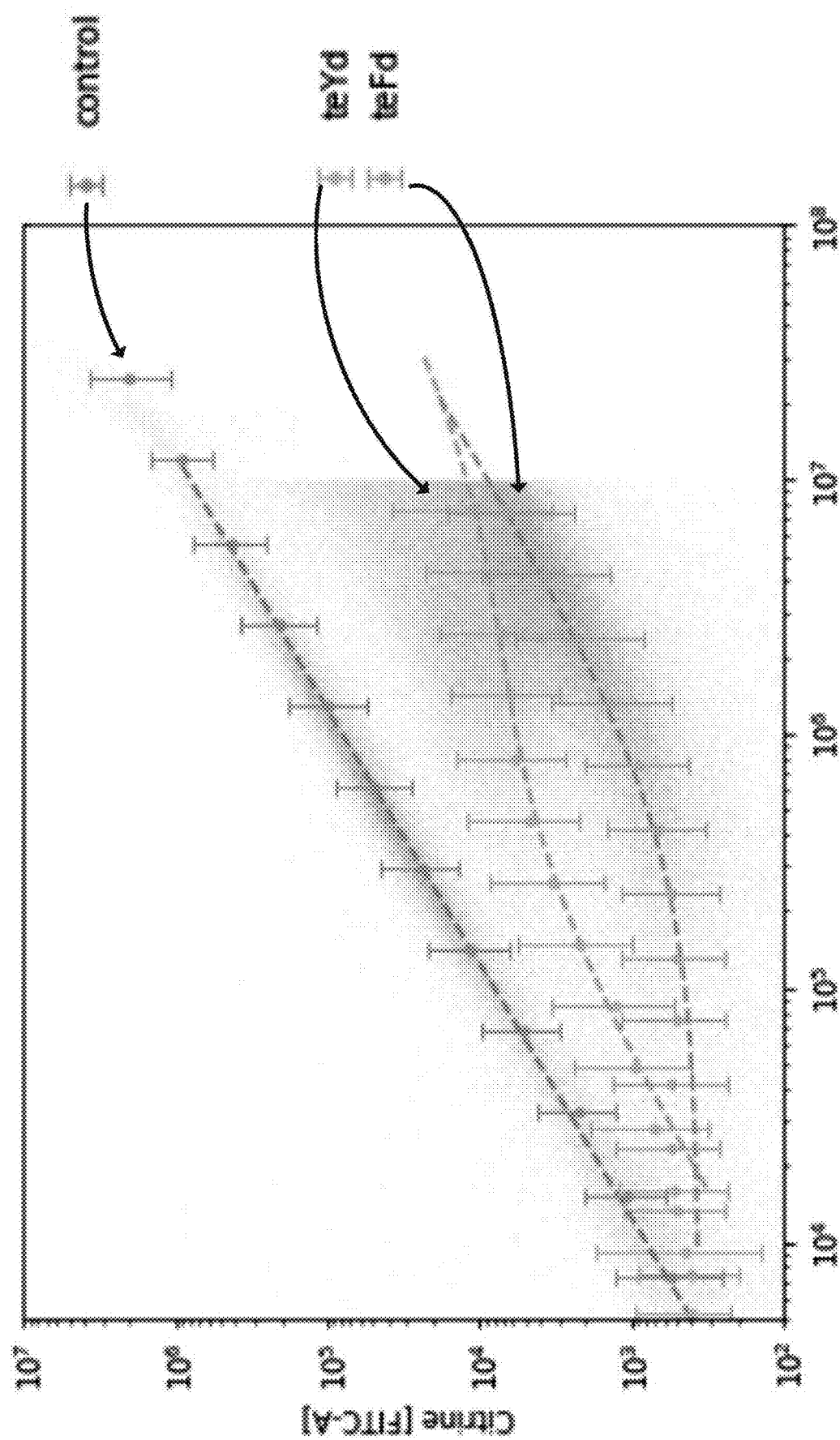
Figure 9A:
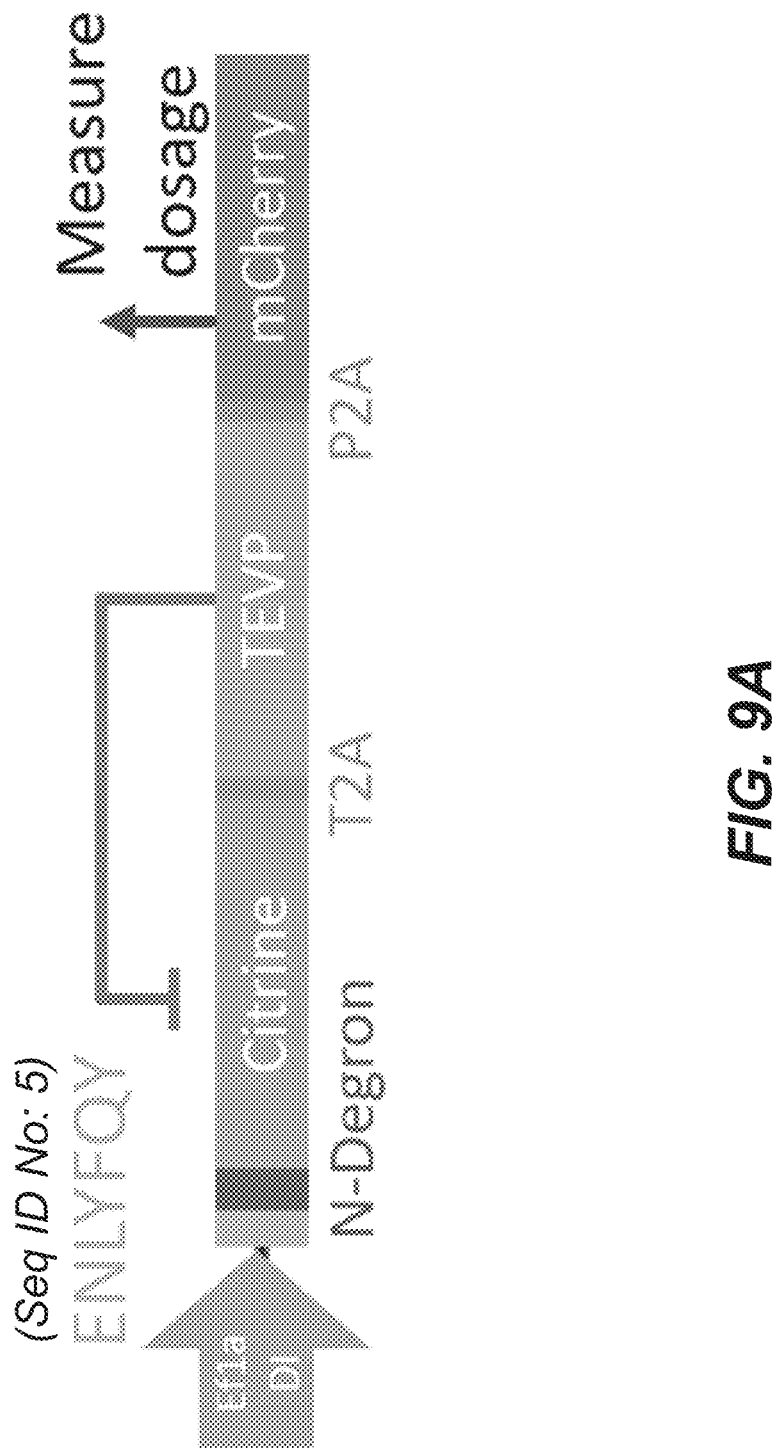
FIGS. 9A-9B depict non-limiting exemplary embodiments and data related to a protein-level IFFL driven by Ef1a promoter (without the intron).
Figure 9B:
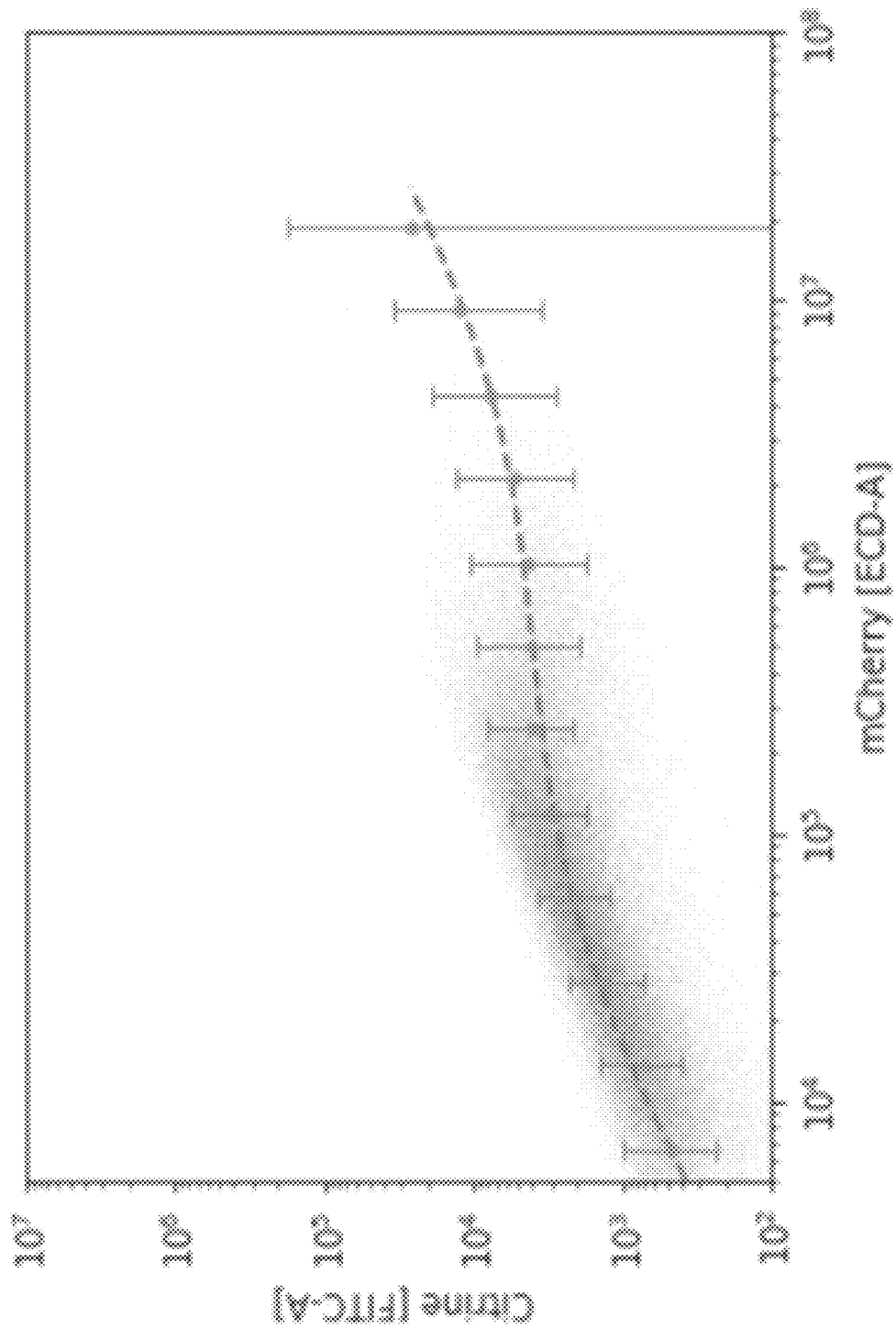

There different protein-level circuits (FIGS. 7A, 8A, and 9A) were constructed comprising different promoters. FIG. 7A depicts a protein-level IFFL driven by the CMV promoter. The canonical TEVP cut site, ENLYFQY (SEQ ID NO: 5), was modified to give different steady state levels in the stable regime, as seen in FIG. 7B. FIG. 8A depicts a protein-level IFFL driven by the full Ef1a promoter (with intron). This construct yielded high expression, and similar functional form to the same construct driven by the CMV promoter (FIG. 8B). In this experiment, the terminal residue in the TEVP cut site was varied, and a very effective terminal residue was discovered: ENLYFQF (SEQ ID NO: 6). FIG. 9A depicts a protein-level IFFL driven by Ef1a promoter (without the intron). This promoter expressed at a much lower level than the CMV or full Ef1a promoters, but yielded a similar steady state for the canonical cut site (FIG. 9B). This construct was the construct used in the AAV IFFL experiments described above, to yield similar steady states on different species of cells, titers of virus, and capsids. In sum, despite some variations in the overall expression of the constructs, the output expression of the gene of interest (Citrine) followed the same functional form.

Figure 10A:
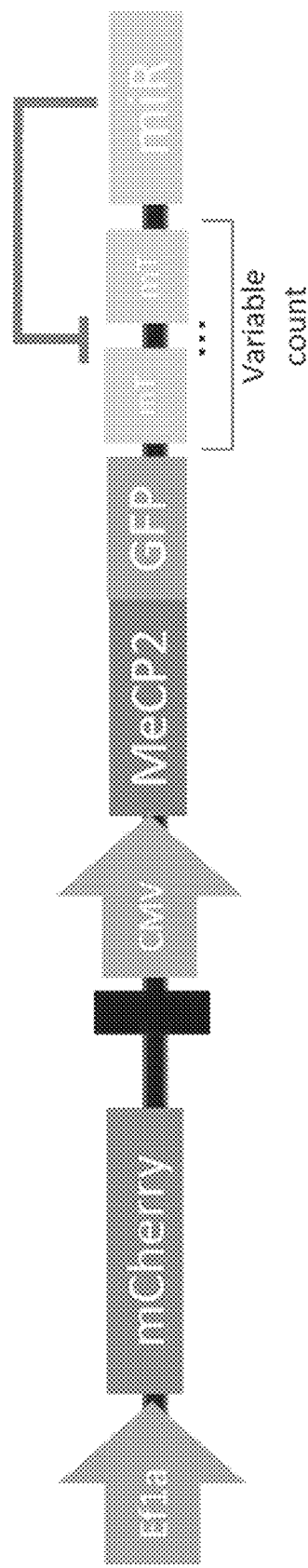
FIGS. 10A-10B depict non-limiting exemplary embodiments and data related to a first embodiment of a miRNA-level IFFL circuit.
Figure 10B:
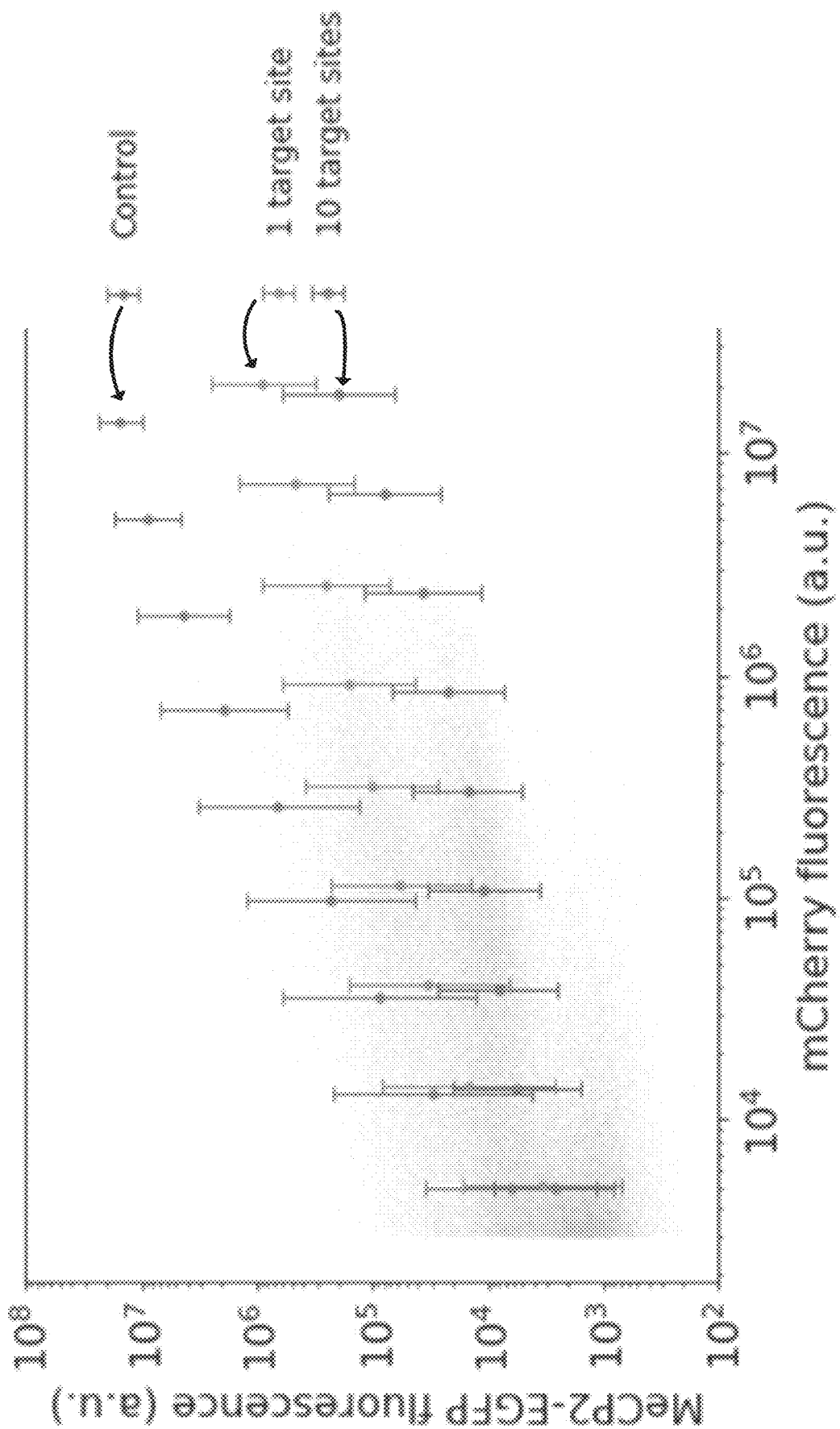
Figure 11A:
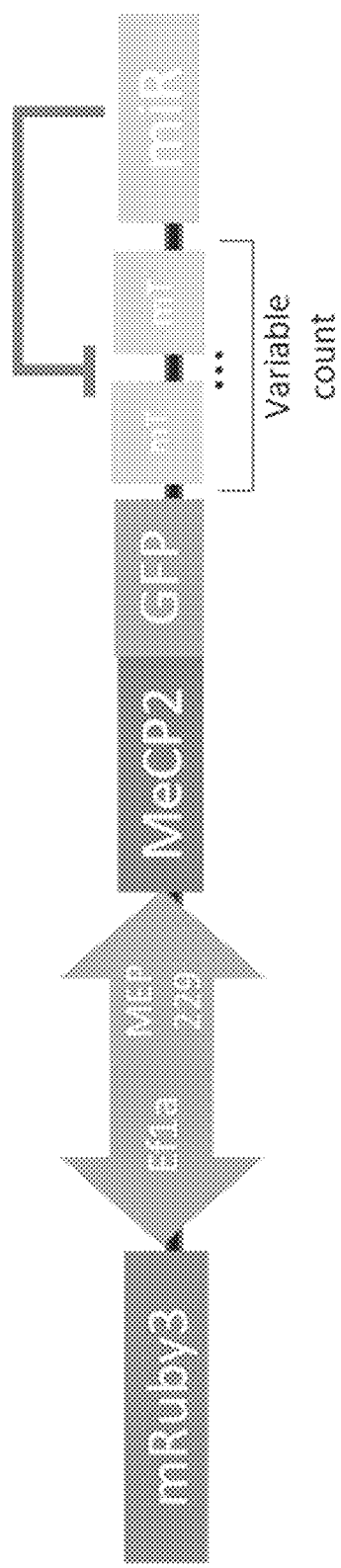
FIGS. 11A-11B depict non-limiting exemplary embodiments and data related to a second embodiment of a miRNA-level IFFL circuit.
Figure 11B:
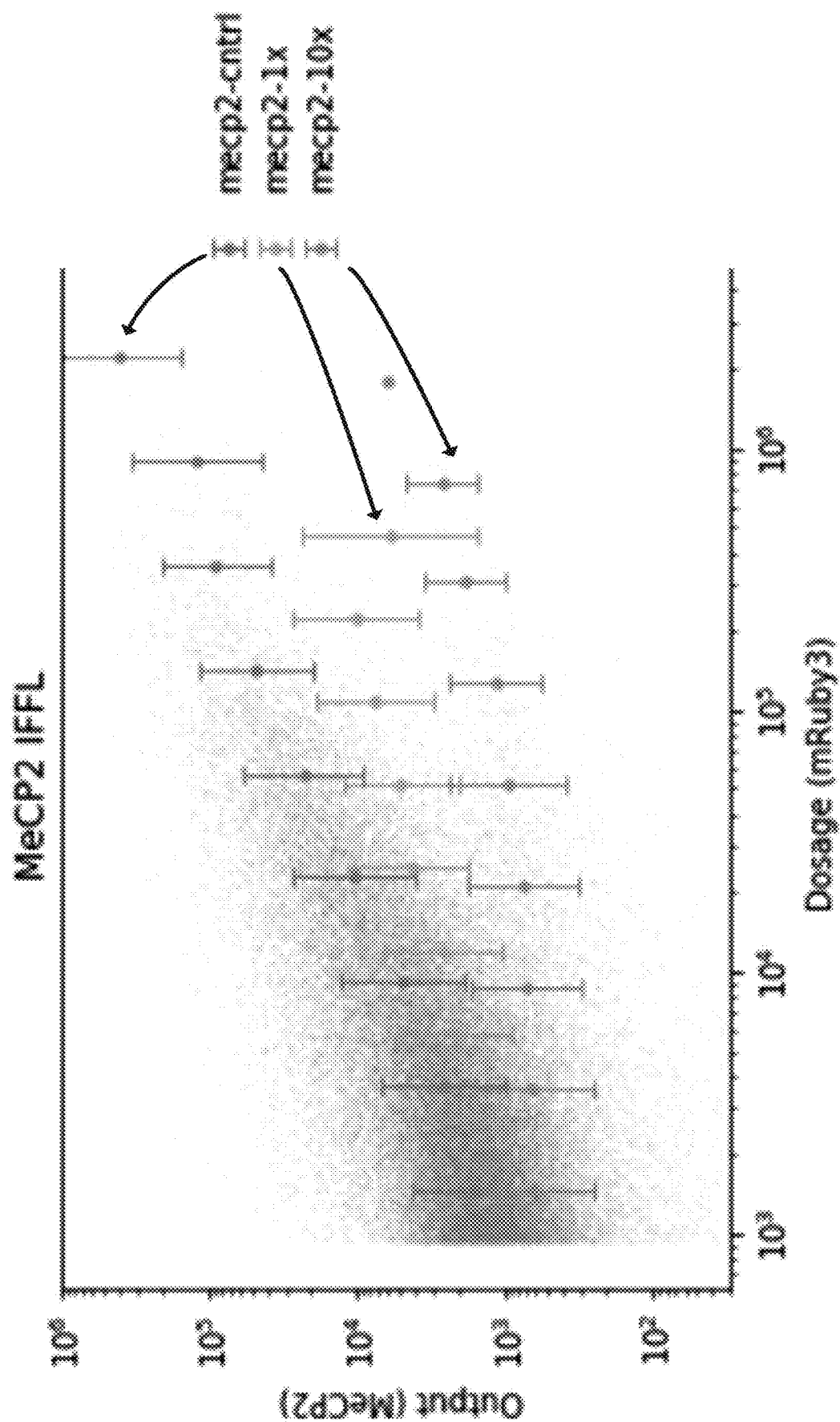
Figure 12A:
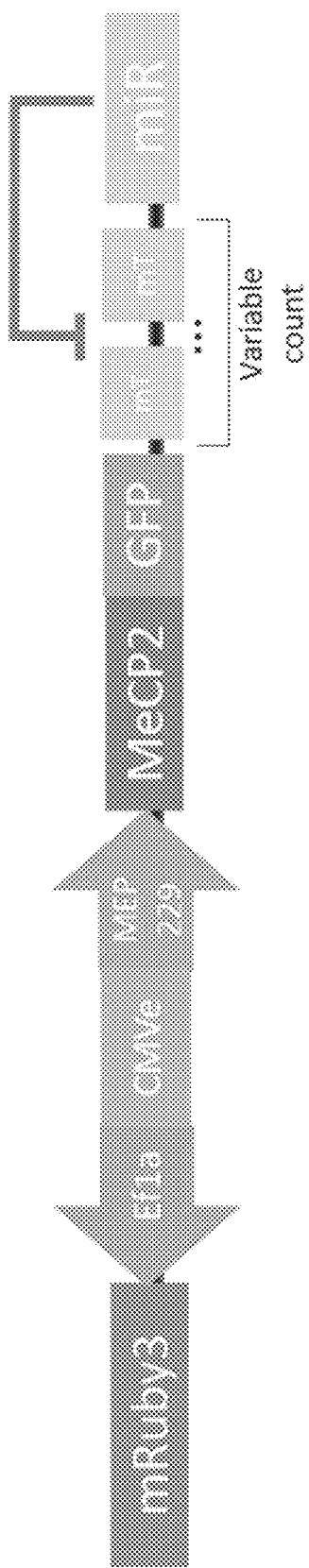
FIGS. 12A-12B depict non-limiting exemplary embodiments and data related to a third embodiment of a miRNA-level IFFL circuit.
Figure 12B:
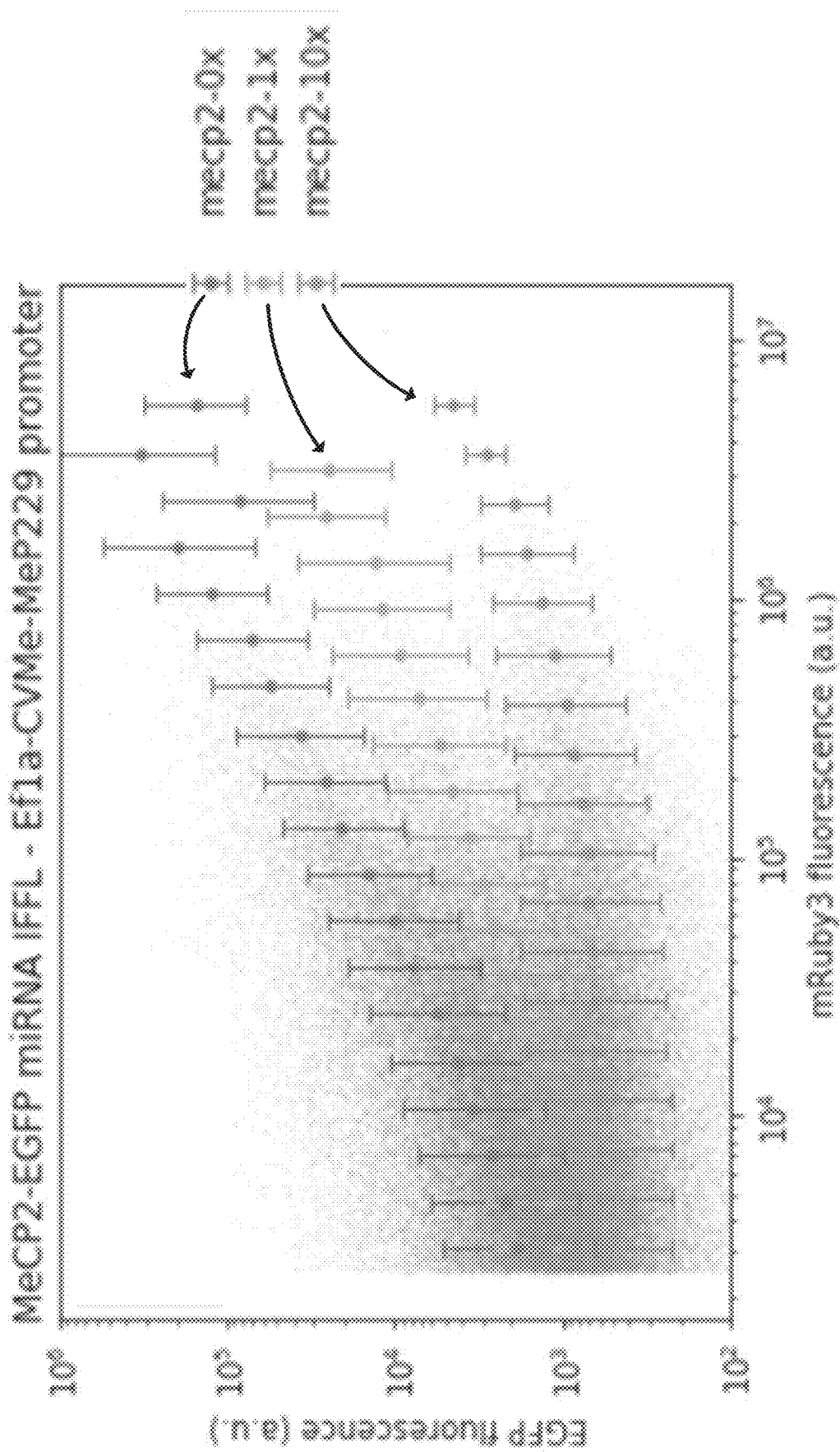

Three different miRNA-level circuits (FIGS. 10A, 11A and 12A) were constructed comprising different promoters. FIG. 10A depicts a first embodiment of a miRNA-level IFFL circuit wherein expression is driven by two separate promoters: Ef1a, which drives the unregulated mCherry expression, and the CMV promoter, which drives the regulated MeCP2-EGFP expression. As seen in FIG. 10B, varying the number of miRNA target sites modulates payload expression. FIG. 11A depicts a second embodiment of a miRNA-level IFFL circuit, optimized to fit inside of an AAV genome. To fit, one bidirectional promoter was constructed by fusing two promoters back to back: Ef1a (without intron) and MeP229, a minimal MeCP2 promoter, which was chosen because it is small. FIG. 11B depicts data related to expression from these construct with a variable number of target sites. FIG. 12A depicts a third embodiment of a miRNA-level IFFL circuit, wherein the construct has the CMV enhancer inserted between the previous two promoters. As seen in FIG. 12B, this circuit composition greatly raised the overall expression of the construct as compared to the construct tested in FIGS. 11A-11B. However, the functional form of steady state levels of the previous construct were maintained.

Figure 13:
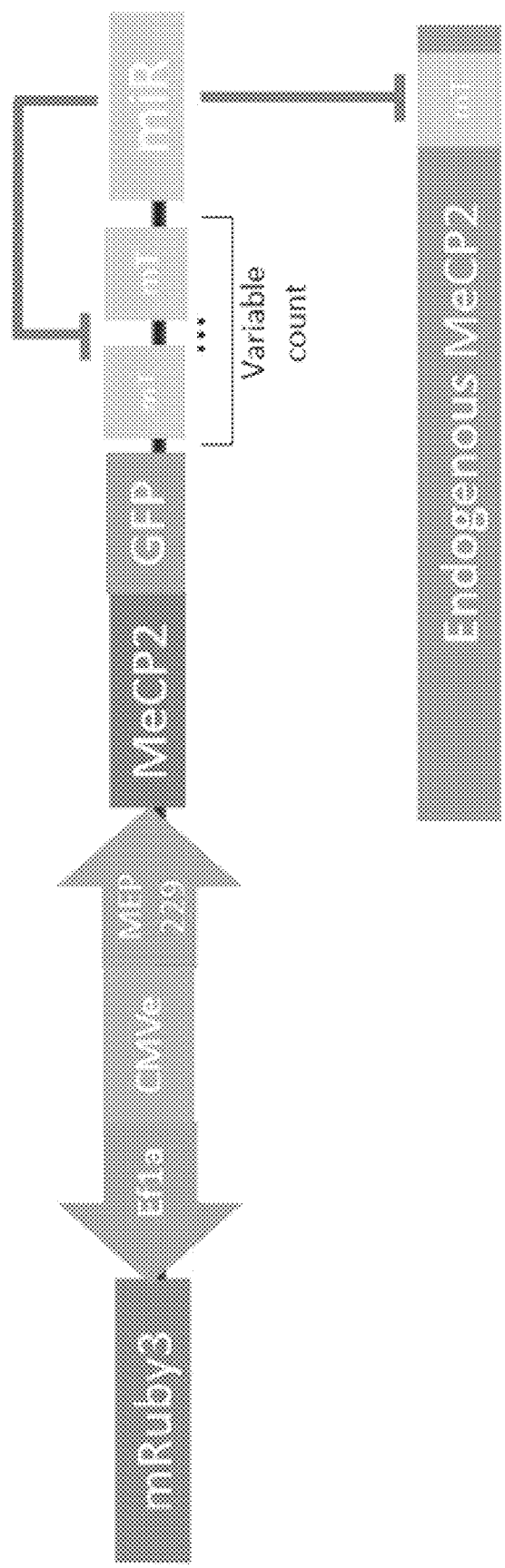
FIG. 13 illustrates a non-limiting exemplary illustration of a miRNA-level IFFL circuit engineered to reduce endogenous MeCP2 expression.

FIG. 13 illustrates a non-limiting exemplary illustration of a miRNA-level IFFL circuit engineered to reduce endogenous MeCP2 expression. By designing the miRNA sequence to target the endogenous MeCP2 transcript, it can be engineered so that the endogenous expression is knocked out and only the regulated expression remains.

Example 5

Exemplary Modeling Robust Gene Expression

An analytic model was derived for the steady state behavior of a protein-level catalytic incoherent feed-forward loop showing dosage compensating behavior. Using ordinary differential equations, the behavior of a circuit was modeled where a protein of interest is cleaved by a co-produced protease, revealing an N-degron which targets the protein for proteasomal degradation. In this Example, we simulate these differential equations and solve for the steady state, both of which show adaptation to the gene dosage. The steady state expression of the protein of interest is given by the expression below, which is dependent on the protease Michaelis Menten parameters $K_m$ and $k_{cat}$, its degradation rate $\gamma$, the faster proteasomal degradation rate $\gamma_{deg}$, and D, the unregulated steady state expression at that gene dosage:

$$P_{ss} = \frac{K_m \gamma}{k_{cat}} \frac{D}{K_m \gamma / k_{cat} + D} + \frac{D\gamma}{\gamma_{deg}} \quad (1)$$

which implies that when D gets much larger than $K_m\gamma/k_{cat}$, but less than $K_m \gamma_{deg}/k_{cat}$, the expression of the protein of interest saturates at $P_{ss} = K_m\gamma/k_{cat}$, independent of D. Thus, in that regime, the circuit adapts to different gene dosages, expressing the protease at the same level.

INTRODUCTION

In gene therapy it is difficult to control the level of payload that gets delivered to any individual cell. In several applications, deleterious effects are associated with over-dosing the delivered gene. For example, gene therapy for Rett syndrome would deliver a functioning version of MECP2 to neurons of an afflicted patient. However, duplication of the MECP2 gene causes the harmful MECP2 duplication syndrome, which would suggest that neurons are sensitive to even 2-fold excesses of MECP2. Another complication is that, since Rett syndrome is an X-linked heterozygous disease, 50% of neurons are expressing healthy levels of MECP2. Therefore, any gene therapy for Rett syndrome must carefully regulate the amount of delivered gene that is expressed to ensure that total levels are in the "Goldilocks" zone. However, it has yet been unclear what kind of regulation would be sufficient to yield an expression profile that saturates past some level of dosage.

In this Example a simple system is modeled where MECP2-degron-tevs is coexpressed with a TEVP, and it is shown analytically and through simulation that this system is sufficient to yield expression of MECP2 that saturates at a high dosage level. Without being bound by any specific theory, it is believed that:

1. for MECP2 production to overwhelm the TEVP, in some embodiments, at least $10^4$ molecules of MECP2 are required to be produced for each TEVP molecule for realistic parameters (each TEVP can cleave around $10^4$ substrates by the time it degrades).

2. at large levels of dosage, the concentration of uncleaved MECP2 approaches and stays beneath an asymptote, and this asymptote is small ($6.2 \times 10^{-4}$ WT MECP2 concentration for realistic parameters). In some embodiments, this asymptote can be pushed higher by reducing the $k_{cat}/K_M$ of the protease—it would need to be reduced 1000-fold to get the desired asymptote.

3. the level of cleaved MECP2 scales with the dosage, but this population is insignificant.

A Simple ODE Model

The dynamics of the system are assumed to be standard production-degradation with Michaelis-Menton kinetics describing the cleavage of uncleaved MECP2 (M) by TEVP (T) to produce cleaved MECP2 ($M_{deg}$). The dosage level of the system is parameterized by the production rate D. A scalar parameter $\alpha$ modifies the production rate of MECP2 to account for a situation where multiple MECP2s are produced for each TEVP (MECP2-P2A-MECP2-T2A-TEVP). All proteins have their respective degradation rates $\gamma_T, \gamma_M, \gamma_{degron}$. The Michaelis-Menton parameters for TEVP are $k_{cat}$ and $K_M$.

$$\dot{T} = D - \gamma_T T$$

$$\dot{M} = D - \gamma_M M - k_{cat} T \frac{M}{K_M + M}$$

$$\dot{M}_{deg} = k_{cat} T \frac{M}{K_M + M} - \gamma_{deg} M_{deg}$$

$$\dot{T} = D - \gamma T$$

$$\dot{M} = D - \gamma M - k_{cat} T \frac{M}{K_M + M}$$

$$\dot{M}_{deg} = k_{cat} T \frac{M}{K_M + M} - \gamma_{deg} M_{deg}$$

To make the equations dimensionless, the time scale was chosen to be $1\gamma_T$. The concentration scale is arbitrary and it was chosen to be $M_{WT}$, the wild-type steady state MECP2 concentration. Defining unitless variables:

$$\gamma = \gamma_M/\gamma_T, \gamma_{deg} = \gamma_{degron}/\gamma_T, k = k_{cat}/\gamma_T, K = \frac{K_M}{M_{WT}}, D = D/(M_{WT}\gamma_T),$$

the ODE can be made dimensionless:

$$\dot{T} = D - T$$

$$\dot{M} = \alpha D - \gamma M - kT \frac{M}{K + M}$$

$$\dot{M}_{deg} = kT \frac{M}{K + M} - \gamma_{deg} M_{deg}$$

The Steady State can be Simplified by Considering Limiting Cases

Since T and M do not depend on $M_{deg}$, it is ignored for now and will be considered later. For the steady states $T_{ss}$ and $M_{ss}$ the derivatives were set to zero to get:

$$T_{ss} = D$$

$$M_{ss}^2 + \left[K + \frac{1}{\gamma}(k-\alpha)D\right]M_{ss} - \frac{K\alpha D}{\gamma} = 0$$

The quadratic formula can be used to solve for $M_{ss}$ (the minus root has been eliminated by proving that it is always negative, proof omitted):

$$M_{ss} = \frac{1}{2}\left[-\left[K + \frac{1}{\gamma}(k-\alpha)D\right] + \sqrt{\left(K + \frac{1}{\gamma}(k-\alpha)D\right)^2 + 4\frac{K\alpha D}{\gamma}}\right]$$

The complicated form of this solution is an obstacle to analysis. However, we are mostly concerned with limiting cases when D gets very large. In those situations, the $1/\gamma(k-\alpha)D$ terms dominate, and the behavior depends on the sign of $(k-\alpha)$.

Case of interest 1: $k-\alpha<0$, $D\gg K$, MECP2 expression runs away with dosage If $k<\alpha$, more MECP2 is created per unit of TEVP than can be catalytically degraded by TEVP by the time that it degrades. This case captures the worry that there is some level of MECP2 expression that cannot be contained by TEVP.

In the regime where D is large, the $$\frac{1}{\gamma}(k-\alpha)$$

D term dominates the other terms in the square root, leading to the approximation:

$$M_{ss} \approx -\frac{1}{2}\left[\frac{1}{\gamma}(k-\alpha)D\right] + \frac{1}{2}\left|\frac{1}{\gamma}(k-\alpha)D\right|.$$

This can be further simplified to:

$$M_{ss} \approx \frac{(\alpha-k)}{\gamma}D$$

Thus the expression of MECP2 is linearly dependent on the dose in this regime. However, this regime is hard to get to. Since $\alpha \approx 1$ for our designs, this regime would mean that $k_{cat}$ for TEVP is on the order of its degradation rate or slower. This is orders of magnitude slower than it really is. Thus we believe we can be comfortable assuming we are in the situation where $k-\alpha>0$.

Case of Interest 2: $k-\alpha>0$, $D\gg K$, MECP2 Expression Approaches Asymptote When $k-\alpha>0$, we cannot use the same trick as before since the answer comes out to 0—we must consider the higher order terms. We factor the squared term out of the square root and this gives me a term with D in the denominator, so it must be very small. We use small argument expansion on the square root ($\sqrt{1+x} \approx 1+x/2$ for small x) to get:

$$M_{ss} = \frac{1}{2}\left[-\left[K + \frac{1}{\gamma}(k-\alpha)D\right] + \left(K + \frac{1}{\gamma}(k-\alpha)D\right)\sqrt{1 + \frac{4K\alpha}{D\gamma\left(\frac{K}{D} + \frac{1}{\gamma}(k-\alpha)\right)^2}}\right]$$

$$\approx \frac{1}{2}\left[-\left[K + \frac{1}{\gamma}(k-\alpha)D\right] + \left(K + \frac{1}{\gamma}(k-\alpha)D\right)\left(1 + \frac{2K\alpha}{D\gamma\left(\frac{K}{D} + \frac{1}{\gamma}(k-\alpha)\right)^2}\right)\right]$$

$$M_{ss} \approx \frac{K\alpha}{k-\alpha} \frac{D}{\gamma K/(k-\alpha) + D}$$

The asymptotic limit as $D \to \infty$ is:

$$M_{asym} = \frac{K\alpha}{k-\alpha} \approx \frac{K}{k} \text{ for } \alpha = 1$$

Thus we have a system that approaches but never exceeds the ratio of K and k, a good rule of thumb.

$$M_{ss} \approx \frac{K_M}{k_{cat}/\gamma - 1} \frac{D}{\frac{\gamma K_M}{k_{cat}/\gamma - 1} + D} \xrightarrow{D \to \infty} \frac{\gamma K_M}{k_{cat}}$$

$$D_{max} = \frac{K_M}{k_{cat}/\gamma_T - 1}(\gamma_{deg} - \gamma_M)$$

$$D_{thresh} = \frac{\gamma_M K_M}{k_{cat}/\gamma_T - 1}$$

$$\text{Range} = \frac{\gamma_{deg} - \gamma_M}{\gamma_M}$$

$$M_{ss} \approx \frac{\gamma K_M}{k_{cat}} \frac{D}{\frac{\gamma K_M}{k_{cat}} + D} \xrightarrow{D \to \infty} \frac{\gamma K_M}{k_{cat}}$$

$$\frac{D_{max}}{D_{thresh}} = \frac{\gamma_{deg}}{\gamma_M}$$

Cleaved Population Scales with D

Returning to the cleaved MECP2 component of the ODE:

$$\dot{M}_{deg} = kT\frac{M}{K+M} - \gamma_{deg}M_{deg}$$

We can solve for the steady state in terms of the asymptotic steady state of M:

$$M_{deg} = \frac{kD}{\gamma_{deg}} \frac{M_{ss}}{K + M_{ss}}$$

$$= \frac{kD}{\gamma_{deg}} \frac{K\alpha/(k-\alpha)}{K + K\alpha/(k-\alpha)}$$

$$M_{deg} \approx \frac{D}{\gamma_{deg}}$$

Thus the population of cleaved MECP2 scales with the dosage, but has a reasonably large divisor in $\gamma_{deg}$. This technically breaks the "dosage-independence" but if the degradation rate is significantly fast then the slope will be very small.

Choosing Realistic Parameters

MECP2 Concentration Scale

From Skene et al. (Molecular cell, 2010) describes that "The amount of MeCP2 in sorted neuronal nuclei (NeuN positive) was $16\times10^6$ molecules per nucleus", which is $2.7\times10^{-17}$ mols. Modeling the nucleus as a sphere of 10 micrometers in diameter, the volume is:

$$\tfrac{3}{4}\pi(10\times10^{-6}\text{ m})^3 = 4.19\times10^{-15}\text{ m}^3 = 4.19\times10^{-12}\text{ liters}.$$

To compute the molarity we divide the mols by the volume in liters to get:

$$M_{WT} = \frac{2.7\times10^{-17}\text{ mols}}{4.19\times10^{-12}\text{ liters}} = 6.4\ \mu M.$$

TEVP Kinetics

Kapust et al. (*Protein engineering*, 2001) list the TEVP $K_M$ values ranging around 50 μM and $k_{cat}$ values ranging around $0.15\text{ s}^{-1}$.

Degradation Rates

Bionumbers lists the average protein half life in human cells as around 30 hours. Yen, Hsueh-Chi Sherry, et al. (Science, 2008) lists the half life of a GFP with a degron as 1 hour. Based on these numbers we set: $\gamma_T = \gamma_M = (1/30)\text{ hr}^{-1}$ and $\gamma_{degron} = 1\text{ hr}^{-1}$.

Final Parameter List:

$\alpha\approx 1$ There is one MECP2-T2A-TEVP $\gamma\approx 1$ this Example assumes there is no significant difference between the degradation rate of TEVP and MECP2

$\gamma_{deg}\approx 100$ degron increases degradation rate approximately 100-fold.

$K=10$ because the measured TEVP $K_m$ value is about 10 times the WT neural concentration of MECP2.

$k=0.15\text{ s}^{-1}/(1/30)\text{ hr}^{-1} = 1.62\times10^4$ One TEVP molecule can cleave around $10^4$ substrates by the time it degrades.

Simulation

Figure 14B:
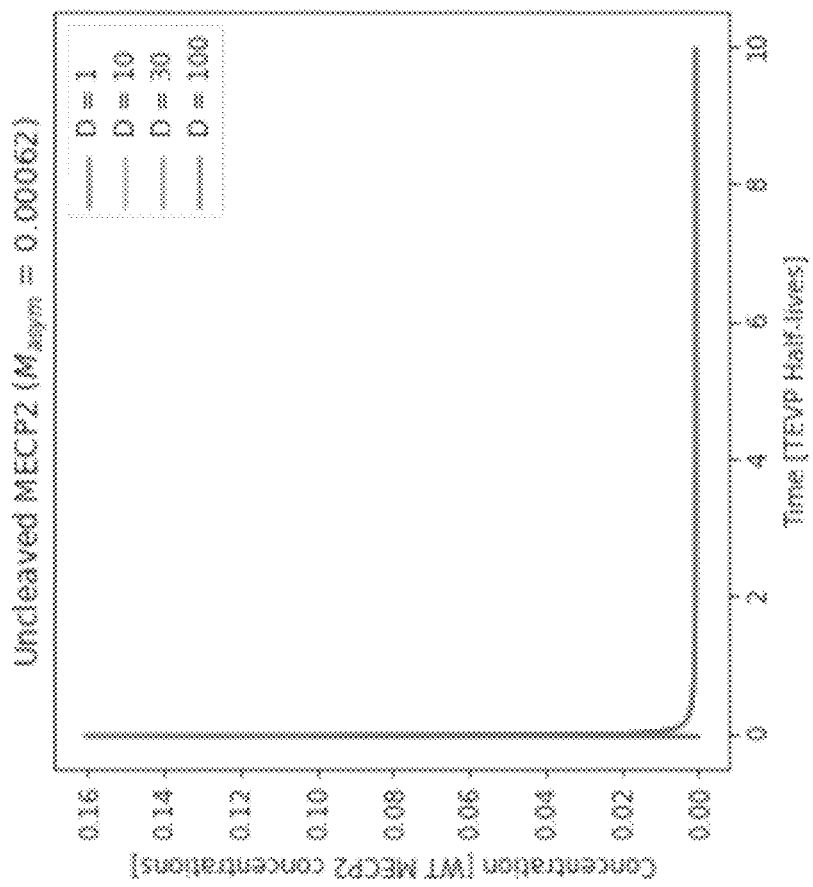
Figure 14C:
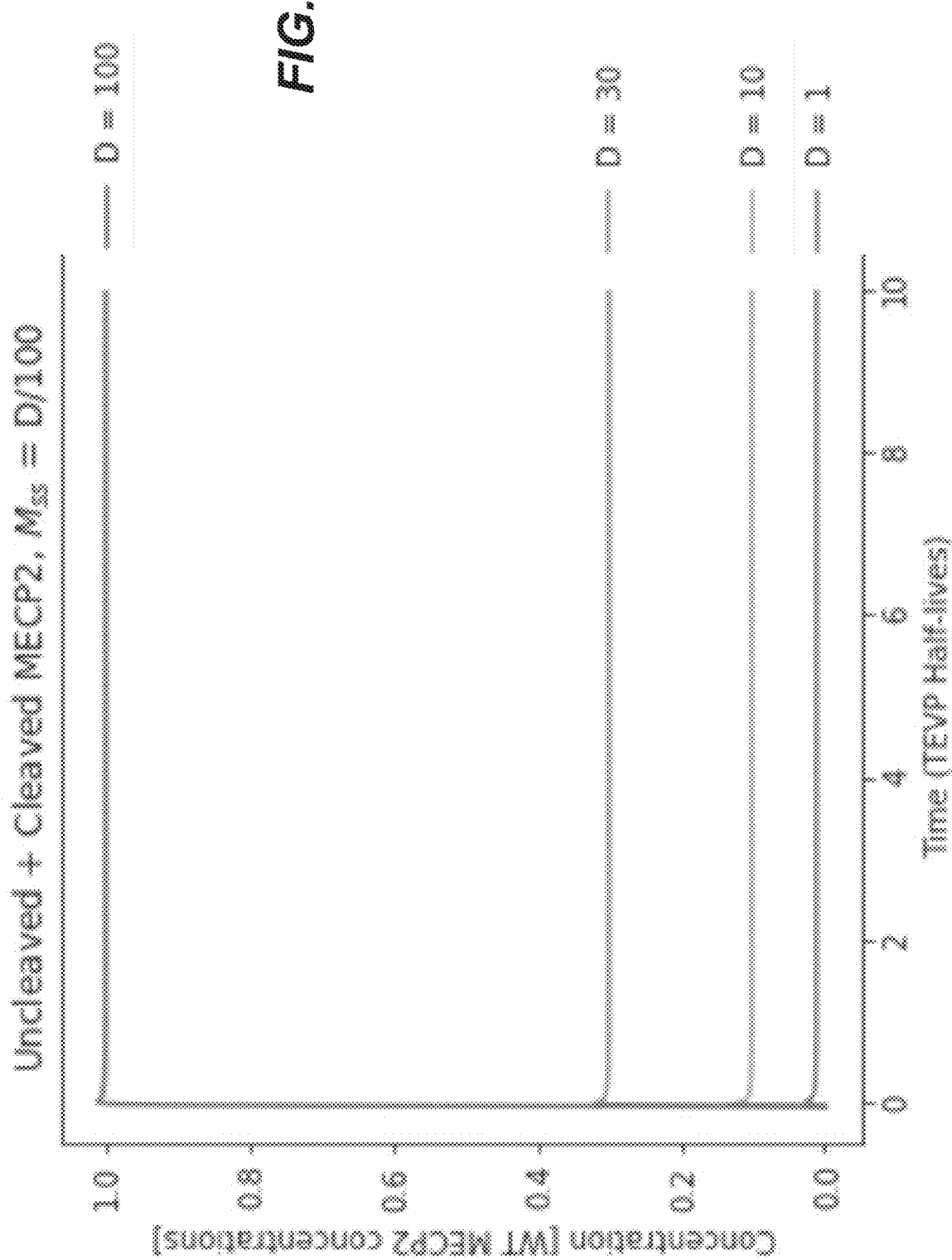
Figure 15B:
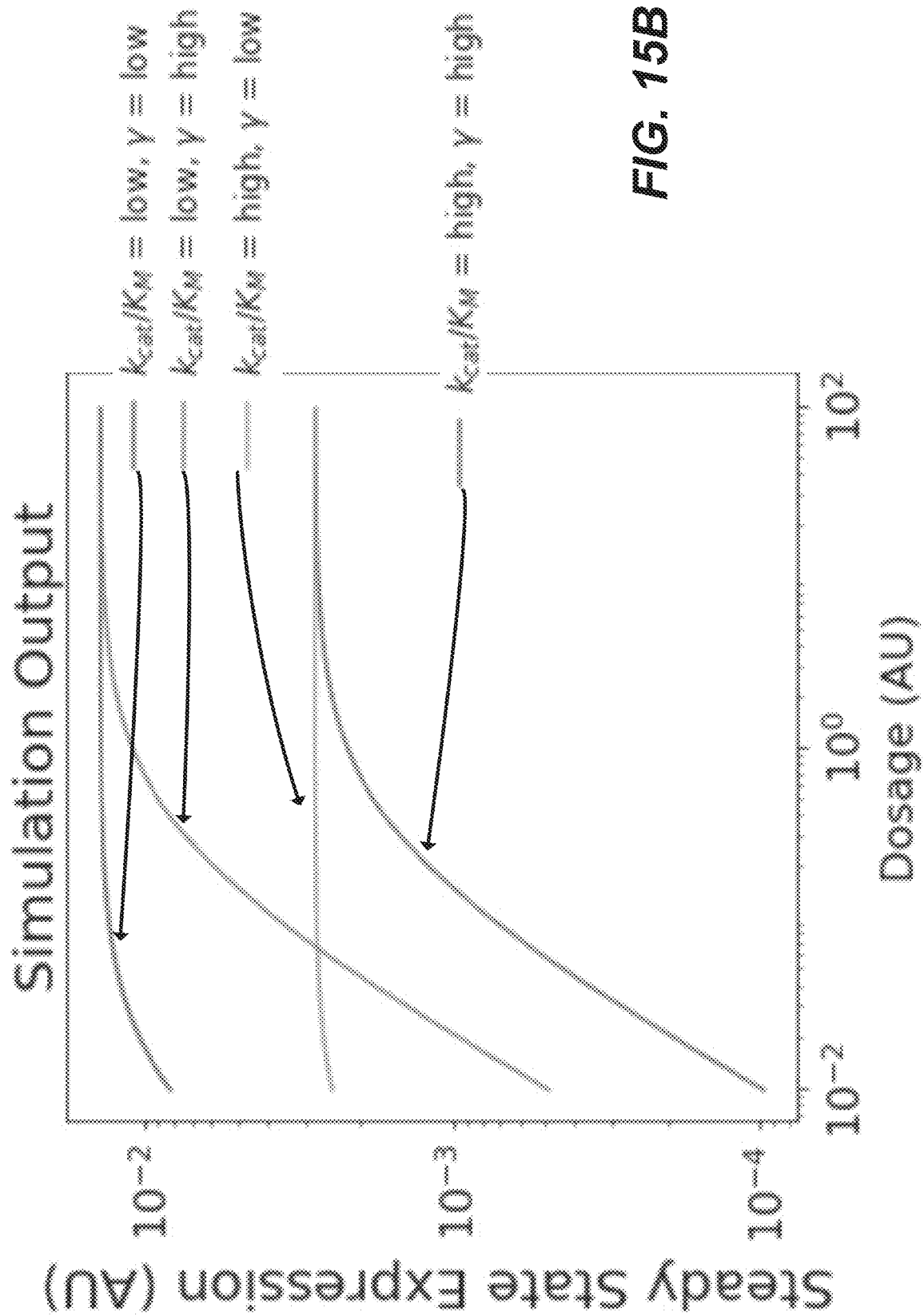
Figure 16B:
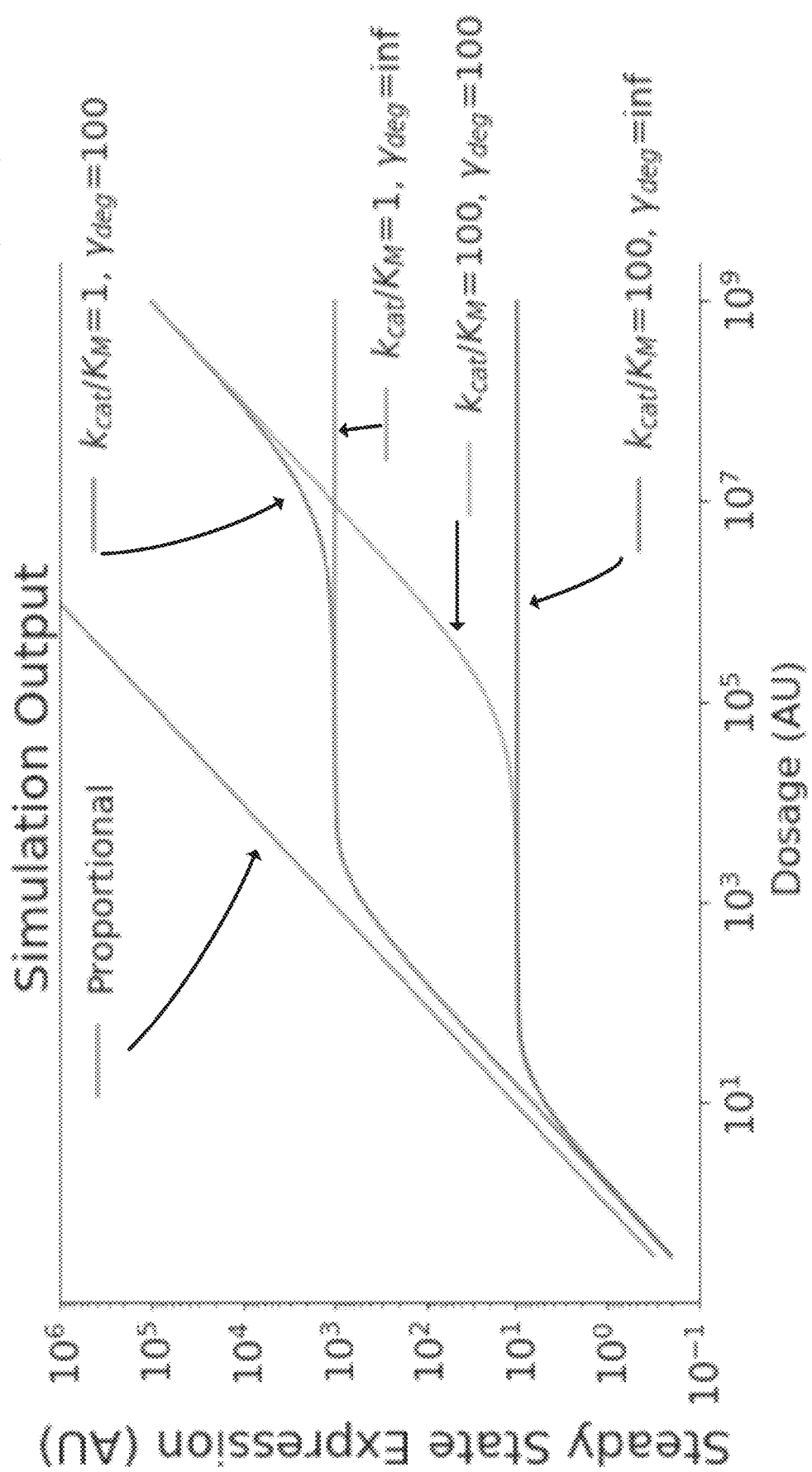
Figure 17B:
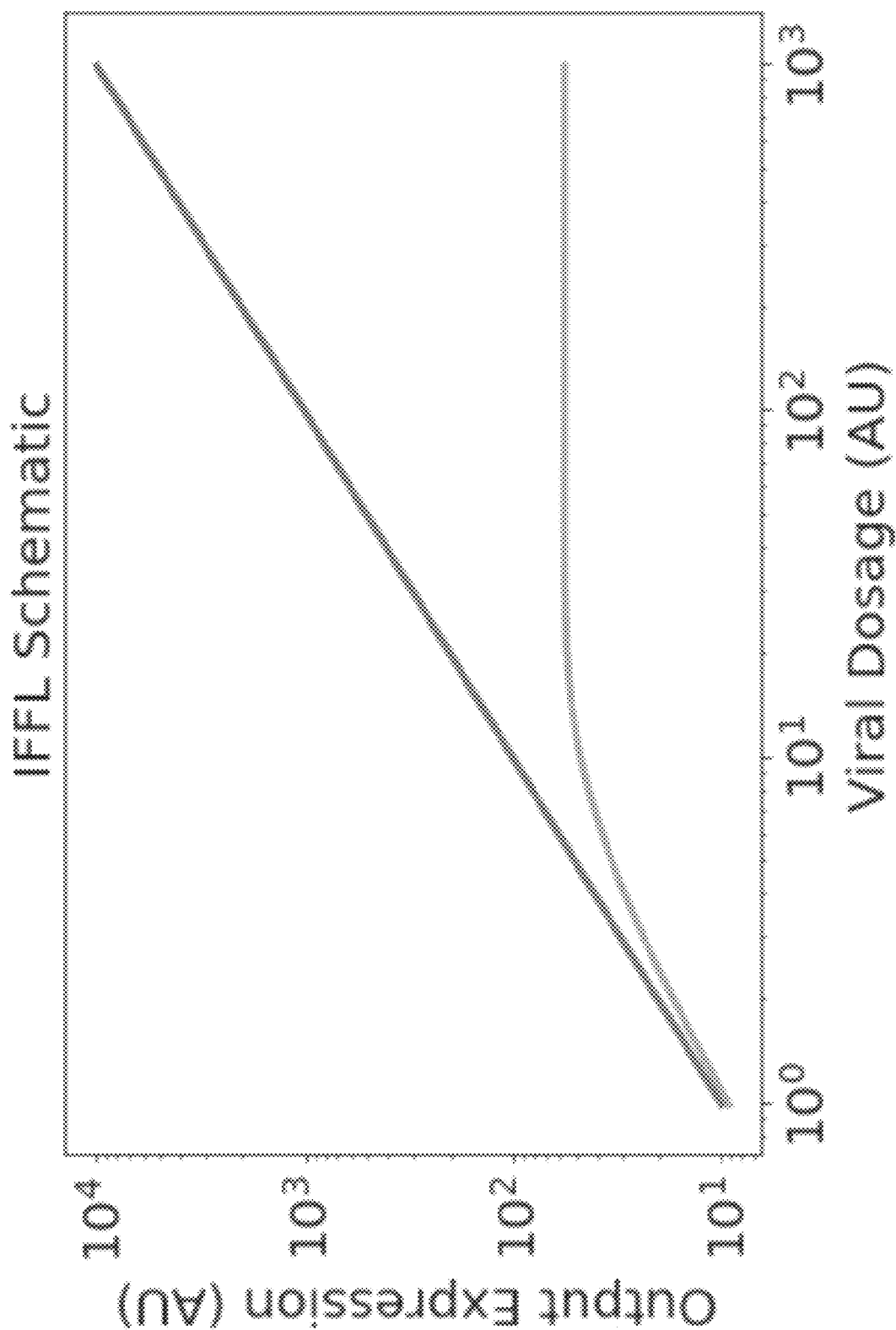
Figure 18B:
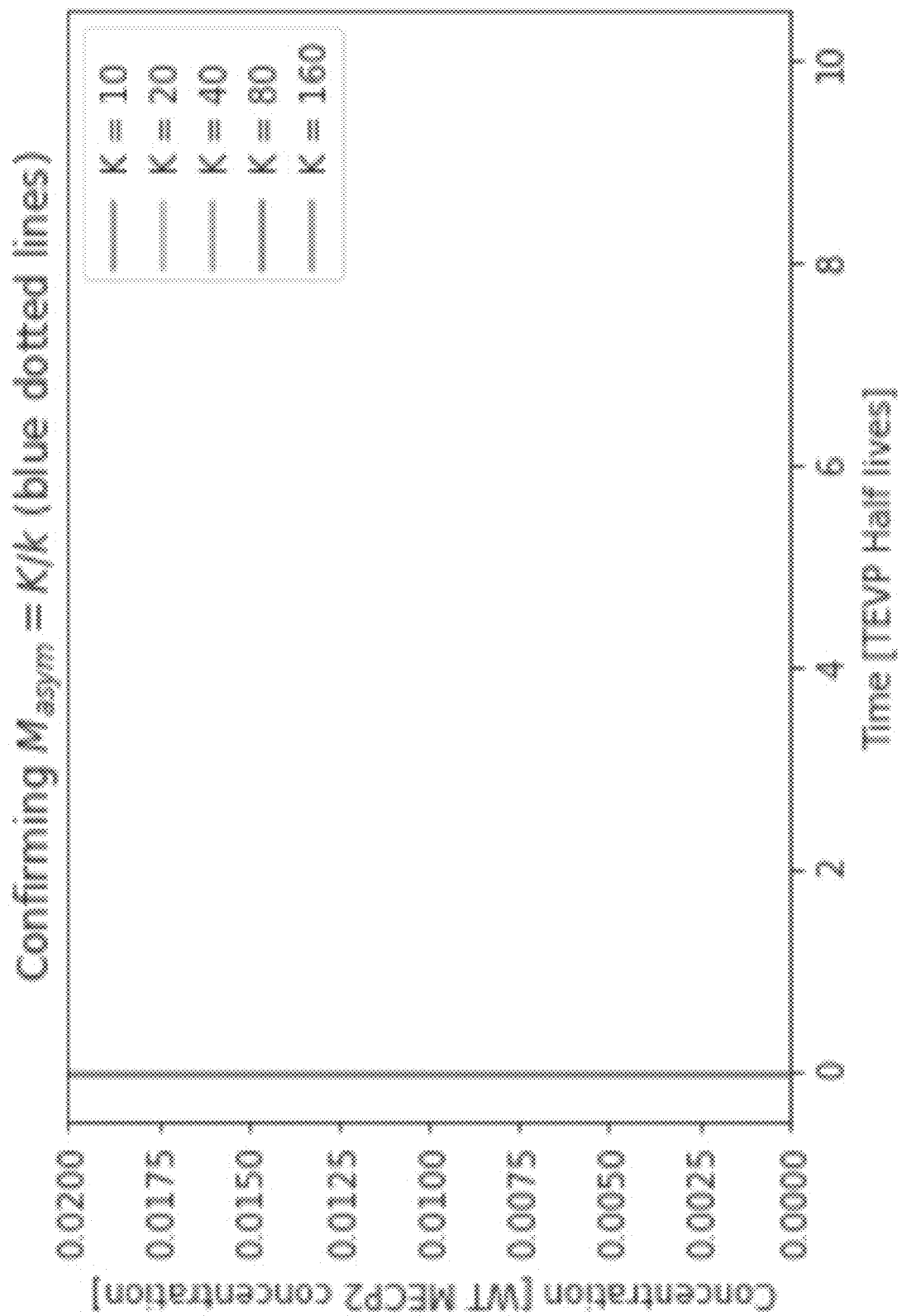
Figure 19B:
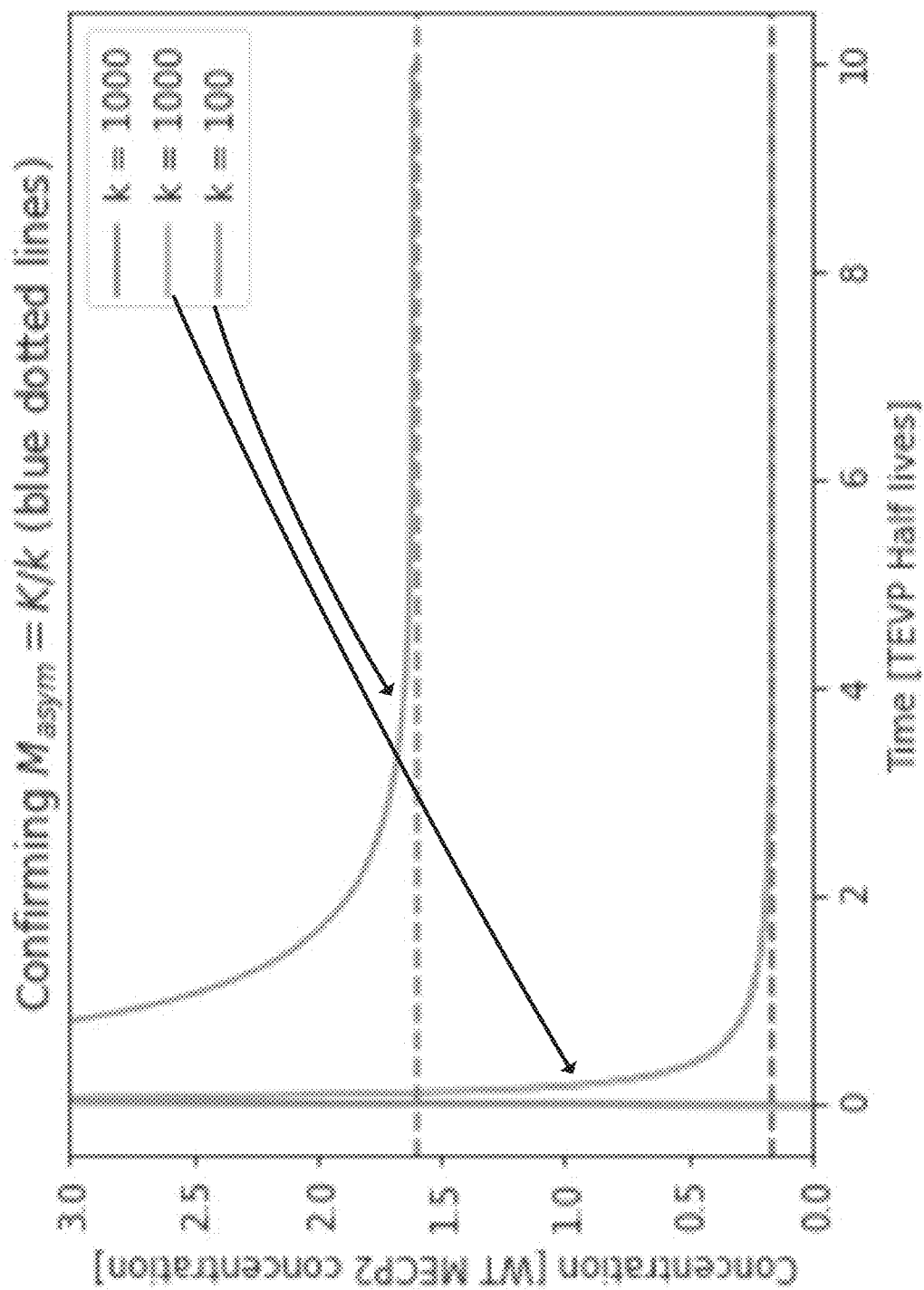

Given the parameters above, the circuit was simulated with the code shown in FIG. 14A for dosages D equal to 1, 10, 30, and 100. The uncleaved population, after a sharp peak, settles to an asymptote that seems to agree with the formula $M_{asym} = K/k = 0.00062$. The cleaved population dominates with $10^4$ times higher concentration and seems to agree with the formula $M_{deg} = D/\gamma_{deg} = D/30$, and thus up to $D=30$, it seem to be within reasonable dosage range for these parameters. FIG. 14A-14C depict non-limiting exemplary code and simulations.

Checking the Functional Form of the Dosage-Expression Relationship

Next, it was checked how well the approximation $$P_{ss} = \frac{K_M\gamma}{k_{cat}}\frac{D}{\gamma\frac{K_M\gamma}{k_{cat}} + D} + \frac{D}{\gamma_{deg}}$$

fits the output of the simulation. FIGS. 15A-15B, 16A-16B, and 17A-17B depict non-limiting exemplary code and simulations.

Confirming that the Uncleaved Asymptote Scales with K/k:

As seen in FIGS. 18A-18B and 19A-19B, which depict non-limiting exemplary code and simulations, we varied K or k and checked the formula $M_{asym} = K/k$ by labeling the location with a blue dashed line. In all cases the formula works well.

Confirming that Runaway Threshold is $k-\alpha=0$

Figure 20B:
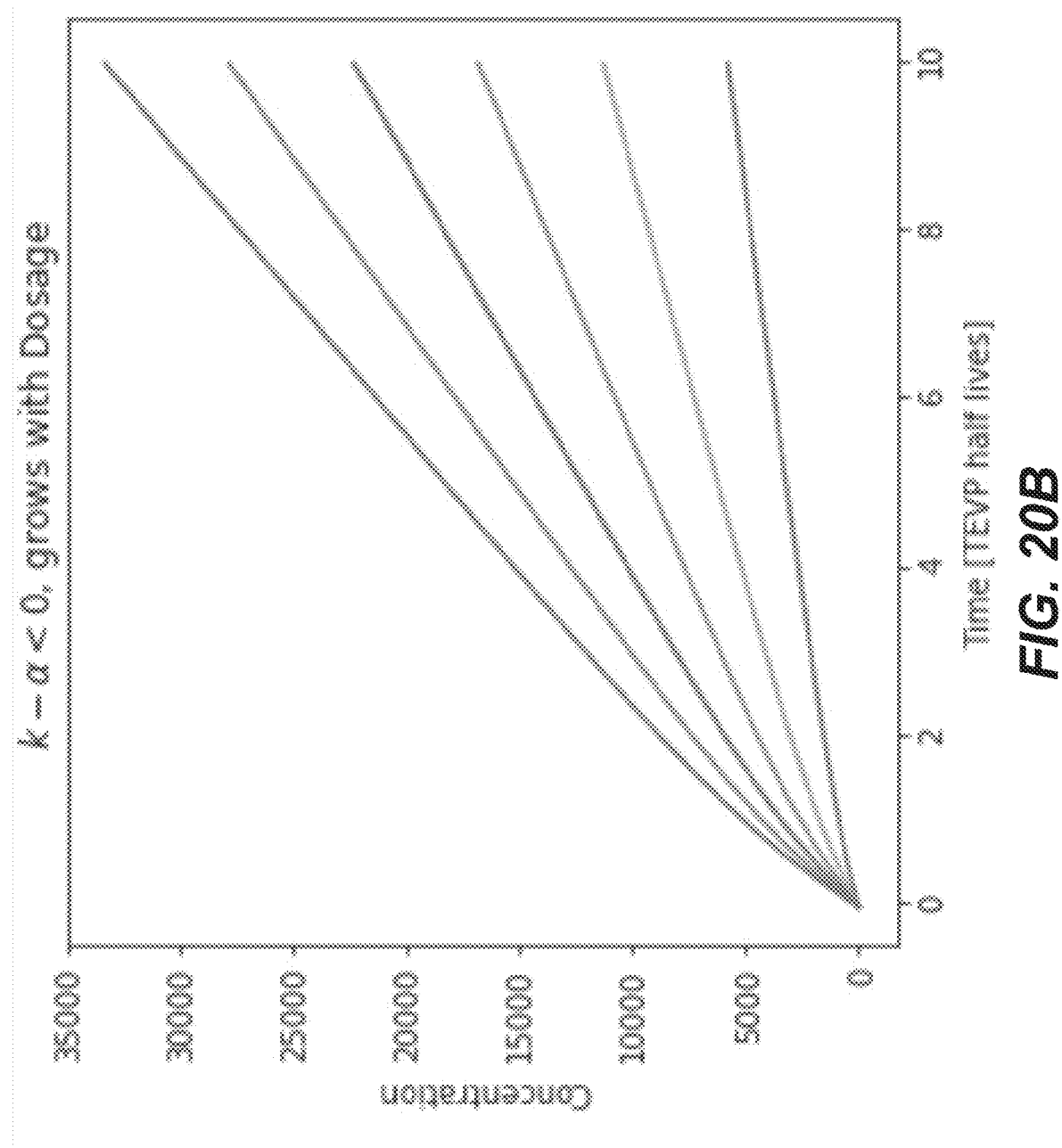
Figure 20C:
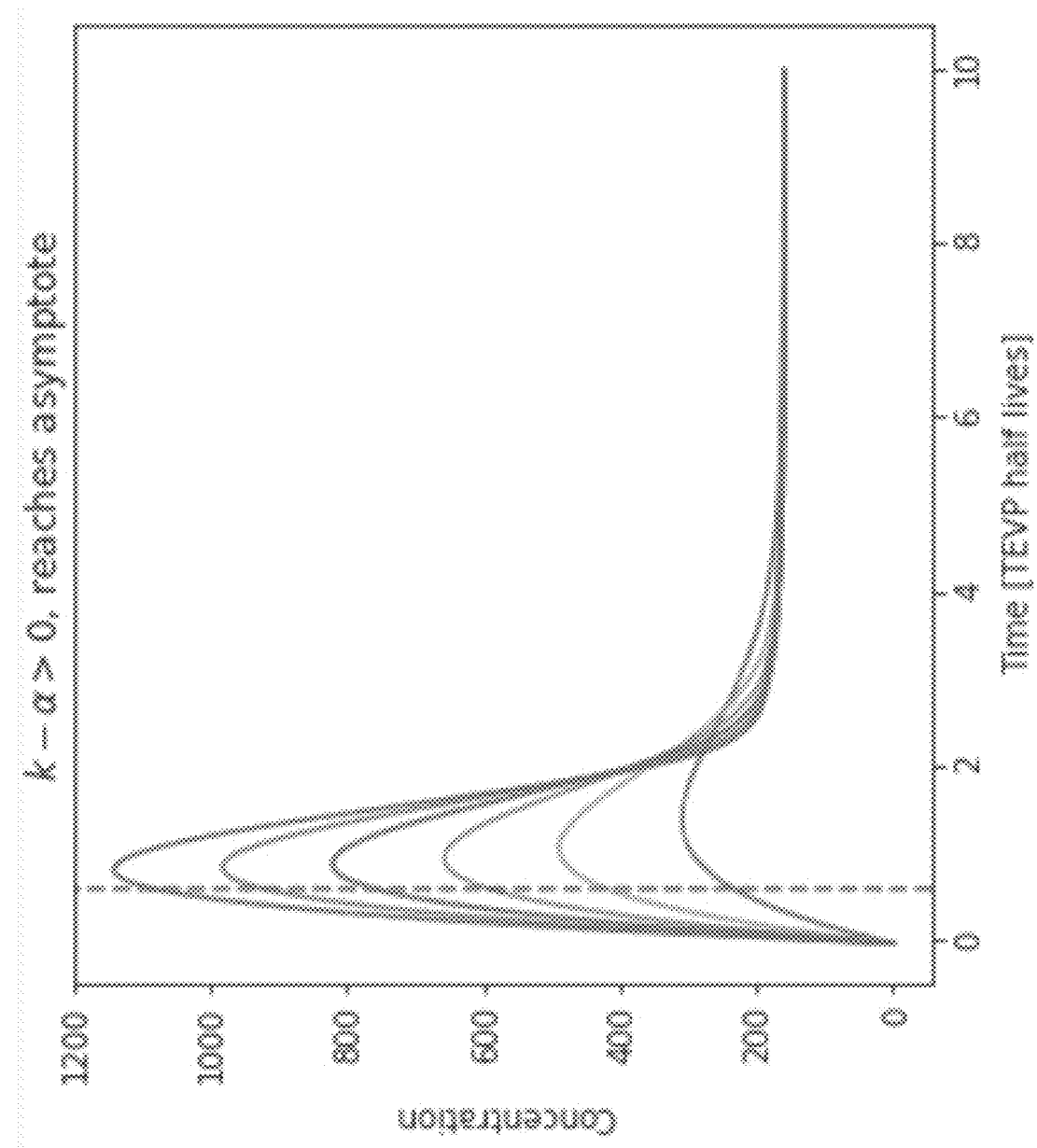

FIGS. 20A-20C depict non-limiting exemplary code and simulations. The first example here is where $k-\alpha<0$, the second where $k-\alpha>0$. The first should have runaway behavior with dosage, the second, asymptotic. This behavior was confirmed with the plots.

Ideal Situation K/k=0.33

Figure 21B:
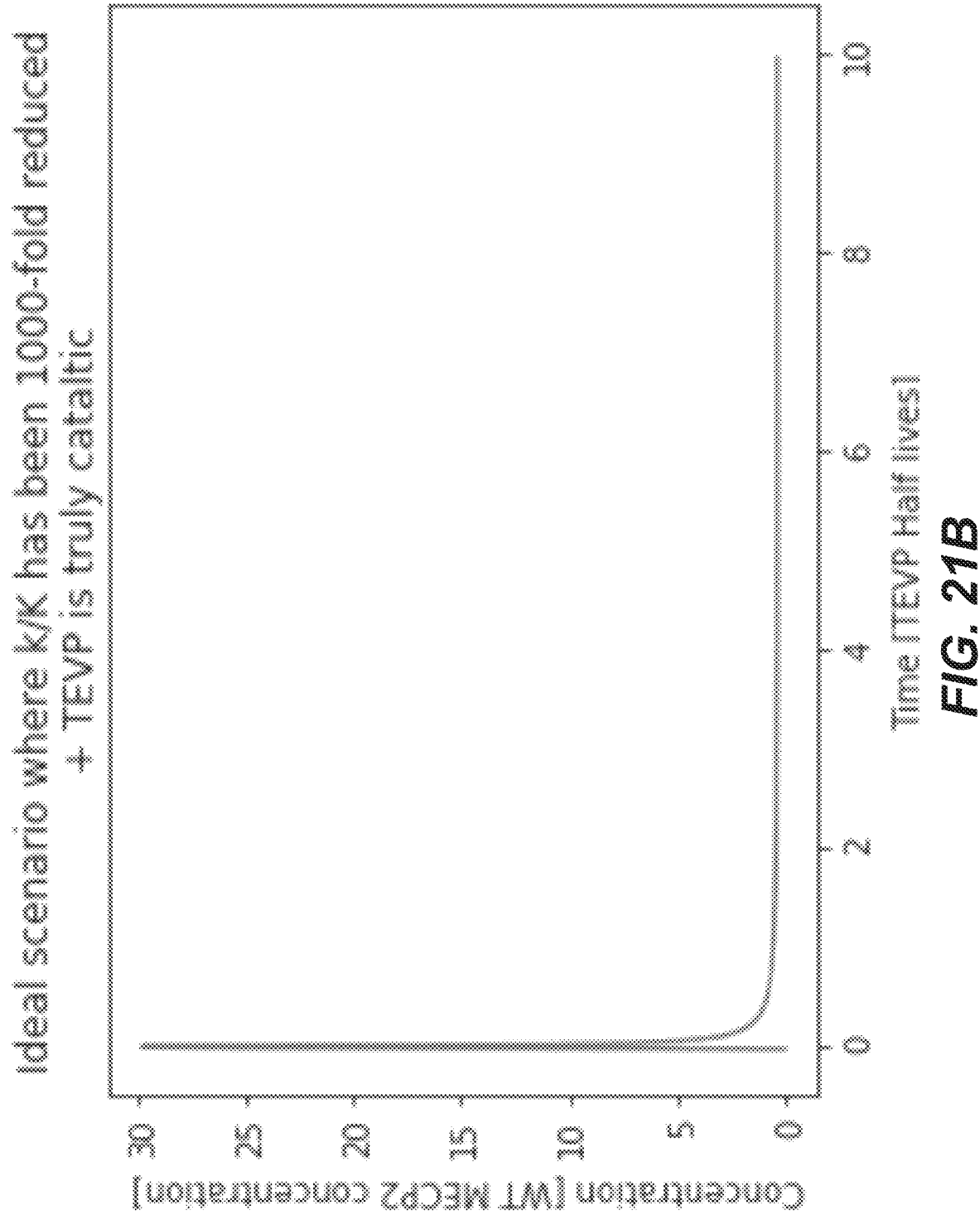

FIGS. 21A-21B depict non-limiting exemplary code and simulations. This plot is of a situation where k/K of TEVP has been reduced by around 1000-fold and TEVP is purely catalytic. In this case, we get a steady state concentration of MECP2 that is suitable for gene therapy.

Predicted Behavior for Known Substrates

From Tözsér, József, et al. (FEBS, 2005), TEVP $k_{cat}/K_M$ values are known:

```
ETVFFQ (SEQ ID NO: 1) ≈ 0.007
ENAYFQ (SEQ ID NO: 2) ≈ 0.027
ENLFFQ (SEQ ID NO: 3) ≈ 0.35
ENLYFQ (SEQ ID NO: 4) ≈ 4.51
```

Figure 22B:
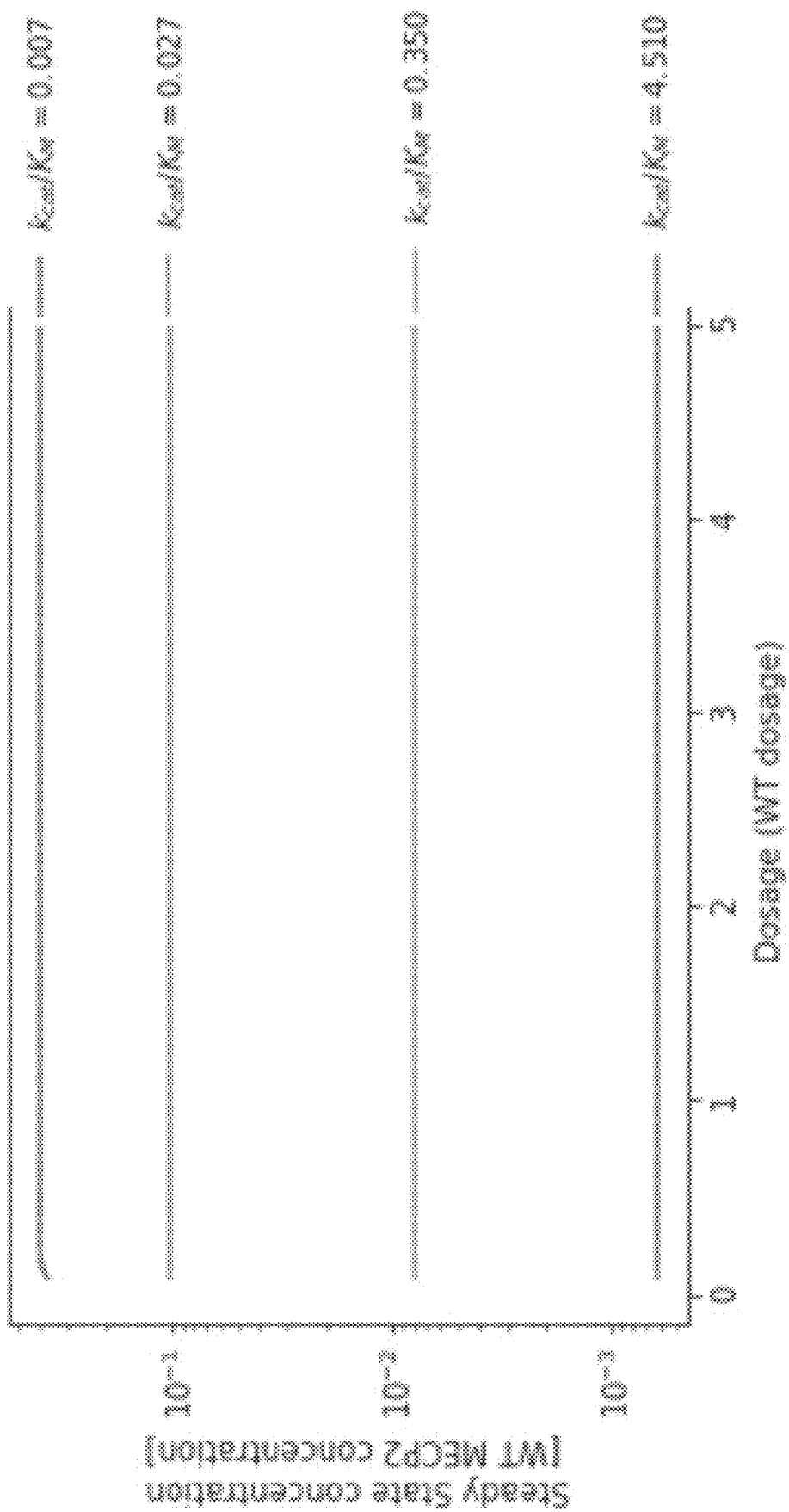

Predicted output concentrations are shown in the non-limiting exemplary code and simulations of FIGS. 22A-22B.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: TEVP cut site

<400> SEQUENCE: 1

Glu Thr Val Phe Phe Gln
1               5

<210> SEQ ID NO 2
<211> LENGTH: 6
<212> TYPE: PRT
<213> ORGANISM: Artificial Sequence
<220> FEATURE:
<223> OTHER INFORMATION: TEVP cut site

<400> SEQUENCE: 2

Glu Asn Ala Tyr Phe Gln
1               5

<210> SEQ ID NO 3
<211> LENGTH: 6
<212> TYPE: PRT
<213> ORGANISM: Artificial Sequence
<220> FEATURE:
<223> OTHER INFORMATION: TEVP cut site
```

```
<400> SEQUENCE: 3

Glu Asn Leu Phe Phe Gln
1               5

<210> SEQ ID NO 4
<211> LENGTH: 6
<212> TYPE: PRT
<213> ORGANISM: Artificial Sequence
<220> FEATURE:
<223> OTHER INFORMATION: TEVP cut site

<400> SEQUENCE: 4

Glu Asn Leu Tyr Phe Gln
1               5

<210> SEQ ID NO 5
<211> LENGTH: 7
<212> TYPE: PRT
<213> ORGANISM: Artificial Sequence
<220> FEATURE:
<223> OTHER INFORMATION: TEVP cut site

<400> SEQUENCE: 5

Glu Asn Leu Tyr Phe Gln Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: TEVP cut site

<400> SEQUENCE: 6

Glu Asn Leu Tyr Phe Gln Phe
1               5

<210> SEQ ID NO 7
<211> LENGTH: 7
<212> TYPE: PRT
<213> ORGANISM: Artificial Sequence
<220> FEATURE:
<223> OTHER INFORMATION: TEVP cut site

<400> SEQUENCE: 7

Glu Asn Leu Tyr Phe Gln Gln
1               5

<210> SEQ ID NO 8
<211> LENGTH: 7
<212> TYPE: PRT
<213> ORGANISM: Artificial Sequence
<220> FEATURE:
<223> OTHER INFORMATION: TEVP cut site

<400> SEQUENCE: 8

Glu Asn Leu Phe Phe Gln Tyr
1               5
```

What is claimed is:

1. A nucleic acid comprising:
a promoter operably linked to a polynucleotide encoding a fusion protein comprising a payload protein, a protease, and one or more self-cleaving peptide sequences, wherein the payload protein comprises a degron and a cut site the protease is capable of cutting to expose the degron, wherein the degron of the payload protein being exposed changes the payload protein to a payload protein destabilized state,
wherein the self-cleaving peptide sequence comprises porcine teschovirus-1 2A peptide (P2A), Thosea asigna virus 2A peptide (T2A), equine rhinitis A virus 2A peptide (E2A), foot-and-mouth disease virus 2A peptide (F2A), or any combination thereof, and wherein the protease comprises tobacco etch virus (TEV) protease, tobacco vein mottling virus (TVMV) protease, hepatitis C virus protease (HCVP), derivatives thereof, or any combination thereof.

2. The nucleic acid of claim 1, wherein the degron comprises an N-degron.

3. The nucleic acid of claim 1, wherein one or more cells comprise an endogenous version of a gene encoding the payload protein comprising one or more secondary silencer binding sequences in the 3'UTR, wherein the nucleic acid comprises a secondary silencer effector cassette encoding a secondary silencer effector that is capable of binding the one or more secondary silencer binding sequences.

4. The nucleic acid of claim 1, wherein the polynucleotide further comprises a transcript stabilization element, and wherein the transcript stabilization element comprises woodchuck hepatitis post-translational regulatory element (WPRE), bovine growth hormone polyadenylation (bGH-polyA) signal sequence, human growth hormone polyadenylation (hGH-polyA) signal sequence, or any combination thereof.

5. The nucleic acid of claim 1, wherein the promoter comprises a ubiquitous promoter, and wherein the ubiquitous promoter is selected from the group comprising a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CBH promoter, or any combination thereof.

6. The nucleic acid of claim 1, wherein the promoter is an inducible promoter, wherein the inducible promoter is a tetracycline responsive promoter, a TRE promoter, a Tre3G promoter, an ecdysone responsive promoter, a cumate responsive promoter, a glucocorticoid responsive promoter, and estrogen responsive promoter, a PPAR-γ promoter, an RU-486 responsive promoter, or any combination thereof.

7. The nucleic acid of claim 1, wherein the promoter comprises a tissue-specific promoter, wherein the tissue specific promoter is a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, a cardiac Troponin T (cTnT) promoter, or any combination thereof.

8. The nucleic acid of claim 1, wherein the promoter comprises a tissue-specific promoter, wherein the tissue specific promoter is a neuron-specific promoter, wherein the neuron-specific promoter comprises a synapsin-1 (Syn) promoter, a CaMKIIa promoter, a calcium/calmodulin-dependent protein kinase II a promoter, a tubulin alpha I promoter, a neuron-specific enolase promoter, a platelet-derived growth factor beta chain promoter, TRPV1 promoter, a $Na_v1.7$ promoter, a $Na_v1.8$ promoter, a $Na_v1.9$ promoter, an Advillin promoter, or any combination thereof.

9. The nucleic acid of claim 1, wherein the promoter comprises an intronic sequence, a bidirectional promoter and/or an enhancer.

10. The nucleic acid of claim 1, wherein one or more cells comprise an endogenous version of the payload gene, and wherein the promoter comprises or is derived from the promoter of the endogenous version.

11. The nucleic acid of claim 1, wherein the payload protein comprises a disease-associated protein, wherein aberrant expression of the disease-associated protein correlates with the occurrence and/or progression of the disease.

12. The nucleic acid of claim 1, wherein the payload protein comprises methyl CpG binding protein 2 (MeCP2), DRK1A, KAT6A, NIPBL, HDAC4, UBE3A, EHMT1, one or more genes encoded on chromosome 9q34.3, NPHP1, LIMK1 one or more genes encoded on chromosome 7q11.23, P53, TPI1, FGFR1 and related genes, RAL SHANK3, CLN3, NF-1, TP53, PFK, CD40L, CYP19A1, PGRN, CHRNA7, PMP22, CD40LG, derivatives thereof, or any combination thereof.

13. The nucleic acid of claim 1, wherein the payload protein comprises a programmable nuclease, a diagnostic agent, a chimeric antigen receptor, a CRE recombinase, GCaMP, a cell therapy component, a knock-down gene therapy component, a cell-surface exposed epitope, or any combination thereof.

14. A composition comprising the nucleic acid of claim 1, wherein the composition is a vector, a ribonucleoprotein (RNP) complex, a liposome, a nanoparticle, an exosome, a microvesicle, or any combination thereof.

15. The composition of claim 14, wherein the vector is a viral vector, a plasmid, a naked DNA vector, a lipid nanoparticle, or any combination thereof.

16. A method of treating a disease or disorder in a subject, the method comprising:
introducing into one or more cells of a subject in need thereof the composition of claim 14.

17. The method of claim 16, wherein, in the absence of the protease and/or the silencer effector, the payload protein reaches untuned steady state payload protein levels in the one or more cells, wherein untuned steady state payload protein levels range between a lower untuned threshold and an upper untuned threshold of an untuned expression range, wherein, in the presence the protease and/or the silencer effector, the payload protein reaches tuned steady state payload protein levels in the one or more cells, wherein tuned steady state payload protein levels range between a lower tuned threshold and an upper tuned threshold of a tuned expression range, wherein the difference between the lower untuned threshold and the upper untuned threshold of the untuned expression range is greater than about two orders of magnitude, and wherein the difference between the lower tuned threshold and the upper tuned threshold of the tuned expression range is less than about one order of magnitude.

18. The method of claim 17, wherein the lower tuned threshold and/or the upper tuned threshold of a tuned expression range can be increased by introducing one or more non-canonical amino acid substitutions into the cut site, and wherein the lower tuned threshold and/or the upper tuned threshold of a tuned expression range can be reduced by introducing one or more canonical amino acid substitutions into the cut site.

* * * * *